US011293041B2

(12) United States Patent
Rudenko et al.

(10) Patent No.: US 11,293,041 B2
(45) Date of Patent: *Apr. 5, 2022

(54) NEUROTRANSMITTERS AND METHODS OF MAKING THE SAME

(71) Applicant: Purissima, Inc., South San Francisco, CA (US)

(72) Inventors: George Rudenko, Mountain View, CA (US); Robert Evans, Danville, CA (US)

(73) Assignee: Purissima, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/894,617

(22) Filed: Jun. 5, 2020

(65) Prior Publication Data

US 2020/0340026 A1    Oct. 29, 2020

Related U.S. Application Data

(63) Continuation of application No. 15/971,893, filed on May 4, 2018, now Pat. No. 10,704,066.

(60) Provisional application No. 62/501,747, filed on May 5, 2017.

(51) Int. Cl.
| | |
|---|---|
| *C12P 17/06* | (2006.01) |
| *C12N 1/12* | (2006.01) |
| *C07D 311/80* | (2006.01) |
| *C12N 15/52* | (2006.01) |
| *C12N 9/10* | (2006.01) |
| *C12N 9/02* | (2006.01) |
| *C12N 9/00* | (2006.01) |
| *C12P 7/42* | (2006.01) |
| *C12N 9/88* | (2006.01) |

(52) U.S. Cl.
CPC ............ *C12P 17/06* (2013.01); *C07D 311/80* (2013.01); *C12N 1/12* (2013.01); *C12N 9/001* (2013.01); *C12N 9/0067* (2013.01); *C12N 9/1029* (2013.01); *C12N 9/1085* (2013.01); *C12N 9/88* (2013.01); *C12N 9/93* (2013.01); *C12N 15/52* (2013.01); *C12P 7/42* (2013.01); *C12Y 103/03* (2013.01); *C12Y 121/03007* (2015.07); *C12Y 203/01* (2013.01); *C12Y 205/01102* (2015.07); *C12Y 404/01026* (2015.07); *C12Y 602/01002* (2013.01)

(58) Field of Classification Search
CPC .... C12P 17/06; C12P 7/42; C12Y 404/01026; C12Y 203/01; C12Y 205/01102; C12Y 121/03007; C12Y 602/01002; C12Y 103/03; C12Y 203/01206; C12N 9/1085; C12N 9/0067; C12N 9/93; C12N 9/001; C12N 9/1029; C12N 9/88; C12N 1/12; C12N 15/52

See application file for complete search history.

(56) References Cited

U.S. PATENT DOCUMENTS

| | | |
|---|---|---|
| 7,883,882 B2 | 2/2011 | Franklin et al. |
| 7,935,515 B2 | 5/2011 | Franklin et al. |
| 8,187,860 B2 | 5/2012 | Franklin et al. |
| 8,222,010 B2 | 7/2012 | Franklin et al. |
| 8,268,610 B2 | 9/2012 | Franklin et al. |
| 8,435,767 B2 | 5/2013 | Franklin et al. |
| 8,592,188 B2 | 11/2013 | Franklin et al. |
| 8,633,012 B2 | 1/2014 | Franklin et al. |
| 8,674,180 B2 | 3/2014 | Franklin et al. |
| 8,697,427 B2 | 4/2014 | Franklin et al. |
| 8,765,424 B2 | 7/2014 | Franklin et al. |
| 8,772,575 B2 | 7/2014 | Franklin et al. |
| 8,846,375 B2 | 9/2014 | Franklin et al. |
| 8,852,885 B2 | 10/2014 | Franklin et al. |
| 8,945,908 B2 | 2/2015 | Franklin et al. |
| 8,951,777 B2 | 2/2015 | Franklin et al. |
| 9,062,294 B2 | 6/2015 | Franklin et al. |
| 9,066,527 B2 | 6/2015 | Franklin et al. |
| 9,068,213 B2 | 6/2015 | Franklin et al. |
| 9,102,973 B2 | 8/2015 | Franklin et al. |
| 9,109,239 B2 | 8/2015 | Franklin et al. |
| 9,200,307 B2 | 12/2015 | Franklin et al. |
| 9,249,436 B2 | 2/2016 | Franklin et al. |
| 9,249,441 B2 | 2/2016 | Franklin et al. |
| 9,255,282 B2 | 2/2016 | Franklin et al. |
| 9,279,136 B2 | 3/2016 | Franklin et al. |
| 9,290,749 B2 | 3/2016 | Rudenko et al. |
| 9,328,351 B2 | 5/2016 | Franklin et al. |
| 9,353,389 B2 | 5/2016 | Franklin et al. |
| 9,388,435 B2 | 7/2016 | Franklin et al. |
| 9,464,304 B2 | 10/2016 | Franklin et al. |
| 9,518,277 B2 | 12/2016 | Franklin et al. |
| 9,551,017 B2 | 1/2017 | Franklin et al. |
| 9,593,351 B2 | 3/2017 | Franklin et al. |
| 9,649,368 B2 | 5/2017 | Franklin et al. |

(Continued)

FOREIGN PATENT DOCUMENTS

| | | |
|---|---|---|
| EP | 3067058 A1 | 9/2016 |
| WO | WO 2006085672 | 8/2006 |
| WO | WO 2014159688 | 10/2014 |
| WO | WO 2017139496 | 8/2017 |

OTHER PUBLICATIONS

Sirikantaramas et al. The gene controlling marijuana psychoactivity: molecular cloning and heterologous expression of Delta1-tetrahydrocannabinolic acid synthase from *Cannabis sativa* L, JBC (2004), 279(38): 39767-74.*

(Continued)

*Primary Examiner* — Iqbal H Chowdhury
(74) *Attorney, Agent, or Firm* — HelixIP LLP

(57) ABSTRACT

In an aspect, the disclosure provides methods for making neurotransmitters in a host organism. The neurotransmitters can be cannabinoids and derivatives of cannabinoids. The host cells can be microalgae, fungi or other host cells. In a related aspect, the disclosure provides host cells engineered to have biochemical pathways for making neurotransmitters such as cannabinoids.

20 Claims, 4 Drawing Sheets

Specification includes a Sequence Listing.

(56) References Cited

U.S. PATENT DOCUMENTS

| | | | |
|---|---|---|---|
| 9,657,299 | B2 | 5/2017 | Franklin et al. |
| 9,719,114 | B2 | 8/2017 | Franklin et al. |
| 9,783,836 | B2 | 10/2017 | Rudenko et al. |
| 9,909,155 | B2 | 3/2018 | Franklin et al. |
| 9,969,990 | B2 | 5/2018 | Davis et al. |
| 10,006,034 | B2 | 6/2018 | Franklin et al. |
| 10,053,715 | B2 | 8/2018 | Franklin et al. |
| 10,100,341 | B2 | 10/2018 | Franklin et al. |
| 10,125,382 | B2 | 11/2018 | Casolari et al. |
| 10,167,489 | B2 | 1/2019 | Franklin et al. |
| 10,280,489 | B2 | 5/2019 | Dry et al. |
| 10,287,613 | B2 | 5/2019 | Franklin et al. |
| 10,316,299 | B2 | 6/2019 | Davis et al. |
| 10,344,305 | B2 | 7/2019 | Franklin et al. |
| 10,704,066 | B2 * | 7/2020 | Rudenko .................. C12N 1/12 |
| 2016/0289695 | A1 | 10/2016 | Franklin et al. |
| 2016/0298151 | A1 | 10/2016 | Butt et al. |
| 2021/0277431 | A1 * | 9/2021 | Rudenko .............. C12N 9/1029 |
| 2021/0285022 | A1 * | 9/2021 | Rudenko .............. C12N 9/1085 |
| 2021/0301309 | A1 * | 9/2021 | Rudenko ................ C12N 15/52 |
| 2021/0317491 | A1 * | 10/2021 | Rudenko .............. C12N 9/0067 |

OTHER PUBLICATIONS

Marks et al., Identification of candidate genes affecting delta-9-tetrahydro-cannabinol biosynthesis in Cannabis sativa, 2009, J Exp Biol vol. 60, pp. 3715-3726.

Day et al., Safety evaluation of a high lipid algal biomass from Chlorella protothecoides, 2009, Rewgul. Toxicol. Pharmcol. vol. 55, pp. 166-180.

* cited by examiner

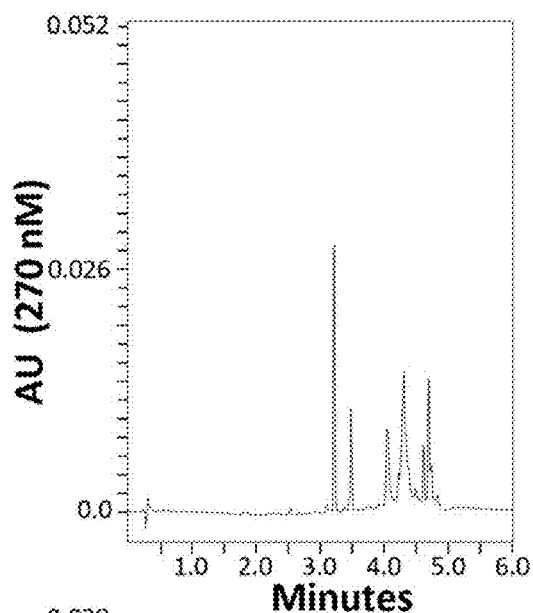
FIG.2A
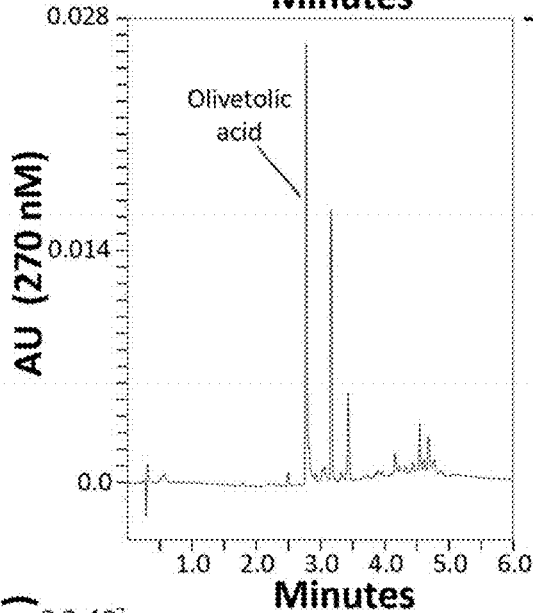
FIG.2B
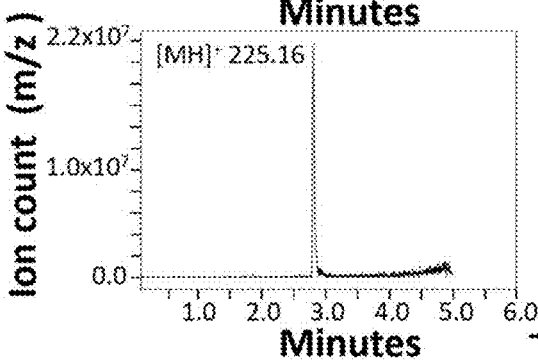
FIG.2C
FIG. 2

SEQUENCE LISTING

<160> NUMBER OF SEQ ID NOS: 17

<210> SEQ ID NO 1
<211> LENGTH: 720
<212> TYPE: PRT
<213> ORGANISM: Cannabis sativa

```
<400> SEQUENCE: 1

Met Gly Lys Asn Tyr Lys Ser Leu Asp Ser Val Ala Ser Asp Phe
1               5                   10                  15

Ile Ala Leu Gly Ile Thr Ser Glu Val Ala Glu Thr Leu His Gly Arg
            20                  25                  30

Leu Ala Glu Ile Val Cys Asn Tyr Gly Ala Ala Thr Pro Gln Thr Trp
        35                  40                  45

Ile Asn Ile Ala Asn His Ile Leu Ser Pro Asp Leu Pro Phe Ser Leu
    50                  55                  60

His Gln Met Leu Phe Tyr Gly Cys Tyr Lys Asp Phe Gly Pro Ala Pro
65                  70                  75                  80

Pro Ala Trp Ile Pro Asp Pro Glu Lys Val Lys Ser Thr Asn Leu Gly
                85                  90                  95

Ala Leu Leu Glu Lys Arg Gly Lys Glu Phe Leu Gly Val Lys Tyr Lys
            100                 105                 110

Asp Pro Ile Ser Ser Phe Ser His Phe Gln Glu Phe Ser Val Arg Asn
        115                 120                 125

Pro Glu Val Tyr Trp Arg Thr Val Leu Met Asp Glu Met Lys Ile Ser
    130                 135                 140

Phe Ser Lys Asp Pro Glu Cys Ile Leu Arg Arg Asp Asp Ile Asn Asn
145                 150                 155                 160

Pro Gly Gly Ser Glu Trp Leu Pro Gly Gly Tyr Leu Asn Ser Ala Lys
                165                 170                 175

Asn Cys Leu Asn Val Asn Ser Asn Lys Lys Leu Asn Asp Thr Met Ile
            180                 185                 190

Val Trp Arg Asp Glu Gly Asn Asp Asp Leu Pro Leu Asn Lys Leu Thr
        195                 200                 205

Leu Asp Gln Leu Arg Lys Arg Val Trp Leu Val Gly Tyr Ala Leu Glu
    210                 215                 220

Glu Met Gly Leu Glu Lys Gly Cys Ala Ile Ala Ile Asp Met Pro Met
225                 230                 235                 240

His Val Asp Ala Val Val Ile Tyr Leu Ala Ile Val Leu Ala Gly Tyr
                245                 250                 255

Val Val Val Ser Ile Ala Asp Ser Phe Ser Ala Pro Glu Ile Ser Thr
            260                 265                 270

Arg Leu Arg Leu Ser Lys Ala Lys Ala Ile Phe Thr Gln Asp His Ile
        275                 280                 285

Ile Arg Gly Lys Lys Arg Ile Pro Leu Tyr Ser Arg Val Val Glu Ala
    290                 295                 300

Lys Ser Pro Met Ala Ile Val Ile Pro Cys Ser Gly Ser Asn Ile Gly
305                 310                 315                 320

Ala Glu Leu Arg Asp Gly Asp Ile Ser Trp Asp Tyr Phe Leu Glu Arg
                325                 330                 335

Ala Lys Glu Phe Lys Asn Cys Glu Phe Thr Ala Arg Glu Gln Pro Val
            340                 345                 350

Asp Ala Tyr Thr Asn Ile Leu Phe Ser Ser Gly Thr Thr Gly Glu Pro
        355                 360                 365

Lys Ala Ile Pro Trp Thr Gln Ala Thr Pro Leu Lys Ala Ala Ala Asp
    370                 375                 380

Gly Trp Ser His Leu Asp Ile Arg Lys Gly Asp Val Ile Val Trp Pro
385                 390                 395                 400

Thr Asn Leu Gly Trp Met Met Gly Pro Trp Leu Val Tyr Ala Ser Leu
                405                 410                 415
```

```
Leu Asn Gly Ala Ser Ile Ala Leu Tyr Asn Gly Ser Pro Leu Val Ser
                420                 425                 430

Gly Phe Ala Lys Phe Val Gln Asp Ala Lys Val Thr Met Leu Gly Val
            435                 440                 445

Val Pro Ser Ile Val Arg Ser Trp Lys Ser Thr Asn Cys Val Ser Gly
450                 455                 460

Tyr Asp Trp Ser Thr Ile Arg Cys Phe Ser Ser Gly Glu Ala Ser
465                 470                 475                 480

Asn Val Asp Glu Tyr Leu Trp Leu Met Gly Arg Ala Asn Tyr Lys Pro
                485                 490                 495

Val Ile Glu Met Cys Gly Gly Thr Glu Ile Gly Gly Ala Phe Ser Ala
            500                 505                 510

Gly Ser Phe Leu Gln Ala Gln Ser Leu Ser Ser Phe Ser Gln Cys
515                 520                 525

Met Gly Cys Thr Leu Tyr Ile Leu Asp Lys Asn Gly Tyr Pro Met Pro
            530                 535                 540

Lys Asn Lys Pro Gly Ile Gly Glu Leu Ala Leu Gly Pro Val Met Phe
545                 550                 555                 560

Gly Ala Ser Lys Thr Leu Leu Asn Gly Asn His His Asp Val Tyr Phe
                565                 570                 575

Lys Gly Met Pro Thr Leu Asn Gly Glu Val Leu Arg Arg His Gly Asp
            580                 585                 590

Ile Phe Glu Leu Thr Ser Asn Gly Tyr Tyr His Ala His Gly Arg Ala
                595                 600                 605

Asp Asp Thr Met Asn Ile Gly Gly Ile Lys Ile Ser Ser Ile Glu Ile
610                 615                 620

Glu Arg Val Cys Asn Glu Val Asp Asp Arg Val Phe Glu Thr Thr Ala
625                 630                 635                 640

Ile Gly Val Pro Pro Leu Gly Gly Pro Glu Gln Leu Val Ile Phe
                645                 650                 655

Phe Val Leu Lys Asp Ser Asn Asp Thr Thr Ile Asp Leu Asn Gln Leu
                660                 665                 670

Arg Leu Ser Phe Asn Leu Gly Leu Gln Lys Lys Leu Asn Pro Leu Phe
            675                 680                 685

Lys Val Thr Arg Val Val Pro Leu Ser Ser Leu Pro Arg Thr Ala Thr
            690                 695                 700

Asn Lys Ile Met Arg Arg Val Leu Arg Gln Gln Phe Ser His Phe Glu
705                 710                 715                 720

<210> SEQ ID NO 2
<211> LENGTH: 385
<212> TYPE: PRT
<213> ORGANISM: Cannabis sativa

<400> SEQUENCE: 2

Met Asn His Leu Arg Ala Glu Gly Pro Ala Ser Val Leu Ala Ile Gly
1               5                   10                  15

Thr Ala Asn Pro Glu Asn Ile Leu Leu Gln Asp Glu Phe Pro Asp Tyr
                20                  25                  30

Tyr Phe Arg Val Thr Lys Ser Glu His Met Thr Gln Leu Lys Glu Lys
            35                  40                  45

Phe Arg Lys Ile Cys Asp Lys Ser Met Ile Arg Lys Arg Asn Cys Phe
        50                  55                  60

Leu Asn Glu Glu His Leu Lys Gln Asn Pro Arg Leu Val Glu His Glu
65                  70                  75                  80
```

```
Met Gln Thr Leu Asp Ala Arg Gln Asp Met Leu Val Glu Val Pro
                85                  90                  95

Lys Leu Gly Lys Asp Ala Cys Ala Lys Ala Ile Lys Glu Trp Gly Gln
            100                 105                 110

Pro Lys Ser Lys Ile Thr His Leu Ile Phe Thr Ser Ala Ser Thr Thr
            115                 120                 125

Asp Met Pro Gly Ala Asp Tyr His Cys Ala Lys Leu Leu Gly Leu Ser
130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Glu Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
290                 295                 300

Asp Lys Val Glu Glu Lys Leu His Leu Lys Ser Asp Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
        355                 360                 365

Pro Gly Leu Thr Val Glu Arg Val Val Arg Ser Val Pro Ile Lys
    370                 375                 380

Tyr
385

<210> SEQ ID NO 3
<211> LENGTH: 101
<212> TYPE: PRT
<213> ORGANISM: Cannabis sativa

<400> SEQUENCE: 3

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30

Ile Ile Pro Ala Met Lys Asp Val Tyr Trp Gly Lys Asp Val Thr Gln
        35                  40                  45

Lys Asn Lys Glu Glu Gly Tyr Thr His Ile Val Glu Val Thr Phe Glu
    50                  55                  60
```

```
Ser Val Glu Thr Ile Gln Asp Tyr Ile Ile His Pro Ala His Val Gly
 65                  70                  75                  80

Phe Gly Asp Val Tyr Arg Ser Phe Trp Glu Lys Leu Leu Ile Phe Asp
                 85                  90                  95

Tyr Thr Pro Arg Lys
            100

<210> SEQ ID NO 4
<211> LENGTH: 395
<212> TYPE: PRT
<213> ORGANISM: Cannabis sativa

<400> SEQUENCE: 4

Met Gly Leu Ser Ser Val Cys Thr Phe Ser Phe Gln Thr Asn Tyr His
  1               5                  10                  15

Thr Leu Leu Asn Pro His Asn Asn Pro Lys Thr Ser Leu Leu Cys
                 20                  25                  30

Tyr Arg His Pro Lys Thr Pro Ile Lys Tyr Ser Tyr Asn Asn Phe Pro
                 35                  40                  45

Ser Lys His Cys Ser Thr Lys Ser Phe His Leu Gln Asn Lys Cys Ser
 50                  55                  60

Glu Ser Leu Ser Ile Ala Lys Asn Ser Ile Arg Ala Ala Thr Thr Asn
 65                  70                  75                  80

Gln Thr Glu Pro Pro Glu Ser Asp Asn His Ser Val Ala Thr Lys Ile
                 85                  90                  95

Leu Asn Phe Gly Lys Ala Cys Trp Lys Leu Gln Arg Pro Tyr Thr Ile
                100                 105                 110

Ile Ala Phe Thr Ser Cys Ala Cys Gly Leu Phe Gly Lys Glu Leu Leu
                115                 120                 125

His Asn Thr Asn Leu Ile Ser Trp Ser Leu Met Phe Lys Ala Phe Phe
            130                 135                 140

Phe Leu Val Ala Ile Leu Cys Ile Ala Ser Phe Thr Thr Thr Ile Asn
145                 150                 155                 160

Gln Ile Tyr Asp Leu His Ile Asp Arg Ile Asn Lys Pro Asp Leu Pro
                165                 170                 175

Leu Ala Ser Gly Glu Ile Ser Val Asn Thr Ala Trp Ile Met Ser Ile
                180                 185                 190

Ile Val Ala Leu Phe Gly Leu Ile Ile Thr Ile Lys Met Lys Gly Gly
            195                 200                 205

Pro Leu Tyr Ile Phe Gly Tyr Cys Phe Gly Ile Phe Gly Gly Ile Val
            210                 215                 220

Tyr Ser Val Pro Pro Phe Arg Trp Lys Gln Asn Pro Ser Thr Ala Phe
225                 230                 235                 240

Leu Leu Asn Phe Leu Ala His Ile Ile Thr Asn Phe Thr Phe Tyr Tyr
                245                 250                 255

Ala Ser Arg Ala Ala Leu Gly Leu Pro Phe Glu Leu Arg Pro Ser Phe
                260                 265                 270

Thr Phe Leu Leu Ala Phe Met Lys Ser Met Gly Ser Ala Leu Ala Leu
            275                 280                 285

Ile Lys Asp Ala Ser Asp Val Glu Gly Asp Thr Lys Phe Gly Ile Ser
            290                 295                 300

Thr Leu Ala Ser Lys Tyr Gly Ser Arg Asn Leu Thr Leu Phe Cys Ser
305                 310                 315                 320

Gly Ile Val Leu Leu Ser Tyr Val Ala Ala Ile Leu Ala Gly Ile Ile
                325                 330                 335
```

```
Trp Pro Gln Ala Phe Asn Ser Asn Val Met Leu Leu Ser His Ala Ile
                340                 345                 350

Leu Ala Phe Trp Leu Ile Leu Gln Thr Arg Asp Phe Ala Leu Thr Asn
            355                 360                 365

Tyr Asp Pro Glu Ala Gly Arg Arg Phe Tyr Glu Phe Met Trp Lys Leu
        370                 375                 380

Tyr Tyr Ala Glu Tyr Leu Val Tyr Val Phe Ile
385                 390                 395

<210> SEQ ID NO 5
<211> LENGTH: 545
<212> TYPE: PRT
<213> ORGANISM: Cannabis sativa

<400> SEQUENCE: 5

Met Asn Cys Ser Thr Phe Ser Phe Trp Phe Val Cys Lys Ile Ile Phe
1               5                   10                  15

Phe Phe Leu Ser Phe Asn Ile Gln Ile Ser Ile Ala Asn Pro Gln Glu
            20                  25                  30

Asn Phe Leu Lys Cys Phe Ser Glu Tyr Ile Pro Asn Asn Pro Ala Asn
            35                  40                  45

Pro Lys Phe Ile Tyr Thr Gln His Asp Gln Leu Tyr Met Ser Val Leu
        50                  55                  60

Asn Ser Thr Ile Gln Asn Leu Arg Phe Thr Ser Asp Thr Thr Pro Lys
65                  70                  75                  80

Pro Leu Val Ile Val Thr Pro Ser Asn Val Ser His Ile Gln Ala Ser
                85                  90                  95

Ile Leu Cys Ser Lys Lys Val Gly Leu Gln Ile Arg Thr Arg Ser Gly
            100                 105                 110

Gly His Asp Ala Glu Gly Leu Ser Tyr Ile Ser Gln Val Pro Phe Ala
        115                 120                 125

Ile Val Asp Leu Arg Asn Met His Thr Val Lys Val Asp Ile His Ser
130                 135                 140

Gln Thr Ala Trp Val Glu Ala Gly Ala Thr Leu Gly Glu Val Tyr Tyr
145                 150                 155                 160

Trp Ile Asn Glu Met Asn Glu Asn Phe Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
210                 215                 220

Asp Leu Phe Trp Ala Ile Arg Gly Gly Gly Gly Glu Asn Phe Gly Ile
225                 230                 235                 240

Ile Ala Ala Cys Lys Ile Lys Leu Val Val Val Pro Ser Lys Ala Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Met
        275                 280                 285

Leu Thr Thr His Phe Arg Thr Arg Asn Ile Thr Asp Asn His Gly Lys
290                 295                 300

Asn Lys Thr Thr Val His Gly Tyr Phe Ser Ser Ile Phe Leu Gly Gly
305                 310                 315                 320
```

```
Val Asp Ser Leu Val Asp Leu Met Asn Lys Ser Phe Pro Glu Leu Gly
            325                 330                 335

Ile Lys Lys Thr Asp Cys Lys Glu Leu Ser Trp Ile Thr Thr Ile
        340                 345                 350

Phe Tyr Ser Gly Val Val Asn Tyr Asn Thr Ala Asn Phe Lys Lys Glu
            355                 360                 365

Ile Leu Leu Asp Arg Ser Ala Gly Lys Lys Thr Ala Phe Ser Ile Lys
        370                 375                 380

Leu Asp Tyr Val Lys Lys Leu Ile Pro Glu Thr Ala Met Val Lys Ile
385                 390                 395                 400

Leu Glu Lys Leu Tyr Glu Glu Val Gly Val Gly Met Tyr Val Leu
            405                 410                 415

Tyr Pro Tyr Gly Gly Ile Met Asp Glu Ile Ser Glu Ser Ala Ile Pro
            420                 425                 430

Phe Pro His Arg Ala Gly Ile Met Tyr Glu Leu Trp Tyr Thr Ala Thr
            435                 440                 445

Trp Glu Lys Gln Glu Asp Asn Glu Lys His Ile Asn Trp Val Arg Ser
            450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn Pro Glu Ser
                485                 490                 495

Pro Asn Asn Tyr Thr Gln Ala Arg Ile Trp Gly Glu Lys Tyr Phe Gly
            500                 505                 510

Lys Asn Phe Asn Arg Leu Val Lys Val Lys Thr Lys Ala Asp Pro Asn
            515                 520                 525

Asn Phe Phe Arg Asn Glu Gln Ser Ile Pro Pro Leu Pro Pro Arg His
            530                 535                 540

His
545

<210> SEQ ID NO 6
<211> LENGTH: 544
<212> TYPE: PRT
<213> ORGANISM: Cannabis sativa

<400> SEQUENCE: 6

Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu
            20                  25                  30

Asn Phe Leu Lys Cys Phe Ser Gln Tyr Ile Pro Asn Asn Ala Thr Asn
        35                  40                  45

Leu Lys Leu Val Tyr Thr Gln Asn Asn Pro Leu Tyr Met Ser Val Leu
50                  55                  60

Asn Ser Thr Ile His Asn Leu Arg Phe Thr Ser Asp Thr Thr Pro Lys
65                  70                  75                  80

Pro Leu Val Ile Val Thr Pro Ser His Val Ser His Ile Gln Gly Thr
                85                  90                  95

Ile Leu Cys Ser Lys Lys Val Gly Leu Gln Ile Arg Thr Arg Ser Gly
            100                 105                 110

Gly His Asp Ser Glu Gly Met Ser Tyr Ile Ser Gln Val Pro Phe Val
        115                 120                 125

Ile Val Asp Leu Arg Asn Met Arg Ser Ile Lys Ile Asp Val His Ser
130                 135                 140
```

-continued

```
Gln Thr Ala Trp Val Glu Ala Gly Ala Thr Leu Gly Glu Val Tyr Tyr
145                 150                 155                 160

Trp Val Asn Glu Lys Asn Glu Asn Leu Ser Leu Ala Ala Gly Tyr Cys
                165                 170                 175

Pro Thr Val Cys Ala Gly Gly His Phe Gly Gly Gly Tyr Gly Pro
                180                 185                 190

Leu Met Arg Asn Tyr Gly Leu Ala Ala Asp Asn Ile Ile Asp Ala His
                195                 200                 205

Leu Val Asn Val His Gly Lys Val Leu Asp Arg Lys Ser Met Gly Glu
                210                 215                 220

Asp Leu Phe Trp Ala Leu Arg Gly Gly Ala Glu Ser Phe Gly Ile
225                 230                 235                 240

Ile Val Ala Trp Lys Ile Arg Leu Val Ala Val Pro Lys Ser Thr Met
                245                 250                 255

Phe Ser Val Lys Lys Ile Met Glu Ile His Glu Leu Val Lys Leu Val
                260                 265                 270

Asn Lys Trp Gln Asn Ile Ala Tyr Lys Tyr Asp Lys Asp Leu Leu Leu
                275                 280                 285

Met Thr His Phe Ile Thr Arg Asn Ile Thr Asp Asn Gln Gly Lys Asn
                290                 295                 300

Lys Thr Ala Ile His Thr Tyr Phe Ser Ser Val Phe Leu Gly Gly Val
305                 310                 315                 320

Asp Ser Leu Val Asp Leu Met Asn Lys Ser Phe Pro Glu Leu Gly Ile
                325                 330                 335

Lys Lys Thr Asp Cys Arg Gln Leu Ser Trp Ile Asp Thr Ile Ile Phe
                340                 345                 350

Tyr Ser Gly Val Val Asn Tyr Asp Thr Asp Asn Phe Asn Lys Glu Ile
                355                 360                 365

Leu Leu Asp Arg Ser Ala Gly Gln Asn Gly Ala Phe Lys Ile Lys Leu
                370                 375                 380

Asp Tyr Val Lys Lys Pro Ile Pro Glu Ser Val Phe Val Gln Ile Leu
385                 390                 395                 400

Glu Lys Leu Tyr Glu Glu Asp Ile Gly Ala Gly Met Tyr Ala Leu Tyr
                405                 410                 415

Pro Tyr Gly Gly Ile Met Asp Glu Ile Ser Glu Ser Ala Ile Pro Phe
                420                 425                 430

Pro His Arg Ala Gly Ile Leu Tyr Glu Leu Trp Tyr Ile Cys Ser Trp
                435                 440                 445

Glu Lys Gln Glu Asp Asn Glu Lys His Leu Asn Trp Ile Arg Asn Ile
450                 455                 460

Tyr Asn Phe Met Thr Pro Tyr Val Ser Lys Asn Pro Arg Leu Ala Tyr
465                 470                 475                 480

Leu Asn Tyr Arg Asp Leu Asp Ile Gly Ile Asn Asp Pro Lys Asn Pro
                485                 490                 495

Asn Asn Tyr Thr Gln Ala Arg Ile Trp Gly Glu Lys Tyr Phe Gly Lys
                500                 505                 510

Asn Phe Asp Arg Leu Val Lys Val Lys Thr Leu Val Asp Pro Asn Asn
                515                 520                 525

Phe Phe Arg Asn Glu Gln Ser Ile Pro Pro Leu Pro Arg His Arg His
530                 535                 540
```

<210> SEQ ID NO 7
<211> LENGTH: 545
<212> TYPE: PRT
<213> ORGANISM: Cannabis sativa

<400> SEQUENCE: 7

```
Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
            20                  25                  30

Asn Phe Leu Lys Cys Phe Ser Lys His Ile Pro Asn Asn Val Ala Asn
        35                  40                  45

Pro Lys Leu Val Tyr Thr Gln His Asp Gln Leu Tyr Met Ser Ile Leu
    50                  55                  60

Asn Ser Thr Ile Gln Asn Leu Arg Phe Ile Ser Asp Thr Thr Pro Lys
65                  70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Gly Glu Asn Phe Gly Ile
225                 230                 235                 240

Ile Ala Ala Trp Lys Ile Lys Leu Val Ala Val Pro Ser Lys Ser Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
    290                 295                 300

Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Phe Ser Trp Ile Asp Thr Thr Ile
            340                 345                 350

Phe Tyr Ser Gly Val Val Asn Phe Asn Thr Ala Asn Phe Lys Lys Glu
        355                 360                 365

Ile Leu Leu Asp Arg Ser Ala Gly Lys Lys Thr Ala Phe Ser Ile Lys
    370                 375                 380
```

```
Leu Asp Tyr Val Lys Lys Pro Ile Pro Glu Thr Ala Met Val Lys Ile
385                 390                 395                 400

Leu Glu Lys Leu Tyr Glu Glu Asp Val Gly Ala Gly Met Tyr Val Leu
            405                 410                 415

Tyr Pro Tyr Gly Gly Ile Met Glu Glu Ile Ser Glu Ser Ala Ile Pro
        420                 425                 430

Phe Pro His Arg Ala Gly Ile Met Tyr Glu Leu Trp Tyr Thr Ala Ser
    435                 440                 445

Trp Glu Lys Gln Glu Asp Asn Glu Lys His Ile Asn Trp Val Arg Ser
450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn His Ala Ser
            485                 490                 495

Pro Asn Asn Tyr Thr Gln Ala Arg Ile Trp Gly Glu Lys Tyr Phe Gly
        500                 505                 510

Lys Asn Phe Asn Arg Leu Val Lys Val Lys Thr Lys Val Asp Pro Asn
    515                 520                 525

Asn Phe Phe Arg Asn Glu Gln Ser Ile Pro Pro Leu Pro Pro His His
530                 535                 540

His
545

<210> SEQ ID NO 8
<211> LENGTH: 10072
<212> TYPE: DNA
<213> ORGANISM: Artificial Sequence
<220> FEATURE:
<223> OTHER INFORMATION: Plasmid pUR17001

<400> SEQUENCE: 8
agcccgcacc ctcgttgatc tgggagccct gcgcagcccc ttaaatcatc tcagtcaggt      60
ttctgtgttc aactgagcct aaagggcttt cgtcatgcgc acgagcacac gtatatcggc     120
cacgcagttt ctcaaaagcg gtagaacagt tcgcgagccc tcgtaggtcg aaaacttgcg     180
ccagtactat taaattaaat taattgatcg aacgagacgc gaaacttttg cagaatgcca     240
ccgagtttgc ccagagaatg ggagtggcgc cattcaccat ccgcctgtgc ccggcttgat     300
tcgccgagac gatggacggc gagaccaggg agcggcttgc gagccccgag ccggtagcag     360
gaacaatgat cgacaatctt cctgtccaat tactggcaac cattagaaag agccggagcg     420
cgttgaaagt ctgcaatcga gtaatttttc gatacgtcgg gcctgctgaa ccctaaggct     480
ccggactttg tttaaggcga tccaagatgc acgcggcccc aggcacgtat ctcaagcaca     540
aaccccagcc ttagtttcga ctttgggaga tagcgaccga tatctagt ttggcatttt       600 gtatattaat tacctcaagc aatggagcgc tctgatgcgg tgcagcgtcg gctgcagcac     660
ctggcagtgg cgctagggtc gccctatcgc tcggaacctg gtcagctggc tcccgcctcc     720
tgctcagcct cttccggtac cctttcttgc gctatgacac ttccagcaaa aggtagggcg     780
ggctgcgaga cggcttcccg gcgctgcatg caacaccgat gatgcttcga ccccccgaag     840
ctccttcggg gctgcatggg cgctccgatg ccgctccagg gcgagcgctg tttaaatagc     900
caggcccccg attgcaaaga cattatagcg agctaccaaa gccatattca aacacctaga     960
tcactaccac ttctacacag gccactccgag cttgtgatcg cactccgcta agggggcgcc    1020
tcttcctctt cgtttcagtc acaacccgca acggcgcgc catgatcgag caggacggcc     1080
```

-continued

```
tccacgccgg ctcccccgcc gcctgggtgg agcgcctgtt cggctacgac tgggcccagc    1140
agaccatcgg ctgctccgac gccgccgtgt tccgcctgtc cgcccagggc cgccccgtgc    1200
tgttcgtgaa gaccgacctg tccggcgccc tgaacgagct gcaggacgag gccgcccgcc    1260
tgtcctggct ggccaccacc ggcgtgccct cgccgccgt gctggacgtg gtgaccgagg     1320
ccggccgcga ctggctgctg ctgggcgagg tgcccggcca ggacctgctg tcctcccacc    1380
tggcccccgc cgagaaggtg tccatcatgg ccgacgccat cgccgcctg cacacccctgg    1440 accccgccac ctgccccttc gaccaccagg ccaagcaccg catcgagcgc gcccgcaccc    1500
gcatggaggc cggcctggtg gaccaggacg acctggacga ggagcaccag ggcctggccc    1560
ccgccgagct gttcgcccgc ctgaaggccc gcatgcccga cggcgaggac ctggtggtga    1620
cccacggcga cgcctgcctg cccaacatca tggtggagaa cggccgcttc tccggcttca    1680
tcgactgcgg ccgcctgggc gtggccgacc gctaccagga catcgccctg ccacccgcg    1740 acatcgccga ggagctgggc ggcgagtggg ccgaccgctt cctggtgctg tacggcatcg    1800
ccgcccccga ctcccagcgc atcgccttct accgcctgct ggacgagttc ttctgatgac    1860
aattgacgcc cgcgcggcgc acctgacctg ttctctcgag ggcgcctgtt ctgccttgcg    1920
aaacaagccc ctggagcatg cgtgcatgat cgtctctggc gccccgccgc gcggtttgtc    1980
gccctcgcgg gcgccgcggc gcggggggcg cattgaaatt gttgcaaacc ccacctgaca    2040
gattgagggc ccaggcagga aggcgttgag atggaggtac aggagtcaag taactgaaag    2100 ttttttatgat aactaacaac aaagggtcgt ttctggccag cgaatgacaa gaacaagatt    2160
ccacatttcc gtgtagaggc ttgccatcga atgtgagcgg gcgggccgcg acccgacaa    2220 aacccttacg acgtggtaag aaaaacgtgg cgggcactgt ccctgtagcc tgaagaccag    2280
caggagacga tcggaagcat cacagcacag gatcgtagag ctggatccat cgcctgctca    2340
agcgggcgct caacatgcag agcgtcagcg agacgggctg tggcgatcgc gagacggacg    2400
aggccgcctc tgcccgtgtt tgaactgagcg tcagcgctgg ctaaggggag ggagactcat    2460
ccccaggctc gcgccagggc tctgatcccg tctcgggcgg tgatcggcgc gcatgactac    2520
gacccaacga cgtacgagac tgatgtcggt cccgacgagg agcgccgcga ggcactcccg    2580
ggccaccgac catgtttaca ccgaccgaaa gcactcgctc gtatccattc cgtgcgcccg    2640
cacatgcatc atcttttggt accgacttcg gtcttgtttt accctacga cctgccttcc    2700 aaggtgtgag caactcgccc ggacatgacc gagggtgatc atccggatcc caggccca    2760 gcagcccctg ccagaatggc tcgcgctttc cagcctgcag gcccgtctcc caggtcgacg    2820
caacctacat gaccacccca atctgtccca gaccccaaac accctccttc cctgcttctc    2880
tgtgatcgct gatcagcaac aactagtaac aatgggcaag aactacaagt ccctggactc    2940
cgtcgtcgcc tccgacttca tcgccctggg catcacctcc gaggtcgcgg agacgctgca    3000
cggccgcctg gcggagatcg tgtgcaacta cggcgcggcc acccccccaga cgtggatcaa    3060 catcgccaac cacatcctgt cccccgacct gcccttctcc ctgcaccaga tgctgttcta    3120
cggctgctac aaggacttcg gccccgcccc cccgcgtgg atccccgacc ccgagaaggt    3180
gaagtccacc aacctgggcg cgctgctgga agcgcggcg aaggagttcc tgggcgtgaa    3240
gtacaaggac cccatctcct ccttctccca cttccaggag ttctccgtgc gcaaccccga    3300
ggtgtactgg cgcaccgtcc tgatggacga gatgaagatc tccttctcca aggacccga    3360 gtgcatcctg cgccgcgacg acatcaacaa ccccggcggc tccgagtggc tgcccggcgg    3420
ctacctgaac tccgccaaga actgcctgaa cgtgaactcc aacaagaagc tgaacgacac    3480
```

```
catgatcgtc tggcgcgacg agggcaacga cgacctgccc ctgaacaagc tgacgctgga      3540
ccagctgcgc aagcgcgtgt ggctggtggg ctacgcgctg gaggagatgg gcctggagaa      3600
gggctgcgcc atcgcgatcg acatgcccat gcacgtggac gcggtcgtga tctacctggc      3660
catcgtgctg gcgggctacg tggtggtgtc catcgccgac tccttctccg cccccgagat      3720
ctccacgcgc ctgcgcctgt ccaaggcgaa ggcgatcttc acccaggacc acatcatccg      3780
cggcaagaag cgcatccccc tgtactcccg cgtggtggag gccaagtccc ccatggccat      3840
cgtcatcccc tgctccggct ccaacatcgg cgccgagctg cgcgacggcg acatctcctg      3900
ggactacttc ctggagcgcg ccaaggagtt caagaactgc gagttcaccg cgcgcgagca      3960
gcccgtggac gcctacacca acatcctgtt ctcctccggc accacgggcg agcccaaggc      4020
catcccctgg acgcaggcca cccccctgaa ggcggcggcg acggctggt cccacctgga       4080 catccgcaag ggcgacgtga tcgtgtggcc cacgaacctg gctggatga tgggcccctg      4140 gctggtgtac gcgtccctgc tgaacggcgc gtccatcgcc ctgtacaacg gctccccct      4200 ggtgtccggc ttcgccaagt tcgtccagga cgcgaaggtc accatgctgg gcgtggtgcc      4260
ctccatcgtg cgctcctgga agtccacgaa ctgcgtgtcc ggctacgact ggtccacgat      4320
ccgctgcttc tcctcctccg gcgaggcctc caacgtggac gagtacctgt ggctgatggg      4380
ccgcgcgaac tacaagcccg tcatcgagat gtgcggcggc accgagatcg cggcgcgtt       4440 ctccgcgggc tccttcctgc aggcgcagtc cctgtcctcc ttctcctccc agtgcatggg      4500
ctgcacgctg tacatcctgg acaagaacgg ctaccccatg cccaagaaca gcccggcat       4560 cggcgagctg gccctgggcc ccgtgatgtt cggcgcctcc aagacgctgc tgaacggcaa      4620
ccaccacgac gtgtacttca agggcatgcc caccctgaac ggcgaggtgc tgcgccgcca      4680
cggcgacatc ttcgagctga cctccaacgg ctactaccac gcgcacggcc gcgcggacga      4740
cacgatgaac atcggcggca tcaagatctc ctccatcgag atcgagcgcg tctgcaacga      4800 ggtgacgac cgcgtgttcg agacgaccgc gatcggcgtg ccccccctgg gcggcggccc      4860
cgagcagctg gtcatcttct tcgtcctgaa ggactccaac gacacgacca tcgacctgaa      4920
ccagctgcgc ctgtccttca acctgggcct gcagaagaag ctgaaccccc tgttcaaggt      4980
cacgcgcgtg gtccccctgt cctccctgcc ccgcacggcc accaacaaga tcatgcgccg      5040
cgtgctgcgc cagcagttct cccacttcga gtgatatcga gacagacgac cttggcaggc      5100
gtcgggtagg gaggtggtgg tgatggcgtc tcgatgccat cgcacgcatc caacgaccgt      5160
atacgcatcg tccaatgacc gtcggtgtcc tctctgcctc cgttttgtga gatgtctcag      5220
gcttggtgca tcctcgggtg ccagccacg ttgcgcgtcg tgctgcttgc ctctcttgcg       5280
cctctgtggt actggaaaat atcatcgagg cccgtttttt tgctcccatt tcctttccgc      5340
tacatcttga aagcaaacga caaacgaagc agcaagcaaa gagcacgagg acggtgaaca      5400
agtctgtcac ctgtatacat ctatttcccc gcgggtgcac ctactctctc tcctgccccg      5460
gcagagtcag ctgccttacg tgacgaagct tgtgaaaact cgctcgaccg cccgcgtccc      5520
gcaggcagcg atgacgtgtg cgtgacctgg gtgtttcgtc gaaaggccag caaccccaaa      5580
tcgcaggcga tccggagatt gggatctgat ccgagcttgg accagatccc ccacgatgcg      5640
gcacgggaac tgcatcgact cggcgcggaa cccagctttc gtaaatgcca gattggtgtc      5700
cgataccttg atttgccatc agcgaaacaa gacttcagca gcgagcgtat ttggcgggcg      5760
tgctaccagg gttgcataca ttgcccattt ctgtctggac cgctttaccg gcgcagaggg      5820
tgagttgatg gggttggcag gcatcgaaac gcgcgtgcat ggtgtgtgtg tctgttttcg      5880
```

-continued

```
gctgcacaat ttcaatagtc ggatgggcga cggtagaatt gggtgttgcg ctcgcgtgca    5940
tgcctcgccc cgtcgggtgt catgaccggg actggaatcc cccctcgcga ccctcctgct    6000
aacgctcccg actctcccgc ccgcgcgcag gatagactct agttcaacca atcgacaatg    6060
gccgtcaagc acctgatcgt gctgaagttc aaggacgaga tcaccgaggc gcagaaggag    6120
gagttcttca agacctacgt gaacctggtc aacatcatcc ccgcgatgaa ggacgtgtac    6180
tggggcaagg acgtgaccca agaacaag gaggagggct acacgcacat cgtgagtgtg     6240
acgttcgagt ccgtcgagac gatccaggac tacatcatcc accccgcgca cgtcggcttc    6300
ggcgacgtgt accgctcctt ctgggagaag ctgctgatct tcgactacac cccccgcaag    6360
tgattaatta actcgaggca gcagcagctc ggatagtatc gacacactct ggacgctggt    6420
cgtgtgatgg actgttgccg ccacacttgc tgccttgacc tgtgaatatc cctgccgctt    6480
ttatcaaaca gcctcagtgt gtttgatctt gtgtgtacgc gcttttgcga gttgctagct    6540
gcttgtgcta tttgcgaata ccaccccag catcccttc cctcgtttca tatcgcttgc      6600
atcccaaccg caacttatct acgctgtcct gctatccctc agcgctgctc ctgctcctgc    6660
tcactgcccc tcgcacagcc ttggtttggg ctccgcctgt attctcctgg tactgcaacc    6720
tgtaaaccag cactgcaatg ctgatgcacg ggaagtagtg ggatgggaac acaaatggaa    6780
agctgtaggc cgacaggacg cgcgtcaaag gtgctggtcg tgtatgccct ggccggcagg    6840
tcgttgctgc tgctggttag tgattccgca accctgattt tggcgtctta ttttggcgtg    6900
gcaaacgctg gcgcccgcga ccgggccgg cggcgatgcg gtgccccacg gctgccggaa    6960
tccaagggag gcaagagcgc ccgggtcagt tgaagggctt tacgcgcaag gtacagccgc    7020
tcctgcaagg ctgcgtggtg gaattggacg tgcaggtcct gctgaagttc ctccaccgcc    7080
tcaccagcgg acaaagcacc ggtgtatcag gtccgtgtca tccactctaa gaactcgac     7140
tacgacctac tgatggccct agattcttca tcaaaaacgc ctgagacact tgcccaggat    7200
tgaaactccc tgaagggacc accagggcc ctgagttgtt ccttcccccc gtggcgagct     7260
gccagccagg ctgtacctgt gatcgaggct ggcgggaaaa taggcttcgt gtgctcaggt    7320
catgggaggt gcaggacagc tcatgaaacg ccaacaatcg cacaattcat gtcaagctaa    7380
tcagctattt cctcttcacg agctgtaatt gtcccaaaat tctggtctac cgggggtgat    7440
ccttcgtgta cgggccttc cctcaaccct aggtatgcgc gcatgcggtc gccgcgcaac    7500
tcgcgcgagg gccgagggtt tgggacgggc cgtcccgaaa tgcagttgca cccggatgcg    7560
tggcacctt tttgcgataa tttatgcaat ggactgctct gcaaaattct ggctctgtcg     7620
ccaaccctag gatcagcggc gtaggatttc gtaatcattc gtcctgatgg ggagctaccg    7680
actaccctaa tatcagcccg actgcctgac gccagcgtcc acttttgtgc acacattcca    7740
ttcgtgccca agacatttca ttgtggtgcg aagcgtcccc agttacgctc acctgtttcc    7800
cgacctcctt actgttctgt cgacagagcg ggcccacagg ccggtcgcag ccactagtat    7860
gaaccacctg cgcgccgagg gccccgcgtc cgtcctggcc atcggcacgg ccaaccccga    7920
gaacatcctg ctgcaggacg agttccccga ctactactc cgcgtgacca gtccgagca     7980
catgacccag ctgaaggaga agttccgcaa gatctgcgac aagtccatga tccgcaagcg    8040
caactgcttc ctgaacgagg agcacctgaa gcagaaccc cgcctggtgg agcacgagat    8100
gcagaccctg gacgcccgcc aggacatgct ggtcgtcgag gtgcccaagc tgggcaagga    8160
cgcctgcgcg aagcgatca aggagtgggg ccagcccaag tccaagatca cccacctgat    8220
cttcacgtcc gcctccacca ccgacatgcc cggcgcggac taccactgcg ccaagctgct    8280
```

| | | | | | |
|---|---|---|---|---|---|
| gggcctgtcc | ccctccgtga | agcgcgtcat | gatgtaccag | ctgggctgct | acggcggcgg | 8340 |
| cacggtgctg | cgcatcgcca | aggacatcgc | cgagaacaac | aagggcgcgc | gcgtcctggc | 8400 |
| cgtctgctgc | gacatcatgg | cctgcctgtt | ccgcggcccc | tccgagtccg | acctggagct | 8460 |
| gctggtgggc | caggccatct | tcggcgacgg | cgccgccgcg | gtcatcgtgg | gcgcggagcc | 8520 |
| cgacgagtcc | gtcggcgagc | gccccatctt | cgagctggtg | tccaccggcc | agacgatcct | 8580 |
| gcccaactcc | gagggcacga | tcggcggcca | catccgcgag | gcgggcctga | tcttcgacct | 8640 |
| gcacaaggac | gtgcccatgc | tgatctccaa | caacatcgag | aagtgcctga | tcgaggcgtt | 8700 |
| caccccatc | ggcatctccg | actggaactc | catcttctgg | atcacgcacc | ccggcggcaa | 8760 |
| ggccatcctg | gacaaggtgg | aggagaagct | gcacctgaag | tccgacaagt | tcgtggactc | 8820 |
| ccgccacgtg | ctgtccgagc | acggcaacat | gtcctcctcc | acggtgctgt | tcgtcatgga | 8880 |
| cgagctgcgc | aagcgctccc | tggaggaggg | caagtccacc | accggcgacg | gcttcgagtg | 8940 |
| gggcgtgctg | ttcggcttcg | gccccggcct | gaccgtcgag | cgcgtcgtcg | tgcgctccgt | 9000 |
| ccccatcaag | tactgattaa | ttaactcgag | acgcccgcgc | ggcgcacctg | acctgttctc | 9060 |
| tcgagggcgc | ctgttctgcc | ttgcgaaaca | agcccctgga | gcatgcgtgc | atgatcgtct | 9120 |
| ctggcgcccc | gccgcgcggt | tgtcgccct | cgcgggcgcc | gcggccgcgg | gggcgcattg | 9180 |
| aaattgttgc | aaaccccacc | tgacagattg | agggcccagg | caggaaggcg | ttgagatgga | 9240 |
| ggtacaggag | tcaagtaact | gaaagttttt | atgataacta | acaacaaagg | gtcgtttctg | 9300 |
| gccagcgaat | gacaagaaca | agattccaca | tttccgtgta | gaggcttgcc | atcgaatgtg | 9360 |
| agcgggcggg | ccgcggaccc | gacaaaaccc | ttacgacgtg | gtaagaaaaa | cgtggcgggc | 9420 |
| actgtccctg | tagcctgaag | accagcagga | gacgatcgga | agcatcacag | cacaatgagc | 9480 |
| tcagccgtag | cgtctgcgtg | ttgggagctg | gagtcgtggg | cttgacgacg | gcgctgcagc | 9540 |
| tgttgcagga | tgtgcctggc | gtgcgcgttc | acgtcgtggc | tgagaaatat | ggcgacgaaa | 9600 |
| cgttgacggc | tggggccggc | gggctgtgga | tgccatacgc | attgggtacg | cggccattgg | 9660 |
| atgggattga | taggcttatg | gagggataat | agagtttttg | ccggatccaa | cgcatgtgga | 9720 |
| tgcggtatcc | cggtgggctg | aaagtgtgga | aggatagtgc | attggctatt | cacatgcact | 9780 |
| gcccaccct | tttggcagga | aatgtgccgg | catcgttggt | gcaccgatgg | ggaaaatcga | 9840 |
| cgttcgacca | ctacatgaag | atttatacgt | ctgaagatgc | agcgactgcg | ggtgcgaaac | 9900 |
| ggatgacggt | ttggtcgtgt | atgtcacagc | atgtgctgga | tcttgcgggc | taactccccc | 9960 |
| tgccacggcc | cattgcaggt | gtcatgttga | ctggagggta | cgacctttcg | tccgtcaaat | 10020 |
| tcccagagga | ggaccccgctc | tgggccgaca | ttgtgcccac | ttttcgccgc | ct | 10072 |

<210> SEQ ID NO 9
<211> LENGTH: 6542
<212> TYPE: DNA
<213> ORGANISM: Artificial Sequence
<220> FEATURE:
<223> OTHER INFORMATION: Plasmid pUR17002

<400> SEQUENCE: 9

| | | | | | |
|---|---|---|---|---|---|
| aacggaggtc | tgtcaccaaa | tggacccegt | ctattgcggg | aaaccacggc | gatggcacgt | 60 |
| ttcaaaactt | gatgaaatac | aatattcagt | atgtcgcggg | cggcgacggc | ggggagctga | 120 |
| tgtcgcgctg | ggtattgctt | aatcgccagc | ttcgcccccg | tcttggcgcg | aggcgtgaac | 180 |
| aagccgaccg | atgtgcacga | gcaaatcctg | acactagaag | ggctgactcg | cccggcacgg | 240 |
| ctgaattaca | caggcttgca | aaaataccag | aatttgcacg | caccgtattc | gcggtatttt | 300 |

```
gttggacagt gaatagcgat gcggcaatgg cttgtggcgt tagaaggtgc gacgaaggtg      360
gtgccaccac tgtgccagcc agtcctggcg gctcccaggg ccccgatcaa gagccaggac      420
atccaaacta cccacagcat caacgccccg gcctatactc gaaccccact tgcactctgc      480
aatggtatgg gaaccacggg gcagtcttgt gtgggtcgcg cctatcgcgg tcggcgaaga      540
ccgggaaggt acctccctcc gtctctgcac tctggcgccc ctcctccgtc tcgtggactg      600
acggacgaga gtctgggcgc cgcttttcta tccacaccgc cctttccgca tcgaagacac      660
cacccatcgt gccgccaggt cttccccaat cacccgccct gtggtcctct ctcccagccg      720
tgtttggtcg ctgcgtccac attttttccat tcgtgcccca cgatcctcgc ccatcttggc      780
gccttggata ggcacccttt tttcagcacg ccctggtgtg tagcacaacc tgacctctct      840
ctaccgcatc gcctccctcc cacacctcag ttgactccct cgtcgcacgt tgcacccgca      900
agctccccat ttcatcctat tgacaatcgc acactgtaca tgtatgctca ttattttgca      960
aaaaaacagg gggtcggttc actcctggca gacgacgcgg tgctgccgcg cgccgctgag     1020
gcggcgtcgc gacggcaaca cccatcgcac cgcacgtcga cgagtcaacc cacccctgctc    1080
aacggtgatc tccccatcgc gacaccccccc gtgaccgtac tatgtgcgtc catacgcaac    1140
atgaaaagga ccttggtccc cggaggcggc gagctcgtaa tcccgaggtt ggccccgctt     1200
ccgctggaca cccatcgcat cttccggctc gcccgctgtc gagcaagcgc cctcgtgcgc     1260
gcaacccttg tggtgcctgc ccgcagagcc gggcataaag gcgagcacca cacccgaacc     1320
agtccaattt gctttctgca ttcactcacc aacttttaca tccacacatc gtactaccac     1380
acctgcccag tcgggtttga tttctattgc aaaggtgcgg ggggggttggc gcactgcgtg    1440
ggttgtgcag ccggccgccg cggctgtacc cagcgatcag gtagcttggg ctgtatcttc     1500
tcaagcatta ccttgtcctg ggcgtaggtt tgccactagt atggccgcgt ccgtccactg     1560
caccctgatg tccgtggtct gcaacaacaa gaaccactcc gcccgcccca agctgcccaa     1620
ctcctccctg ctgccggct tcgacgtggt ggtccaggcc gcggccaccc gcttcaagaa      1680
ggagacgacg accacccgcg ccacgctgac gttcgacccc cccacgacca actccgagcg     1740
cgccaagcag cgcaagcaca ccatcgaccc ctcctcccccc gacttccagc ccatcccctc    1800
cttcgaggag tgcttccccca agtccacgaa ggagcacaag gaggtggtgc acgaggagtc    1860
cggccacgtc ctgaaggtgc ccttccgccg cgtgcacctg tccggcggcg agcccgcctt    1920
cgacaactac gacacgtccg gccccccagaa cgtcaacgcc cacatcggcc tggcgaagct    1980
gcgcaaggag tggatcgacc gccgcgagaa gctgggcacg ccccgctaca cgcagatgta    2040
ctacgcgaag cagggcatca tcacggagga gatgctgtac tgcgcgacgc gcgagaagct   2100
ggaccccgag ttcgtccgct ccgaggtcgc gcggggccgc gccatcatcc cctccaacaa   2160
gaagcacctg gagctggagc ccatgatcgt gggccgcaag ttcctggtga aggtgaacgc   2220
gaacatcggc aactccgccg tggcctcctc catcgaggag gaggtctaca aggtgcagtg   2280
ggccaccatg tggggcgccg acaccatcat ggacctgtcc acgggccgcc acatccacga   2340
gacgcgcgag tggatcctgc gcaactccgc ggtccccgtg ggcaccgtcc ccatctacca   2400
ggcgctggaa aagtggacg gcatcgcgga gaacctgaac tggaggtgt ccgcgagac    2460
gctgatcgag caggccgagc agggcgtgga ctacttcacg atccacgcgg gcgtgctgct   2520
gcgctacatc cccctgaccg ccaagcgcct gacgggcatc gtgtcccgcg gcggctccat   2580
ccacgcgaag tggtgcctgg cctaccacaa ggagaacttc gcctacgagc actgggacga   2640
catcctggac atctgcaacc agtacgacgt cgccctgtcc atcggcgacg gcctgcgccc   2700
```

```
cggctccatc tacgacgcca acgacacggc ccagttcgcc gagctgctga cccagggcga    2760
gctgacgcgc cgcgcgtggg agaaggacgt gcaggtgatg aacgagggcc ccggccacgt    2820
gcccatgcac aagatccccg agaacatgca gaagcagctg gagtggtgca acgaggcgcc    2880
cttctacacc ctgggccccc tgacgaccga catcgcgccc ggctacgacc acatcacctc    2940
cgccatcggc gcggccaaca tcggcgccct gggcaccgcc ctgctgtgct acgtgacgcc    3000
caaggagcac ctgggcctgc ccaaccgcga cgacgtgaag gcgggcgtca tcgcctacaa    3060
gatcgccgcc cacgcggccg acctggccaa gcagcacccc cacgcccagg cgtgggacga    3120
cgcgctgtcc aaggcgcgct tcgagttccg ctggatggac cagttcgcgc tgtccctgga    3180
ccccatgacg gcgatgtcct ccacgacga gacgctgccc gcggacggcg cgaaggtcgc    3240
ccacttctgc tccatgtgcg gccccaagtt ctgctccatg aagatcacgg aggacatccg    3300
caagtacgcc gaggagaacg gctacggctc cgccgaggag gccatccgcc agggcatgga    3360
cgccatgtcc gaggagttca acatcgccaa gaagacgatc tccggcgagc agcacggcga    3420
ggtcggcggc gagatctacc tgcccgagtc ctacgtcaag gccgcgcaga agtgataacct    3480
tattacgtaa cagacgacct tggcaggcgt cgggtaggga ggtggtggtg atggcgtctc    3540
gatgccatcg cacgcatcca acgaccgtat acgcatcgtc caatgaccgt cggtgtcctc    3600
tctgcctccg ttttgtgaga tgtctcaggc ttggtgcatc ctcgggtggc cagccacgtt    3660
gcgcgtcgtg ctgcttgcct ctcttgcgcc tctgtggtac tggaaaatat catcgaggcc    3720
cgttttttg ctcccatttc ctttccgcta catcttgaaa gcaaacgaca acgaagcag    3780
caagcaaaga gcacgaggac ggtgaacaag tctgtcacct gtatacatct atttccccgc    3840
gggtgcacct actctctctc ctgccccggc agagtcagct gccttacgtg acggtctcgg    3900
atccctgtag aattcgtgaa aactcgctcg accgccgcg tcccgcaggc agcgatgacg    3960
tgtgcgtgac ctgggtgttt cgtcgaaagg ccagcaaccc caaatcgcag gcgatccgga    4020
gattgggatc tgatccgagc ttggaccaga tcccccacga tgcggcacgg gaactgcatc    4080
gactcggcgc ggaacccagc tttcgtaaat gccagattgg tgtccgatac cttgatttgc    4140
catcagcgaa acaagacttc agcagcgagc gtatttggcg ggcgtgctac cagggttgca    4200
tacattgccc atttctgtct ggaccgcttt accggcgcag agggtgagtt gatggggttg    4260
gcaggcatcg aaacgcgcgt gcatggtgtg tgtgtctgtt ttcggctgca caattttcaat    4320
agtcggatgg gcgacggtag aattgggtgt tgcgctcgcg tgcatgcctc gccccgtcgg    4380
gtgtcatgac cgggactgga atccccctc gcgaccctcc tgctaacgct cccgactctc    4440
ccgcccgcgc gcaggataga ctctagttca accaatcgac aatgggcctg tcctccgtct    4500
gcaccttctc cttccagacg aactaccaca ccctgctgaa cccccacaac aacaacccca    4560
agacctccct gctgtgctac cgccaccca agaccccat caagtactcc tacaacaact    4620
tccctccaa gcactgctcc accaagtcct tccacctgca gaacaagtgc tccgagtccc    4680
tgtccatcgc caagaactcc atccgcgccg ccacgacgaa ccagaccgag cccccgagt    4740
ccgacaacca ctccgtcgcc acgaagatcc tgaacttcgg caaggcctgc tggaagctgc    4800
agcgccccta caccatcatc gcgttcacct cctgcgcgtg cggcctgttc ggcaaggagc    4860
tgctgcacaa caccaacctg atctcctggt ccctgatgtt caaggccttc ttcttcctgg    4920
tggcgatcct gtgcatcgcg tccttcacca cgacgatcaa ccagatctac gacctgcaca    4980
tcgaccgcat caacaagccc gacctgcccc tggcctccgg cgagatctcc gtgaacaccg    5040
cctggatcat gtccatcatc gtggccctgt tcggcctgat catcacgatc aagatgaagg    5100
```

```
gcggccccct gtacatcttc ggctactgct tcggcatctt cggcggcatc gtctactccg    5160
tccccccctt ccgctggaag cagaacccct ccaccgcctt cctgctgaac ttcctggccc    5220
acatcatcac gaacttcacg ttctactacg cgtcccgcgc cgcgctgggc ctgcccttcg    5280
agctgcgccc ctccttcacg ttcctgctgg cgttcatgaa gtccatgggc tccgcgctgg    5340
cgctgatcaa ggacgcgtcc gacgtggagg gcgacacgaa gttcggcatc tccaccctgg    5400
cctccaagta cggctcccgc aacctgacgc tgttctgctc cggcatcgtc ctgctgtcct    5460
acgtcgcggc catcctggcc ggcatcatct ggccccaggc gttcaactcc aacgtcatgc    5520
tgctgtccca cgcgatcctg gccttctggc tgatcctgca gacccgcgac ttcgcgctga    5580
cgaactacga ccccgaggcc ggccgccgct tctacgagtt catgtggaag ctgtactacg    5640
cggagtacct ggtgtacgtg ttcatctgac tcgagacaga cgaccttggc aggcgtcggg    5700
tagggaggtg gtggtgatgg cgtctcgatg ccatcgcacg catccaacga ccgtatacgc    5760
atcgtccaat gaccgtcggt gtcctctctg cctccgtttt gtgagatgtc tcaggcttgg    5820
tgcatcctcg ggtggccagc cacgttgcgc gtcgtgctgc ttgcctctct gcgcctctg    5880 tggtactgga aaatatcatc gaggcccgtt ttttgctcc catttccttt ccgctacatc    5940
ttgaaagcaa acgacaaacg aagcagcaag caaagagcac gaggacggtg aacaagtctg    6000
tcacctgtat acatctattt ccccgcgggt gcacctactc tctctcctgc cccggcagag    6060
tcagctgcct tacgtgacga agcttgagct cagcggcgac ggtcctgcta ccgtacgacg    6120
ttgggcacgc ccatgaaagt ttgtataccg agcttgttga gcgaactgca agcgcggctc    6180
aaggatactt gaactcctgg attgatatcg gtccaataat ggatggaaaa tccgaacctc    6240
gtgcaagaac tgagcaaacc tcgttacatg gatgcacagt cgccagtcca atgaacattg    6300
aagtgagcga actgttcgct tcggtggcag tactactcaa agaatgagct gctgttaaaa    6360
atgcactctc gttctctcaa gtgagtggca gatgagtgct cacgccttgc acttcgctgc    6420
ccgtgtcatg ccctgcgccc caaaatttga aaaaagggat gagattattg ggcaatggac    6480
gacgtcgtcg ctccgggagt caggaccggc ggaaaataag aggcaacaca ctccgcttct    6540
ta                                                                   6542

<210> SEQ ID NO 10
<211> LENGTH: 9569
<212> TYPE: DNA
<213> ORGANISM: Artificial Sequence
<220> FEATURE:
<223> OTHER INFORMATION: Plasmid pUR17003

<400> SEQUENCE: 10
aacggaggtc tgtcaccaaa tggaccccgt ctattgcggg aaaccacggc gatggcacgt      60
ttcaaaactt gatgaaatac aatattcagt atgtcgcggg cggcgacggc ggggagctga    120
tgtcgcgctg gtattgcttt aatcgccagc ttcgcccccg tcttggcgcg aggcgtgaac    180
aagccgaccg atgtgcacga gcaaatcctg acactagaag ggctgactcg cccggcacgg    240
ctgaattaca caggcttgca aaaataccag aatttgcacg caccgtattc gcggtatttt    300
gttggacagt gaatagcgat gcggcaatgg cttgtggcgt tagaaggtgc gacgaaggtg    360
gtgccaccac tgtgccagcc agtcctggcg gctcccaggg ccccgatcaa gagccaggac    420
atccaaacta cccacagcat caacgccccg gcctatactc gaaccccact tgcactctgc    480
aatggtatgg gaaccacggg gcagtcttgt gtgggtcgcg cctatcgcgg tcggcgaaga    540
ccgggaaggt acctccctcc gtctctgcac tctggcgccc ctcctccgtc tcgtggactg    600
```

```
acggacgaga gtctgggcgc cgcttttcta tccacaccgc cctttccgca tcgaagacac    660
cacccatcgt gccgccaggt cttccccaat cacccgccct gtggtcctct ctcccagccg    720
tgtttggtcg ctgcgtccac attttttccat tcgtgcccca cgatcctcgc ccatcttggc    780
gccttggata ggcacccttt tttcagcacg ccctggtgtg tagcacaacc tgacctctct    840
ctaccgcatc gcctccctcc cacacctcag ttgactccct cgtcgcacgt tgcacccgca    900
agctccccat ttcatcctat tgacaatcgc acactgtaca tgtatgctca ttattttgca    960
aaaaaacagg gggtcggttc actcctggca gacgacgcgg tgctgccgcg cgccgctgag   1020
gcggcgtcgc gacggcaaca cccatcgcac cgcacgtcga cgagtcaacc cacccctgctc   1080 aacggtgatc tccccatcgc gacacccccc gtgaccgtac tatgtgcgtc catacgcaac   1140
atgaaaagga ccttggtccc cggaggcggc gagctcgtaa tcccgaggtt ggccccgctt   1200
ccgctggaca cccatcgcat cttccggctc gcccgctgtc gagcaagcgc cctcgtgcgc   1260 gcaaccttg tggtcctgc ccgcagagcc gggcataaag gcgagcacca cacccgaacc   1320
agtccaattt gctttctgca ttcactcacc aacttttaca tccacacatc gtactaccac   1380
acctgcccag tcgggtttga tttctattgc aaaggtgcgg ggggttggc gcactgcgtg   1440 ggttgtgcag ccggccgccg cggctgtacc cagcgatcag gtagcttggg ctgtatcttc   1500
tcaagcatta ccttgtcctg ggcgtaggtt tgccactagt atggccgcgt ccgtccactg   1560
caccctgatg tccgtggtct gcaacaacaa gaaccactcc gcccgcccca agctgcccaa   1620
ctcctccctg ctgcccggct tcgacgtggt ggtccaggcc gcggccaccc gcttcaagaa   1680
ggagacgacg accaccccgcg ccacgctgac gttcgacccc cccacgacca actccgagcg   1740
cgccaagcag cgcaagcaca ccatcgaccc ctcctccccc gacttccagc ccatcccctc   1800
cttcgaggag tgcttcccca agtccacgaa ggagcacaag gaggtggtgc acgaggagtc   1860
cggccacgtc ctgaaggtgc ccttccgccg cgtgcacctg tccggcggcg agcccgcctt   1920
cgacaactac gacacgtccg gcccccagaa cgtcaacgcc cacatcggcc tggcgaagct   1980
gcgcaaggag tggatcgacc gccgcgagaa gctgggcacg ccccgctaca cgcagatgta   2040
ctacgcgaag cagggcatca tcacggagga gatgctgtac tgcgcgacgc gcgagaagct   2100
ggaccccgag ttcgtccgct ccgaggtcgc gcggggccgc gccatcatcc cctccaacaa   2160
gaagcacctg gagctggagc ccatgatcgt gggccgcaag ttcctggtga aggtgaacgc   2220
gaacatcggc aactccgccg tggcctcctc catcgaggag gaggtctaca aggtgcagtg   2280
ggccaccatg tggggcgccg acaccatcat ggacctgtcc acgggccgcc acatccacga   2340
gacgcgcgag tggatcctgc gcaactccgc ggtccccgtg ggcaccgtcc ccatctacca   2400
ggcgctggag aaggtggacg gcatcgcgga gaacctgaac tgggaggtgt ccgcgagac   2460 gctgatcgag caggccgagc agggcgtgga ctacttcacg atccacgcgg gcgtgctgct   2520
gcgctacatc cccctgaccg ccaagcgcct gacgggcatc gtgtcccgcg gcggctccat   2580
ccacgcgaag tggtgcctgg cctaccacaa ggagaacttc gcctacgagc actgggacga   2640
catcctggac atctgcaacc agtacgacgt cgccctgtcc atcggcgacg gcctgcgccc   2700
cggctccatc tacgacgcca acgacacggc ccagttcgcc gagctgctga cccagggcga   2760
gctgacgcgc cgcgcgtggg agaaggacgt gcaggtgatg aacgagggcc ccggccacgt   2820
gcccatgcac aagatccccg agaacatgca gaagcagctg gagtggtgca acgaggcgcc   2880
cttctacacc ctgggccccc tgacgaccga catcgcgccc ggctacgacc acatcacctc   2940
cgccatcggc gcggccaaca tcggcgcccct gggcaccgcc ctgctgtgct acgtgacgcc   3000
```

```
caaggagcac ctgggcctgc ccaaccgcga cgacgtgaag gcgggcgtca tcgcctacaa    3060
gatcgccgcc cacgcggccg acctggccaa gcagcacccc cacgcccagg cgtgggacga    3120
cgcgctgtcc aaggcgcgct tcgagttccg ctggatggac cagttcgcgc tgtccctgga    3180
ccccatgacg gcgatgtcct tccacgacga gacgctgccc gcggacggcg cgaaggtcgc    3240
ccacttctgc tccatgtgcg gccccaagtt ctgctccatg aagatcacgg aggacatccg    3300
caagtacgcc gaggagaacg gctacggctc cgccgaggag gccatccgcc agggcatgga    3360
cgccatgtcc gaggagttca acatcgccaa gaagacgatc tccggcgagc agcacggcga    3420
ggtcggcggc gagatctacc tgcccgagtc ctacgtcaag gccgcgcaga agtgataacct   3480 tattacgtaa cagacgacct tggcaggcgt cgggtaggga ggtggtggtg atggcgtctc    3540
gatgccatcg cacgcatcca acgaccgtat acgcatcgtc caatgaccgt cggtgtcctc    3600
tctgcctccg ttttgtgaga tgtctcaggc ttggtgcatc ctcgggtggc cagccacgtt    3660
gcgcgtcgtg ctgcttgcct ctcttgcgcc tctgtggtac tggaaaatat catcgaggcc    3720 cgttttttg ctcccatttc ctttccgcta catcttgaaa gcaaacgaca aacgaagcag     3780
caagcaaaga gcacgaggac ggtgaacaag tctgtcacct gtatacatct atttccccgc    3840
gggtgcacct actctctctc ctgccccggc agagtcagct gccttacgtg acggtctcgg    3900
atccctgtag aattcgtgaa aactcgctcg accgcccgcg tcccgcaggc agcgatgacg    3960
tgtgcgtgac ctgggtgttt cgtcgaaagg ccagcaaccc caaatcgcag gcgatccgga    4020
gattgggatc tgatccgagc ttggaccaga tcccccacga tgcggcacgg gaactgcatc    4080
gactcggcgc ggaacccagc tttcgtaaat gccagattgg tgtccgatac cttgatttgc    4140
catcagcgaa acaagacttc agcagcgagc gtatttggcg ggcgtgctac cagggttgca    4200
tacattgccc atttctgtct ggaccgcttt accggcgcag agggtgagtt gatggggttg    4260
gcaggcatcg aaacgcgcgt gcatggtgtg tgtgtctgtt ttcggctgca caatttcaat    4320
agtcggatgg gcgacggtag aattgggtgt tgcgctcgcg tgcatgcctc gccccgtcgg    4380
gtgtcatgac cgggactgga atcccccctc gcgaccctcc tgctaacgct cccgactctc    4440
ccgcccgcgc gcaggataga ctctagttca accaatcgac aatgggcctg tcctccgtct    4500
gcaccttctc cttccagacg aactaccaca ccctgctgaa cccccacaac aacaacccca    4560
agacctccct gctgtgctac cgccaccccg agaccccccat caagtactcc tacaacaact    4620 tccccctccaa gcactgctcc accaagtcct tccacctgca gaacaagtgc tccgagtccc    4680
tgtccatcgc caagaactcc atccgcgccg ccacgacgaa ccagaccgag ccccccgagt    4740
ccgacaacca ctccgtcgcc acgaagatcc tgaacttcgg caaggcctgc tggaagctgc    4800
agcgccccta ccatcatcat cgcgttcacct cctgcgcgtg cggcctgttc ggcaaggagc    4860
tgctgcacaa caccaacctg atctcctggt ccctgatgtt caaggccttc ttcttcctgg    4920
tggcgatcct gtgcatcgcg tccttcacca cgacgatcaa ccagatctac gacctgcaca    4980
tcgaccgcat caacaagccc gacctgcccc tggcctccgg cgagatctcc gtgaacaccg    5040
cctggatcat gtccatcatc gtggccctgt tcggcctgat catcacgatc aagatgaagg    5100
gcggccccct gtacatcttc ggctactgct tcggcatctt cggcggcatc gtctactccg    5160
tccccccctt ccgctggaag cagaacccct ccaccgcctt cctgctgaac ttcctggccc    5220
acatcatcac gaacttcacg ttctactacg cgtcccgcgc cgcgctgggc ctgcccttcg    5280
agctgcgccc ctccttcacg ttcctgctgg cgttcatgaa gtccatgggc tccgcgctgg    5340
cgctgatcaa ggacgcgtcc gacgtggagg gcgacacgaa gttcggcatc tccaccctgg    5400
```

```
cctccaagta cggctcccgc aacctgacgc tgttctgctc cggcatcgtc ctgctgtcct   5460
acgtcgcggc catcctggcc ggcatcatct ggccccaggc gttcaactcc aacgtcatgc   5520
tgctgtccca cgcgatcctg gccttctggc tgatcctgca gacccgcgac ttcgcgctga   5580
cgaactacga ccccgaggcc ggccgccgct tctacgagtt catgtggaag ctgtactacg   5640
cggagtacct ggtgtacgtg ttcatctgac tcgaggcagc agcagctcgg atagtatcga   5700
cacactctgg acgctggtcg tgtgatggac tgttgccgcc acacttgctg ccttgacctg   5760
tgaatatccc tgccgctttt atcaaacagc ctcagtgtgt ttgatcttgt gtgtacgcgc   5820
ttttgcgagt tgctagctgc ttgtgctatt tgcgaatacc cccccagca tcccctttccc   5880 tcgtttcata tcgcttgcat cccaaccgca acttatctac gctgtcctgc tatccctcag   5940
cgctgctcct gctcctgctc actgcccctc gcacagcctt ggtttgggct ccgcctgtat   6000
tctcctggta ctgcaacctg taaaccagca ctgcaatgct gatgcacggg aagtagtggg   6060
atgggaacac aaatgaaaag cttggccgac aggacgcgcg tcaaaggtgc tggtcgtgta   6120
tgccctggcc ggcaggtcgt tgctgctgct ggttagtgat tccgcaaccc tgattttggc   6180
gtcttatttt ggcgtggcaa acgctggcgc ccgcgagccg ggccggcggc gatgcggtgc   6240
cccacggctg ccggaatcca agggaggcaa gagcgcccgg gtcagttgaa gggctttacg   6300
cgcaaggtac agccgctcct gcaaggctgc gtggtggaat tggacgtgca ggtcctgctg   6360
aagttcctcc accgcctcac cagcggacaa agcaccggtg tatcaggtcc gtgtcatcca   6420
ctctaaagaa ctcgactacg acctactgat ggccctagat tcttcatcaa aaacgcctga   6480
gacacttgcc caggattgaa actccctgaa gggaccacca ggggccctga gttgttcctt   6540
ccccccgtgg cgagctgcca gccaggctgt acctgtgatc gaggctggcg ggaaaatagg   6600
cttcgtgtgc tcaggtcatg ggaggtgcag gacagctcat gaaacgccaa caatcgcaca   6660
attcatgtca agctaatcag ctatttcctc ttcacgagct gtaattgtcc caaaattctg   6720
gtctaccggg ggtgatcctt cgtgtacggg ccccttccctc aacccctaggt atgcgcgcat   6780 gcggtcgccg cgcaactcgc gcgagggccg agggtttggg acgggccgtc ccgaaatgca   6840
gttgcacccg gatgcgtggc accttttttg cgataattta tgcaatggac tgctctgcaa   6900
aattctggct ctgtcgccaa ccctaggatc agcggcgtag gatttcgtaa tcattcgtcc   6960
tgatggggag ctaccgacta ccctaatatc agcccgactg cctgacgcca cgtccactt   7020 ttgtgcacac attccattcg tgcccaagac atttcattgt ggtgcgaagc gtccccagtt   7080
acgctcacct gtttcccgac ctccttactg ttctgtcgac agagcgggcc cacaggccgg   7140
tcgcagccat gaaccccgc gagaacttcc tgaagtgctt ctcccagtac atccccaaca   7200
acgccacgaa cctgaagctg gtgtacaccc agaacaaccc cctgtacatg tccgtcctga   7260
actccacgat ccacaacctg cgcttcacgt ccgacaccac cccaagccc ctggtgatcg   7320 tgacgccctc ccacgtgtcc cacatccagg gcacgatcct gtgctccaag aaggtgggcc   7380
tgcagatccg cacgcgctcc ggcggccacg actccgaggg catgtcctac atctcccagg   7440
tgcccttcgt gatcgtggac ctgcgcaaca tgcgctccat caagatcgac gtgcactccc   7500
agaccgcctg ggtggaggcc ggcgccaccc tgggcgaggt gtactactgg gtcaacgaga   7560
agaacgagaa cctgtccctg gccgccggct actgcccac ggtctgcgcg gcggccact   7620 tcggcggcgg cggctacggc ccctgatgc gcaactacgg cctggcggcg gacaacatca   7680
tcgacgccca cctggtgaac gtccacggca aggtgctgga ccgcaagtcc atgggcgagg   7740
acctgttctg ggccctgcgc ggcggcggcg ccgagtcctt cggcatcatc gtggcgtgga   7800
```

| | | |
|---|---|---|
| agatccgcct ggtggccgtc cccaagtcca ccatgttctc cgtcaagaag atcatggaga | 7860 |
| tccacgagct ggtcaagctg gtgaacaagt ggcagaacat cgcctacaag tacgacaagg | 7920 |
| acctgctgct gatgacgcac ttcatcacgc gcaacatcac cgacaaccag ggcaagaaca | 7980 |
| agaccgcgat ccacacctac ttctcctccg tgttcctggg cggcgtggac tccctggtgg | 8040 |
| acctgatgaa caagtccttc cccgagctgg gcatcaagaa gaccgactgc cgccagctgt | 8100 |
| cctggatcga cacgatcatc ttctactccg gcgtggtcaa ctacgacacg gacaacttca | 8160 |
| acaaggagat cctgctggac cgctccgcgg gccagaacgg cgcgttcaag atcaagctgg | 8220 |
| actacgtcaa gaagcccatc cccgagtccg tgttcgtgca gatcctggag aagctgtacg | 8280 |
| aggaggacat cggcgcgggc atgtacgccc tgtacccta cggcggcatc atggacgaga | 8340 |
| tctccgagtc cgccatcccc ttcccccacc gcgccggcat cctgtacgag ctgtggtaca | 8400 |
| tctgctcctg ggagaagcag gaggacaacg agaagcacct gaactggatc cgcaacatct | 8460 |
| acaacttcat gaccccctac gtgtccaaga ccccgcct ggcctacctg aactaccgcg | 8520 |
| acctggacat cggcatcaac gaccccaaga acccaacaa ctacacgcag gcgcgcatct | 8580 |
| ggggcgagaa gtacttcggc aagaacttcg accgcctggt gaaggtcaag acgctggtgg | 8640 |
| accccaacaa cttcttccgc aacgagcagt ccatccccc cctgccccgc caccgccact | 8700 |
| gactcgagac agacgacctt ggcaggcgtc gggtagggag gtggtggtga tggcgtctcg | 8760 |
| atgccatcgc acgcatccaa cgaccgtata cgcatcgtcc aatgaccgtc ggtgtcctct | 8820 |
| ctgcctccgt tttgtgagat gtctcaggct tggtgcatcc tcgggtggcc agccacgttg | 8880 |
| cgcgtcgtgc tgcttgcctc tcttgcgcct ctgtggtact ggaaaatatc atcgaggccc | 8940 |
| gttttttttgc tcccatttcc tttccgctac atcttgaaag caaacgacaa acgaagcagc | 9000 |
| aagcaaagag cacgaggacg gtgaacaagt ctgtcacctg tatacatcta tttccccgcg | 9060 |
| ggtgcaccta ctctctctcc tgccccggca gagtcagctg ccttacgtga cggagctcag | 9120 |
| cggcgacggt cctgctaccg tacgacgttg ggcacgccca tgaaagtttg tataccgagc | 9180 |
| ttgttgagcg aactgcaagc gcggctcaag gatacttgaa ctcctggatt gatatcggtc | 9240 |
| caataatgga tggaaaatcc gaacctcgtg caagaactga gcaaacctcg ttacatggat | 9300 |
| gcacagtcgc cagtccaatg aacattgaag tgagcgaact gttcgcttcg gtggcagtac | 9360 |
| tactcaaaga tgagctgct gttaaaaatg cactctcgtt ctctcaagtg agtggcagat | 9420 |
| gagtgctcac gccttgcact tcgctgcccg tgtcatgccc tgcgcccaa aatttgaaaa | 9480 |
| aagggatgag attattgggc aatggacgac gtcgtcgctc cgggagtcag gaccggcgga | 9540 |
| aaataagagg caacacactc cgcttcttta | 9569 |

<210> SEQ ID NO 11
<211> LENGTH: 38
<212> TYPE: PRT
<213> ORGANISM: Artificial Sequence
<220> FEATURE:
<223> OTHER INFORMATION: Chlorella protothecoides plastid targeting
      transit peptide from stearoyl-ACP desaturase

<400> SEQUENCE: 11

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile
        35

```
<210> SEQ ID NO 12
<211> LENGTH: 33
<212> TYPE: PRT
<213> ORGANISM: Artificial Sequence
<220> FEATURE:
<223> OTHER INFORMATION: Prototheca moriformis plastid targeting
      sequence from stearoyl-ACP desaturase

<400> SEQUENCE: 12

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg

<210> SEQ ID NO 13
<211> LENGTH: 34
<212> TYPE: PRT
<213> ORGANISM: Artificial Sequence
<220> FEATURE:
<223> OTHER INFORMATION: Prototheca moriformis plastid targeting transit
      peptide from 1-hydroxy-2-methyl-(E)-butenyl
      4-diphosphate reductase

<400> SEQUENCE: 13

Met Thr Phe Gly Val Ala Leu Pro Ala Met Gly Arg Gly Val Ser Leu
1               5                   10                  15

Pro Arg Pro Arg Val Ala Val Arg Ala Gln Ser Ala Ser Gln Val Leu
            20                  25                  30

Glu Ser

<210> SEQ ID NO 14
<211> LENGTH: 35
<212> TYPE: PRT
<213> ORGANISM: Artificial Sequence
<220> FEATURE:
<223> OTHER INFORMATION: Prototheca moriformis plastid targeting transit
      peptide from delta (12) fatty acid desaturase

<400> SEQUENCE: 14

Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg
        35

<210> SEQ ID NO 15
<211> LENGTH: 11482
<212> TYPE: DNA
<213> ORGANISM: Artificial Sequence
<220> FEATURE:
<223> OTHER INFORMATION: Plasmid pUO92

<400> SEQUENCE: 15
agcccgcacc ctcgttgatc tgggagccct gcgcagcccc ttaaatcatc tcagtcaggt      60
ttctgtgttc aactgagcct aaagggcttt cgtcatgcgc acgagcacac gtatatcggc     120
cacgcagttt ctcaaaagcg gtagaacagt tcgcgagccc tcgtaggtcg aaaacttgcg     180
ccagtactat taaattaaat taattgatcg aacgagacgc gaaacttttg cagaatgcca     240
ccgagtttgc ccagagaatg ggagtggcgc cattcaccat ccgcctgtgc ccggcttgat     300
tcgccgagac gatggacggc gacaccaggg agcggcttgc gagccccgag ccggtagcag     360
```

| | |
|---|---|
| gaacaatgat cgacaatctt cctgtccaat tactggcaac cattagaaag agccggagcg | 420 |
| cgttgaaagt ctgcaatcga gtaattttc gatacgtcgg gcctgctgaa ccctaaggct | 480 |
| ccggactttg tttaaggcga tccaagatgc acgcggcccc aggcacgtat ctcaagcaca | 540 |
| aaccccagcc ttagtttcga gactttggga gatagcgacc gatatctagt ttggcatttt | 600 |
| gtatattaat tacctcaagc aatggagcgc tctgatgcgg tgcagcgtcg gctgcagcac | 660 |
| ctggcagtgg cgctagggtc gccctatcgc tcggaacctg gtcagctggc tcccgcctcc | 720 |
| tgctcagcct cttccactat gccaggagcc ctccgtctct gcactctggc gcccctcctc | 780 |
| cgtctcgtgg actgacggac gagagtctgg gcgccgcttt tctatccaca ccgccctttc | 840 |
| cgcatcgatg acaccaccca tcgtgccgcc aggtcatccc caatcacccg ccctgtggtc | 900 |
| ctctctccca gccgtgtttg gtcgctgcgt ccacattttt ccattcgtgc cccacgatcc | 960 |
| tcgcccatct tggcgccttg gataggcacc cttttttcag cacgccctgg tgtgtagcac | 1020 |
| aacctgacct ctctctaccg catcgcctcc ctcccacacc tcagttgact ccctcgtcgc | 1080 |
| acgttgcacc cgcaagctcc ccatttcatc ctattgacaa tcgcacactg tacatgtatg | 1140 |
| ctcattattt tgcaaaaaaa caggggggtcg gttcactcct ggcagacgac gcggtgctgc | 1200 |
| cgcgcgccgc tgaggcggcg tcgcgacggc aacacccatc gcaccgcacg tcgacgagtc | 1260 |
| aacccaccct gctcaacggt gatctcccca tcgcgacacc cccgtgacc gtactatgtg | 1320 |
| cgtccatacg caacatgaaa aggaccttgg tccccgagg cggcgagctc gtaatcccga | 1380 |
| ggttggcccc gcttccgctg gacacccatc gcatcttccg gctcgcccgc tgtcgagcaa | 1440 |
| gcgccctcgt gcgcgcaacc cttgtggtgc ctgcccgcag agcccgggcat aaaggcgagc | 1500 |
| accacacccg aaccagtcca atttgctttc tgcattcact caccaacttt tacatccaca | 1560 |
| catcgtacta ccacacctgc ccagtcgggt ttgattccta ttgcaaaggt gcgggggggt | 1620 |
| tggcgcactg cgtgggttgt gcagccggcc gccgcggctg tacccagcga tcaggtagct | 1680 |
| tgggctgtat cttctcaagc attaccttgt cctgggcgta ggtttgccaa tggccaccgc | 1740 |
| atccactttc tcggcgttca atgcccgctg cggcgacctg cgtcgctcgg cgggctccgg | 1800 |
| gccccggcgc ccagcgaggc ccctccccgt gcgcgggcgc cccgcgcga ccctgacctt | 1860 |
| cgacccccccc accacgaact ccgagcgcgc caagcagcgc aagcacacca tcgacccgtc | 1920 |
| ctccccggac tttcagccca tccctcctt cgaggagtgc tttcccaagt ccaccaagga | 1980 |
| gcacaaggag gtcgtgcacg aggagtccgg ccacgtcctg aaggtgccgt tccgccgcgt | 2040 |
| ccacctgtcc ggcggcgagc ccgcctttga caactacgac acgtccggcc ccagaacgt | 2100 |
| caacgcccac atcggcctgg ccaagctgcg caaggagtgg atcgaccgcc gcgagaagct | 2160 |
| gggcacgccg cgctacaccc agatgtacta cgccaagcag ggcatcatca ccgaggagat | 2220 |
| gctgtactgc gcgacgcgcg agaagctgga ccccgagttc gtccgctccg aggtggcccg | 2280 |
| cggccgcgcc atcatcccct ccaacaagaa gcacctggag ctggagccca tgatcgtggg | 2340 |
| ccgcaagttt ctggtgaagg tcaacgccaa catccggcaac tccgcggtgg cctcctccat | 2400 |
| cgaggaggag gtgtacaagg tgcagtgggc caccatgtgg ggcgcggaca ccatcatgga | 2460 |
| cctgtccacc ggccgccaca tccacgagac gcgcgagtgg atcctgcgca actccgccgt | 2520 |
| ccccgtgggc accgtgccga tctaccaggc gctggagaag gtggacggca tcgcggagaa | 2580 |
| cctgaactgg gaggtgtttc gcgagacgct gatcgagcag gccgagcagg gcgtggacta | 2640 |
| cttcacgatc cacgcgggcg tcctgctgcg ctacatcccc ctgacggcca agcgcctgac | 2700 |
| gggcatcgtg tcccgcggcg gctccatcca cgccaagtgg tgcctggcgt accacaagga | 2760 |

-continued

```
gaactttgcg tacgagcact gggacgacat cctggacatc tgcaaccagt acgacgtcgc   2820
gctgtccatc ggcgacggcc tgcgccccgg ctccatctac gacgccaacg acaccgccca   2880
gttcgcggag ctgctgaccc agggcgagct gacccgccgc gcctgggaga aggacgtcca   2940
ggtcatgaac gagggcccgg gccacgtccc catgcacaag atccccgaga acatgcagaa   3000
gcagctggag tggtgcaacg aggcgccctt ctacacgctg ggcccccctga ccaccgacat   3060
cgccccgggc tacgaccaca tcacctccgc gatcggcgcc gcgaacatcg gcgcgctggg   3120
caccgccctg ctgtgctacg tcacgcccaa ggagcacctg ggcctgccca accgcgacga   3180
cgtgaaggcc ggcgtgatcg cctacaagat cgccgcgcac gccgcggacc tggccaagca   3240
gcacccccac gcgcaggcct gggacgacgc gctgtccaag gcccgcttcg agttccgctg   3300
gatggaccag tttgcgctgt ccctggaccc gatgaccgcc atgtcctttc acgacgagac   3360
gctgcccgcc gacggcgcca aggtcgcgca cttctgctcc atgtgcggcc ccaagttttg   3420
ctccatgaag atcaccgagg acatccgcaa gtacgcggag gagaacggct acggctccgc   3480
cgaggaggcg atccgccagg gcatggacgc catgtccgag gagtttaaca tcgcccgcaa   3540
gacgatctcc ggcgagcagc acggcgaggt gggcggcgag atctacctgc ccgagtccta   3600
cgtcaaggcg gcccagaagt gacacgcccg cgcggcgcac ctgacctgtt ctctcgaggg   3660
cgcctgttct gccttgcgaa acaagcccct ggagcatgcg tgcatgatcg tctctggcgc   3720
cccgccgcgc ggtttgtcgc cctcgcgggc gccgcggccg cgggggcgca ttgaaattgt   3780
tgcaaacccc acctgacaga ttgagggccc aggcaggaag gcgttgagat ggaggtacag   3840
gagtcaagta actgaaagtt tttatgataa ctaacaacaa agggtcgttt ctggccagcg   3900
aatgacaaga acaagattcc acatttccgt gtagaggctt gccatcgaat gtgagcgggc   3960
gggccgcgga cccgacaaaa cccttacgac gtggtaagaa aaacgtggcg ggcactgtcc   4020
ctgtagcctg atgaccagca ggagacgatc ggaagcatca cagcacacgc ttgcaaagga   4080
gatcaaaaac gcctgagaca cttgcccagg attgaaactc cctgaaggga ccaccagggg   4140
ccctgagttg ttccttcccc ccgtggcgag ctgccagcca ggctgtacct gtgatcgggg   4200
ctggcgggaa aacaggcttc gtgtgctcag gttatgggag gtgcaggaca gctcattaaa   4260
cgccaacaat cgcacaattc atggcaagct aatcagttat ttcccattaa cgagctataa   4320
ttgtcccaaa attctggtct accgggggtg atccttcgtg tacgggccct tccctcaacc   4380
ctaggtatgc gcacatgcgg tcgccgcgca acgcgcgcga gggccgaggg tttgggacgg   4440
gccgtcccga aatgcagttg cacccggatg cgtggcacct tttttgcgat aatttatgca   4500
atggactgct ctgcaaaatt ctggctctgt cgccaaccct aggatcagcg gtgtaggatt   4560
tcgtaatcat tcgtcctgat ggggagctac cgactgccct agtatcagcc cgactgcctg   4620
acgccagcgt ccacttttgt gcacacattc cattcgtgcc caagacattt cattgtggtg   4680
cgaagcgtcc ccagttacgc tcacctgatc cccaacctcc ttattgttct gtcgacagag   4740
tgggcccaga ggccggtcgc agccaatggc cgtcaagcac ctgatcgtgc tgaagttcaa   4800
ggacgagatc acggaggccc agaaggagga gttcttcaag acctacgtca acctggtgaa   4860
catcatcccc gccatgaagg acgtgtactg gggcaaggac gtcacgcaga agaacaagga   4920
ggagggctac acgcacatcg tggaggtcac cttcgagtcc gtggagacga tccaggacta   4980
catcatccac cccgcgcacg tgggcttcgg cgacgtgtac cgctccttct gggagaagct   5040
gctgatcttc gactacaccc cccgcaagtg acacagacga ccttggcagg cgtcgggtag   5100
ggaggtggtg gtgatggcgt ctcgagcgca tcgcacgcat ccaacgaccg tatacgcatc   5160
```

```
gtccaatgac cgtcggtgtc ctctctgcct ccgttttgtg agatgtctca ggcttggtgc    5220
atcctcgggt ggccagccac gttgcgcgtc gtgctgcttg cctctcttgc gcctctgtgg    5280
tactggaaaa tatcatcgag gcccgttttt ttgctcccat ttcctttccg ctacatcttg    5340
aaagcaaacg acaaacgaag cagcaagcaa agagcacgag gacggtgaac aagtctgtca    5400
cctgtataca tctatttccc cgcgggtgca cctactctct ctcctgcccc ggcagagtca    5460
gctgccttac gtgacgcgct tgggaaggag gtgaaaactc gctcgaccgc ccgcgtcccg    5520
caggcagcga tgacgtgtgc gtgacctggg tgtttcgtcg aaaggccagc aaccccaaat    5580
cgcaggcgat ccggagattg ggatctgatc cgagcttgga ccagatcccc cacgatgcgg    5640
cacgggaact gcatcgactc ggcgcggaac ccagctttcg taaatgccag attggtgtcc    5700 gatccttga tttgccatca gcgaaacaag acttcagcag cgagcgtatt tggcgggcgt    5760
gctaccaggg ttgcatacat tgcccatttc tgtctggacc gctttaccgg cgcagagggt    5820
gagttgatgg ggttggcagg catcgaaacg cgcgtgcatg gtgtgtgtgt ctgttttcgg    5880
ctgcacaatt tcaatagtcg gatgggcgac ggtagaattg ggtgttgcgc tcgcgtgcat    5940
gcctcgcccc gtcgggtgtc atgaccggga ctggaatccc ccctcgcgac cctcctgcta    6000
acgctcccga ctctcccgcc cgcgcgcagg atagactcta gttcaaccaa tcgacaaatg    6060
aaccacctgc gcgcggaggg cccggcgtcc gtgctggcca tcggcaccgc caaccccgag    6120
aacatcctgc tgcaggacga gttccccgac tactacttcc gcgtgaccaa gtccgagcac    6180
atgacccagc tgaaggagaa gtttcgcaag atctgcgaca gtccatgat ccgcaagcgc    6240 aactgctttc tgaacgagga gcacctgaag cagaaccccc gcctggtcga gcacgagatg    6300
cagacgctgg acgcccgcca ggacatgctg gtggtcgagg tcccgaagct gggcaaggac    6360
gcctgcgcca aggccatcaa ggagtggggc cagcccaagt ccaagatcac ccacctgatc    6420
ttcacctccg cctccaccac ggacatgccc ggcgccgact accactgcgc caagctgctg    6480
ggcctgtccc cctccgtgaa gcgcgtcatg atgtaccagc tgggctgcta cggcggcggc    6540
accgtcctgc gcatcgccaa ggacatcgcg gagaacaaca agggcgcgcg cgtgctggcg    6600
gtctgctgcg acatcatggc ctgcctgttt cgcggcccct ccgagtccga cctggagctg    6660
ctggtgggcc aggcgatctt tggcgacggc gccgcggcgg tgatcgtcgg cgccgagccc    6720
gacgagtccg tcggcgagcg ccccatcttc gagctggtgt ccaccggcca gaccatcctg    6780
ccgaactccg agggcacgat cggcggccac atccgcgagg ccggcctgat cttcgacctg    6840
cacaaggacg tgcccatgct gatctccaac aacatcgaga agtgcctgat cgaggccttc    6900
acgccgatcg gcatctccga ctggaactcc atcttctgga tcacccaccc gggcggcaag    6960
gcgatcctgg acaaggtgga ggagaagctg cacctgaagt ccgacaagtt cgtggactcc    7020
cgccacgtgc tgtccgagca cggcaacatg tcctcctcca ccgtcctgtt cgtgatggac    7080
gagctgcgca gcgctccct ggaggagggc aagtccacca cgggcgacgg ctttgagtgg    7140
ggcgtgctgt tcggctttgg ccccggcctg accgtggagc gcgtcgtcgt ccgctccgtg    7200
ccgatcaagt actgacggag cgacgagtgt gcgtgcgggg ctggcgggag tgggacgccc    7260
tcctcgctcc tctctgttct gaacggaaca atcggccacc ccgcgctacg cgccacgcat    7320
cgagcaacga agaaaacccc ccgatgatag gttgcggtgg ctgccgggat atagatccgg    7380
ccgcacatca aagggcccct ccgcagagag agaagctcct ttcccagcag actccttctg    7440
ctgccaaaac acttctctgt ccacagcaac accaaaggat gaacagatca acttgcgtct    7500
ccgcgtagct tcctcggcta gcgtgcttgc aacaggtccc tgcactatta tcttcctgct    7560
```

```
ttcctctgaa ttatgcggca ggcgagcgct cgctctggcg agcgctcctt cgcgccgccc      7620
tcgctgatcg agtgtacagt caatgaatgg tcgcttttac aggagatcgc ctgctcaagc      7680
gggcgctcaa catgcagagc gtcagcgaga cgggctgtgg cgatcgcgag acggacgagg      7740
ccgcctctgc cctgtttgaa ctgagcgtca gcgctggcta aggggaggga gactcatccc      7800
caggctcgcg ccagggctct gatcccgtct cgggcggtga tcggcgcgca tgactacgac      7860
ccaacgacgt acgagactga tgtcggtccc gacgaggagc cgcgaggc actcccgggc        7920
caccgaccat gtttacaccg accgaaagca ctcgctcgta tccattccgt gcgcccgcac      7980
atgcatcatc ttttggtacc gacttcggtc ttgttttacc cctacgacct gccttccaag      8040
gtgtgagcaa ctcgcccgga catgaccgag ggtgatcatc cggatcccca ggccccagca      8100
gccctgcca gaatggctcg cgcttttcag cctgcaggcc cgtctcccag gtcgacgcaa       8160
cctacatgac caccccaatc tgtcccagac cccaaacacc ctccttccct gcttctctgt      8220
gatcgctgat cagcaacaaa atgggcaaga actacaagtc cctggactcc gtggtggcct      8280
ccgacttcat cgccctgggc atcacgtccg aggtggccga gacgctgcac ggccgcctgg      8340
cggagatcgt gtgcaactac ggcgccgcca cgccccagac gtggatcaac atcgcgaacc      8400
acatcctgtc ccccgacctg cccttctccc tgcaccagat gctgttctac ggctgctaca      8460
aggacttcgg ccccgcgccc ccgcgtgga tccccgaccc cgagaaggtg aagtccacga       8520
acctgggcgc cctgctggag aagcgcggca aggagttcct gggcgtcaag tacaaggacc      8580
ccatctcctc cttctcccac ttccaggagt tctccgtccg caaccccgag gtctactggc      8640
gcacggtgct gatggacgag atgaagatct ccttctccaa ggaccccgag tgcatcctgc      8700
gccgcgacga catcaacaac cccggcggct ccgagtggct gccggcggc tacctgaact       8760
ccgcgaagaa ctgcctgaac gtgaactcca acaagaagct gaacgacacc atgatcgtgt      8820
ggcgcgacga gggcaacgac gacctgcccc tgaacaagct gaccctggac cagctgcgca      8880
agcgcgtgtg gctggtgggc tacgccctgg aggagatggg cctggagaag gctgcgcca       8940
tcgccatcga catgcccatg cacgtggacg ccgtcgtgat ctacctggcc atcgtcctgg      9000
ccggctacgt ggtcgtctcc atcgcggact ccttctccgc gcccgagatc tccacccgcc      9060
tgcgcctgtc caaggccaag gccatcttca cccaggacca catcatccgc ggcaagaagc      9120
gcatccccct gtactcccgc gtcgtggagg ccaagtcccc catggccatc gtgatcccct      9180
gctccggctc caacatcggc gccgagctgc gcgacggcga catctcctgg gactacttcc      9240
tggagcgcgc caaggagttc aagaactgcg agttcacggc ccgcgagcag cccgtcgacg      9300
cctacaccaa catcctgttc tcctccggca ccaccggcga gcccaaggcc atcccctgga      9360
cgcaggccac ccccctgaag gccgccgcg acggctggtc ccacctggac atccgcaagg      9420
gcgacgtcat cgtctggccc accaacctgg gctggatgat gggcccctgg ctggtctacg      9480
cctcctgct gaacgcgcg tccatcgcgc tgtacaacgg ctcccccctg gtgtccggct       9540
tcgccaagtt cgtgcaggac gctaaggtta cgatgctggg cgtggtcccc tccatcgtgc      9600
gctcctggaa gtccaccaac tgcgtgtccg gctacgactg gtccaccatc cgctgcttct      9660
cctcctccgg cgaggcctcc aacgtggacg agtacctgtg gctgatgggc cgcgcgaact      9720
acaagcccgt gatcgagatg tgcggcggca ccgagatcgg cggcgcgttc tccgcgggct      9780
ccttcctgca ggcgcagtcc ctgtcctcct tctcctccca gtgcatgggc tgcaccctgt      9840
acatcctgga caagaacggc tacccatgc ccaagaacaa gcccgcatc ggcgagctgg       9900
ccctgggccc cgtcatgttc ggcgcgtcca agacgctgct gaacggcaac caccacgacg      9960
```

```
tctacttcaa gggcatgccc acgctgaacg gcgaggtcct gcgccgccac ggcgacatct    10020
tcgagctgac ctccaacggc tactaccacg cccacggccg cgccgacgac acgatgaaca    10080
tcggcggcat caagatctcc tccatcgaga tcgagcgcgt gtgcaacgag gtggacgacc    10140
gcgtgttcga cgacggcg atcggcgtgc cccccctggg cggcggcccc gagcagctgg     10200
tcatcttctt cgtcctgaag gactccaacg acaccaccat cgacctgaac cagctgcgcc    10260
tgtccttcaa cctgggcctg cagaagaagc tgaaccccct gttcaaggtg acccgcgtgg    10320
tgcccctgtc ctccctgccc cgcaccgcca ccaacaagat catgcgccgc gtgctgcgcc    10380
agcagttctc ccacttcgag tgacacgccc gcgcggcgca cctgacctgt tctctcgagg    10440
gcgcctgttc tgccttgcga acaagccccc tggagcatgc gtgcatgatc gtctctggcg    10500
ccccgccgcg cggtttgtcg ccctcgcggg cgccgcggcc gcggggcgc attgaaattg      10560 ttgcaaaccc cacctgacag attgagggcc caggcaggaa ggcgttgaga tggaggtaca    10620
ggagtcaagt aactgaaagt ttttatgata actaacaaca aagggtcgtt tctggccagc    10680
gaatgacaag aacaagattc cacatttccg tgtagaggct gccatcgaa tgtgagcggg      10740 cgggccgcgg acccgacaaa accccttacga cgtggtaaga aaaacgtggc gggcactgtc   10800
cctgtagcct gatgaccagc aggagacgat cggaagcatc acagcacacg cttcagacca    10860
tgaagaatat catctataat ggcaactata gtagccgtag cgtctgcgtg ttgggagctg    10920
gagtcgtggg cttgacgacg cgctgcagc tgttgcagga tgtgcctggc gtgcgcgttc     10980
acgtcgtggc tgagaaatat ggcgacgaaa cgttgacggc tggggccggc gggctgtgga    11040
tgccatacgc attgggtacg cggccattgg atgggattga taggcttatg gagggataat    11100
agagtttttg ccggatccaa cgcatgtgga tgcggtatcc cggtgggctg aaagtgtgga    11160
aggatagtgc attggctatt cacatgcact gcccaccct tttggcagga aatgtgccgg     11220
catcgttggt gcaccgatgg ggaaaatcga cgttcgacca ctacatgaag atttatacgt    11280
ctgaagatgc agcgactgcg ggtgcgaaac ggatgacggt ttggtcgtgt atgtcacagc    11340
atgtgctgga tcttgcgggc taactccccc tgccacggcc cattgcaggt gtcatgttga    11400
ctggagggta cgacctttcg tccgtcaaat tcccagagga ggacccgctc tgggccgaca    11460
ttgtgcccac ttttcgccgc ct                                             11482
```

<210> SEQ ID NO 16
<211> LENGTH: 7841
<212> TYPE: DNA
<213> ORGANISM: Artificial Sequence
<220> FEATURE:
<223> OTHER INFORMATION: Plasmid pU061

<400> SEQUENCE: 16

```
ccctcaactg cgacgctggg aaccttctcc gggcaggcga tgtgcgtggg tttgcctcct       60
tggcacggct ctacaccgtc gagtacgcca tgaggcggtg atggctgtgt cggttgccac     120
ttcgtccaga gacggcaagt cgtccatcct ctgcgtgtgt ggcgcgacgc tgcagcagtc     180
cctctgcagc agatgagcgt gactttggcc attcacgca ctcgagtgta cacaatccat     240 tttcttaaa gcaaatgact gctgattgac cagatactgt aacgctgatt cgctccaga     300 tcgcacagat agcgaccatg ttgctgcgtc tgaaaatctg gattccgaat cgaccctgg    360 cgctccatcc atgcaacaga tggcgacact tgttacaatt cctgtcaccc atcggcatgg    420
agcaggtcca cttagattcc cgatcaccca cgcacatctc gctaatagtc attcgttcgt    480
ctcttcgatc aatctcaagt gagtgtgcat ggatcttggt tgacgatgcg gtatgggttt    540
```

| | |
|---|---|
| gcgccgctgg ctgcagggtc tgcccaaggc aagctaaccc agctcctctc cccgacaata | 600 |
| ctctcgcagg caaagccggt cacttgcctt ccagattgcc aataaactca attatggcct | 660 |
| ctgtcatgcc atccatgggt ctgatgaatg gtcacgctcg tgtcctgacc gttcccagc | 720 |
| ctctggcgtc ccctgccccg cccaccagcc cacgccgcgc ggcagtcgct gccaaggctg | 780 |
| tctcggaact atgccaggag ccgctcccgt ctggtcctca cgttcgtgta cggcctggat | 840 |
| cccgaaagg gcggatgcac gtggtgttgc cccgccattg gcgcccacgt ttcaaagtcc | 900 |
| ccggccagaa atgcacagga ccggcccggc tcgcacaggc catgacgaat gcccagattt | 960 |
| cgacagcaaa acaatctgga ataatcgcaa ccattcgcgt tttgaacgaa acgaaaagac | 1020 |
| gctgtttagc acgtttccga tatcgtgggg gccgaagcat gattgggggg aggaaagcgt | 1080 |
| ggccccaagg tagcccattc tgtgccacac gccgacgagg accaatcccc ggcatcagcc | 1140 |
| ttcatcgacg gctgcgccgc acatataaag ccggacgcct tcccgacacg ttcaaacagt | 1200 |
| tttatttcct ccacttcctg aatcaaacaa atcttcaagg aagatcctgc tcttgagcaa | 1260 |
| atgatcgagc aggacggcct gcacgcgggc tccccggcgg cgtgggtcga gcgcctgttc | 1320 |
| ggctacgact gggcgcagca gaccatcggc tgctccgacg ccgcggtgtt tcgcctgtcc | 1380 |
| gcgcagggcc gcccggtgct gttcgtcaag accgacctgt ccggcgccct gaacgagctg | 1440 |
| caggacgagg ccgcccgcct gtcctggctg gccaccaccg gcgtgccgtg cgccgccgtc | 1500 |
| ctggacgtcg tcaccgaggc cggccgcgac tggctgctgc tgggcgaggt cccggggccag | 1560 |
| gacctgctgt cctcccacct ggccccgcg gagaaggtgt ccatcatggc cgacgccatg | 1620 |
| cgccgcctgc acacgctgga ccccgcgacc tgcccgttcg accaccaggc gaagcaccgc | 1680 |
| atcgagcgcg cgcgcacccg catggaggcg ggcctggtgg accaggacga cctggacgag | 1740 |
| gagcaccagg gcctggcccc ggcggagctg ttcgcgcgcc tgaaggcgcg catgccggac | 1800 |
| ggcgaggacc tggtcgtgac gcacggcgac gcgtgcctgc ccaacatcat ggtcgagaac | 1860 |
| ggccgctttt ccggcttcat cgactgcggc cgcctgggcg tcgcggaccg ctaccaggac | 1920 |
| atcgcgctgg ccacccgcga catcgcggag gagctgggcg gcgagtgggc cgaccgcttc | 1980 |
| ctggtcctgt acggcatcgc ggcccccgac tcccagcgca tcgccttcta ccgcctgctg | 2040 |
| gacgagttct tttgacgcag cagcagctcg gatagtatcg acacactctg gacgctggtc | 2100 |
| gtgtgatgga ctgttgccgc cacacttgct gccttgacct gtgaatatcc ctgccgcttt | 2160 |
| tatcaaacag cctcagtgtg tttgatcttg tgtgtacgcg cttttgcgag ttgctagctg | 2220 |
| cttgtgctat ttgcgaatac cacccccagc atccccttcc ctcgtttcat atcgcttgca | 2280 |
| tcccaaccgc aacttatcta cgctgtcctg ctatccctca gcgctgctcc tgctcctgct | 2340 |
| cactgccct cgcacagcct tggtttgggc tccgcctgta ttctcctggt actgcaacct | 2400 |
| gtaaaccagc actgcaatgc tgatgcacgg gaagtagtgg gatgggaaca caaatggaaa | 2460 |
| gctgcgcttg caaaggagat cgcctgctca gcgggcgct caacatgcag agcgtcagcg | 2520 |
| agacgggctg tggcgatcgc gagacggacg aggccgcctc tgccctgttt gaactgagcg | 2580 |
| tcagcgctgg ctaaggggag ggagactcat cccaggctc gcgccagggc tctgatcccg | 2640 |
| tctcgggcg tgatcggcgc gcatgactac gacccaacga cgtacgagac tgatgtcggt | 2700 |
| cccgacgagg agcgccgcga ggcactcccg ggccaccgac catgtttaca ccgaccgaaa | 2760 |
| gcactcgctc gtatccattc cgtgcgcccg cacatgcatc atcttttggt accgacttcg | 2820 |
| gtcttgtttt acccctacga cctgccttcc aaggtgtgag caactcgccc ggacatgacc | 2880 |
| gagggtgatc atccggatcc ccaggcccca gcagcccctg ccagaatggc tcgcgctttc | 2940 |

```
cagcctgcag gcccgtctcc caggtcgacg caacctacat gaccaccca atctgtccca    3000 gaccccaaac accctccttc cctgcttctc tgtgatcgct gatcagcaac aaaatgaacc    3060
cccgcgagaa cttcctgaag tgcttttccc agtacatccc caacaacgcc acgaacctga    3120
agctggtgta cacccagaac aacccgctgt acatgtccgt cctgaactcc acgatccaca    3180
acctgcgctt cacgtccgac accacccca agccctggt gatcgtcacc cctcccacg    3240 tctcccacat ccagggcacg atcctgtgct ccaagaaggt cggcctgcag atccgcaccc    3300
gctccggcgg ccacgactcc gagggcatgt cctacatctc ccaggtgccc ttcgtcatcg    3360
tggacctgcg caacatgcgc tccatcaaga tcgacgtgca ctcccagacc gcgtgggtcg    3420
aggccggcgc gaccctgggc gaggtctact actgggtgaa cgagaagaac gagaacctgt    3480
ccctggcggc gggctactgc ccgaccgtct gcgcgggcgg ccacttcggc ggcggcggct    3540
acggcccgct gatgcgcaac tacggcctgg cggcggacaa catcatcgac gcgcacctgg    3600
tgaacgtgca cggcaaggtg ctggaccgca agtccatggg cgaggacctg ttctgggcgc    3660
tgcgcggcgg cggcgcggag tccttcggca tcatcgtggc gtggaagatc cgcctggtcg    3720
ccgtcccgaa gtccaccatg ttctccgtga agaagatcat ggagatccac gagctggtca    3780
agctggtgaa caagtggcag aacatcgcct acaagtacga caaggacctg ctgctgatga    3840
cgcacttcat cacgcgcaac atcaccgaca accagggcaa gaacaagacc gccatccaca    3900
cgtacttctc ctccgtgttc ctgggcggcg tcgactccct ggtggacctg atgaacaagt    3960
cctttccgga gctgggcatc aagaaaaccg actgccgcca gctgtcctgg atcgacacga    4020
tcatcttcta ctccggcgtg gtcaactacg acacggacaa cttcaacaag gagatcctgc    4080
tggaccgctc cgcgggccag aacggcgcct tcaagatcaa gctggactac gtcaagaagc    4140 ccatcccga gtccgtcttt gtccagatcc tggagaagct gtacgaggag gacatcggcg    4200
ccggcatgta cgccctgtac ccgtacggcg gcatcatgga cgagatctcc gagtccgcga    4260
tccccttccc ccaccgcgcg ggcatcctgt acgagctgtg gtacatctgc tcctgggaga    4320
agcaggagga caacgagaag cacctgaact ggatccgcaa catctacaac ttcatgacgc    4380
cctacgtgtc caagaacccc cgcctggcct acctgaacta ccgcgacctg gacatcggca    4440
tcaacgaccc gaagaaccc aacaactaca cgcaggcgcg catctggggc gagaagtact    4500
tcggcaagaa ctttgaccgc ctggtgaagg tcaagacgct ggtggacccg aacaactttt    4560
tccgcaacga gcagtccatc ccccgctgc cccgccaccg ccactgacac agacgacctt    4620
ggcaggcgtc gggtagggag gtggtggtga tggcgtctcg agcgcatcgc acgcatccaa    4680
cgaccgtata cgcatcgtcc aatgaccgtc ggtgtcctct ctgcctccgt tttgtgagat    4740
gtctcaggct tggtgcatcc tcgggtggcc agccacgttg cgcgtcgtgc tgcttgcctc    4800
tcttgcgcct ctgtggtact ggaaaatatc atcgaggccc gttttttgc tcccatttcc    4860 tttccgctac atcttgaaag caaacgacaa acgaagcagc aagcaaagag cacgaggacg    4920
gtgaacaagt ctgtcacctg tatacatcta tttccccgcg ggtgcaccta ctctctctcc    4980
tgccccggca gagtcagctg ccttacgtga cgcgcttggg aaggaggtga aaactcgctc    5040
gaccgcccgc gtcccgcagg cagcgatgac gtgtgcgtga cctgggtgtt tcgtcgaaag    5100
gccagcaacc ccaaatcgca ggcgatccgg agattgggat ctgatccgag cttggaccag    5160 atccccacg atgcggcacg ggaactgcat cgactcggcg cggaacccag ctttcgtaaa    5220
tgccagattg tgtccgata ccttgatttg ccatcagcga aacaagactt cagcagcgag    5280
cgtatttggc gggcgtgcta ccagggttgc atacattgcc catttctgtc tggaccgctt    5340
```

```
taccggcgca gagggtgagt tgatggggtt ggcaggcatc gaaacgcgcg tgcatggtgt    5400
gtgtgtctgt tttcggctgc acaatttcaa tagtcggatg ggcgacggta gaattgggtg    5460
ttgcgctcgc gtgcatgcct cgccccgtcg ggtgtcatga ccgggactgg aatccccct    5520
cgcgaccctc ctgctaacgc tcccgactct cccgccgcg cgcaggatag actctagttc    5580
aaccaatcga caaatgacgt tcggcgtggc gctgcccgcg atgggccgcg cgtgtccct    5640
gccccgcccc cgcgtggcgg tccgcgcgca gtccgcctcc caggtgctgg agtccgcggc    5700
caccacgaac cagaccgagc cccccgagtc cgacaaccac tccgtggcga cgaagatcct    5760
gaacttcggc aaggcctgct ggaagctgca gcgcccctac accatcatcg cgttcacgtc    5820
ctgcgcctgc ggcctgttcg gcaaggagct gctgcacaac accaacctga tctcctggtc    5880
cctgatgttc aaggccttct tcttcctggt ggcgatcctg tgcatcgcgt ccttcaccac    5940
cacgatcaac cagatctacg acctgcacat cgaccgcatc aacaagcccg acctgcccct    6000
ggcgtccggc gagatctccg tgaacacggc ctggatcatg tccatcatcg tggcgctgtt    6060
cggcctgatc atcaccatca agatgaaggg cggccccctg tacatcttcg gctactgctt    6120
cggcatcttc ggcggcatcg tctactccgt cccccccttc cgctggaagc agaacccctc    6180
cacggccttc ctgctgaact tcctggcgca catcatcacc aacttcacct tctactacgc    6240
ctcccgcgcc gccctgggcc tgccccttcga gctgcgcccc tccttcacgt tcctgctggc    6300
cttcatgaag tccatgggct ccgcgctggc gctgatcaag gacgcctccg acgtggaggg    6360
cgacaccaag ttcggcatct ccacgctggc ctccaagtac ggctcccgca acctgaccct    6420
gttctgctcc ggcatcgtgc tgctgtccta cgtggcggcc atcctggcgg gcatcatctg    6480
gccccaggcg ttcaactcca acgtgatgct gctgtcccac gcgatcctgg ccttctggct    6540
gatcctgcag acccgcgact cgccctgac gaactacgac cccgaggccg gccgccgctt    6600
ctacgagttc atgtggaagc tgtactacgc cgagtacctg gtgtacgtgt tcatctgacg    6660
gagcgacgag tgtgcgtgcg gggctggcgg gagtgggacg ccctcctcgc tcctctctgt    6720
tctgaacgga acaatcggcc accccgcgct acgcgccacg catcgagcaa cgaagaaaac    6780
cccccgatga taggttgcgg tggctgccgg gatatagatc cggccgcaca tcaaagggcc    6840
cctccgccag agaagaagct cctttcccag cagactcctt ctgctgccaa acacttctc    6900
tgtccacagc aacaccaaag gatgaacaga tcaacttgcg tctccgcgta gcttcctcgg    6960
ctagcgtgct tgcaacaggt ccctgcacta ttatcttcct gctttcctct gaattatgcg    7020
gcaggcgagc gctcgctctg gcgagcgctc cttcgcgccg ccctcgctga tcgagtgtac    7080
agtcaatgaa tggtcgcttt tacccatgaa gaatatcatc tataatggca actatagtca    7140
gcgccatgcc acgccctttg atggcttcaa gtacgattac ggtgttggat tgtgtgtttg    7200
ttgcgtagtg tgcatggttt agaataatac acttgatttc ttgctcacgg caatctcggc    7260
ttgtccgcag gttcaacccc atttcggagt ctcaggtcag ccgcgcaatg accagccgct    7320
acttcaagga cttgcacgac aacgccgagg tgagctatgt ttaggacttg attggaaatt    7380
gtcgtcgacg catattcgcg ctccgcgaca gcacccaagc aaaatgtcaa gtgcgttccg    7440
atttgcgtcc gcaggtcgat gttgtgatcg tcggcgccgg atccgccggt ctgtcctgcg    7500
cttacgagct gaccaagcac cctgacgtcc gggtacgcga gctgagattc gattagacat    7560
aaattgaaga ttaaacccgt agaaaaattt gatggtcgcg aaactgtgct cgattgcaag    7620
aaattgatcg tcctccactc cgcaggtcgc catcatcgag cagggcgttg ctcccggcgg    7680
cggcgcctgg ctgggggac agctgttctc ggccatgtgt gtacgtagaa ggatgaattt    7740
```

| cagctggttt tcgttgcaca gctgtttgtg catgatttgt ttcagactat tgttgaatgt | 7800 |
|---|---|
| ttttagattt cttaggatgc atgatttgtc tgcatgcgac t | 7841 |

<210> SEQ ID NO 17
<211> LENGTH: 6795
<212> TYPE: DNA
<213> ORGANISM: Artificial Sequence
<220> FEATURE:
<223> OTHER INFORMATION: Plasmid pU064

<400> SEQUENCE: 17

| ccctcaactg cgacgctggg aaccttctcc gggcaggcga tgtgcgtggg tttgcctcct | 60 |
|---|---|
| tggcacggct ctacaccgtc gagtacgcca tgaggcggtg atggctgtgt cggttgccac | 120 |
| ttcgtccaga gacggcaagt cgtccatcct ctgcgtgtgt ggcgcgacgc tgcagcagtc | 180 |
| cctctgcagc agatgagcgt gactttggcc atttcacgca ctcgagtgta cacaatccat | 240 |
| tttcttaaa gcaaatgact gctgattgac cagatactgt aacgctgatt tcgctccaga | 300 |
| tcgcacagat agcgaccatg ttgctgcgtc tgaaaatctg gattccgaat tcgaccctgg | 360 |
| cgctccatcc atgcaacaga tggcgacact tgttacaatt cctgtcaccc atcggcatgg | 420 |
| agcaggtcca cttagattcc cgatcaccca cgcacatctc gctaatagtc attcgttcgt | 480 |
| ctcttcgatc aatctcaagt gagtgtgcat ggatcttggt tgacgatgcg gtatgggttt | 540 |
| gcgccgctgg ctgcagggtc tgcccaaggc aagctaaccc agctcctctc cccgacaata | 600 |
| ctctcgcagg caaagccggt cacttgcctt ccagattgcc aataaactca attatggcct | 660 |
| ctgtcatgcc atccatgggt ctgatgaatg gtcacgctcg tgtcctgacc gttcccagc | 720 |
| ctctggcgtc ccctgccccg cccaccagcc cacgccgcgc ggcagtcgct gccaaggctg | 780 |
| tctcggaact atgccaggag ccgctcccgt ctggtcctca cgttcgtgta cggcctggat | 840 |
| cccggaaagg gcggatgcac gtggtgttgc cccgccattg gcgcccacgt ttcaaagtcc | 900 |
| ccggccagaa atgcacagga ccggcccggc tcgcacaggc catgacgaat gcccagattt | 960 |
| cgacagcaaa acaatctgga ataatcgcaa ccattcgcgt tttgaacgaa cgaaaagac | 1020 |
| gctgtttagc acgtttccga tatcgtgggg gccgaagcat gattgggggg aggaaagcgt | 1080 |
| ggccccaagg tagcccattc tgtgccacac gccgacgagg accaatcccc ggcatcagcc | 1140 |
| ttcatcgacg gctgcgccgc acatataaag ccggacgcct tcccgacacg ttcaaacagt | 1200 |
| tttatttcct ccacttcctg aatcaaacaa atcttcaagg aagatcctgc tcttgagcaa | 1260 |
| atgatcgagc aggacggcct gcacgcgggc tccccggcgg cgtgggtcga gcgcctgttc | 1320 |
| ggctacgact gggcgcagca gaccatcggc tgctccgacg ccgcggtgtt tcgcctgtcc | 1380 |
| gcgcagggcc gcccggtgct gttcgtcaag accgacctgt ccggcgccct gaacgagctg | 1440 |
| caggacgagg ccgcccgcct gtcctggctg gccaccaccg gcgtgccgtg cgccgccgtc | 1500 |
| ctggacgtcg tcaccgaggc cggccgcgac tggctgctgc tgggcgaggt cccgggccag | 1560 |
| gacctgctgt cctcccacct ggcccccgcg agaaggtgt ccatcatggc cgacgccatg | 1620 |
| cgccgcctgc acacgctgga ccccgcgacc tgcccgttcg accaccaggc gaagcaccgc | 1680 |
| atcgagcgcg cgcgcacccg catggaggcg gcctggtgg accaggacga cctgacgag | 1740 |
| gagcaccagg gcctggcccc ggcggagctg ttcgcgcgcc tgaaggcgcg catgccggac | 1800 |
| ggcgaggacc tggtcgtgac gcacggcgac gcgtgcctgc ccaacatcat ggtcgagaac | 1860 |
| ggccgctttt ccggcttcat cgactgcggc cgcctgggcg tcgcggaccg ctaccaggac | 1920 |
| atcgcgctgg ccacccgcga catcgcggag gagctgggcg gcgagtgggc cgaccgcttc | 1980 |

| | |
|---|---|
| ctggtcctgt acggcatcgc ggcccccgac tcccagcgca tcgccttcta ccgcctgctg | 2040 |
| gacgagttct tttgacgcag cagcagctcg gatagtatcg acacactctg gacgctggtc | 2100 |
| gtgtgatgga ctgttgccgc cacacttgct gccttgacct gtgaatatcc ctgccgcttt | 2160 |
| tatcaaacag cctcagtgtg tttgatcttg tgtgtacgcg cttttgcgag ttgctagctg | 2220 |
| cttgtgctat ttgcgaatac caccccagc atccccttcc ctcgtttcat atcgcttgca | 2280 |
| tcccaaccgc aacttatcta cgctgtcctg ctatccctca cgctgctcc tgctcctgct | 2340 |
| cactgcccct cgcacagcct tggtttgggc tccgcctgta ttctcctggt actgcaacct | 2400 |
| gtaaaccagc actgcaatgc tgatgcacgg aagtagtgg gatgggaaca caaatggaaa | 2460 |
| gctgcgcttg caaggagat caaaaacgcc tgagacactt gcccaggatt gaaactccct | 2520 |
| gaagggacca ccaggggccc tgagttgttc cttcccccg tggcgagctg ccagccaggc | 2580 |
| tgtacctgtg atcggggctg gcgggaaaac aggcttcgtg tgctcaggtt atgggaggtg | 2640 |
| caggacagct cattaaacgc caacaatcgc acaattcatg gcaagctaat cagttatttc | 2700 |
| ccattaacga gctataattg tcccaaaatt ctggtctacc ggggtgatc cttcgtgtac | 2760 |
| gggcccttcc ctcaaccta ggtatgcgca catgcggtcg ccgcgcaacg cgcgcgaggg | 2820 |
| ccgagggttt gggacgggcc gtcccgaaat gcagttgcac ccggatgcgt ggcacctttt | 2880 |
| ttgcgataat ttatgcaatg gactgctctg caaaattctg gctctgtcgc caaccctagg | 2940 |
| atcagcggtg taggatttcg taatcattcg tcctgatggg gagctaccga ctgccctagt | 3000 |
| atcagcccga ctgcctgacg ccagcgtcca cttttgtgca cacattccat tcgtgcccaa | 3060 |
| gacatttcat tgtggtgcga agcgtcccca gttacgctca cctgatcccc aacctcctta | 3120 |
| ttgttctgtc gacagagtgg gcccagagc cggtcgcagc caatggccgt caagcacctg | 3180 |
| atcgtgctga agttcaagga cgagatcacg gaggcccaga aggaggagtt cttcaagacc | 3240 |
| tacgtcaacc tggtgaacat catccccgcc atgaaggacg tgtactgggg caaggacgtc | 3300 |
| acgcagaaga acaaggagga gggctacacg cacatcgtgg aggtcacctt cgagtccgtg | 3360 |
| gagacgatcc aggactacat catccacccc gcgcacgtgg gcttcggcga cgtgtaccgc | 3420 |
| tccttctggg agaagctgct gatcttcgac tacacccccc gcaagtgaca cagacgacct | 3480 |
| tggcaggcgt cgggtaggga ggtggtggtg atggcgtctc gagcgcatcg cacgcatcca | 3540 |
| acgaccgtat acgcatcgtc caatgaccgt cggtgtcctc tctgcctccg ttttgtgaga | 3600 |
| tgtctcaggc ttggtgcatc ctcgggtggc cagccacgtt gcgcgtcgtg ctgcttgcct | 3660 |
| ctcttgcgcc tctgtggtac tggaaaatat catcgaggcc cgttttttg ctcccatttc | 3720 |
| cttttccgcta catcttgaaa gcaaacgaca aacgaagcag caagcaaaga gcacgaggac | 3780 |
| ggtgaacaag tctgtcacct gtatacatct atttccccgc gggtgcacct actctctctc | 3840 |
| ctgccccggc agagtcagct gccttacgtg acgcgcttgg gaaggaggtg aaaactcgct | 3900 |
| cgaccgcccg cgtcccgcag gcagcgatga cgtgtgcgtg acctgggtgt tcgtcgaaa | 3960 |
| ggccagcaac cccaaatcgc aggcgatccg gagattggga tctgatccga gcttggacca | 4020 |
| gatcccccac gatgcggcac gggaactgca tcgactcggc gcggaaccca gctttcgtaa | 4080 |
| atgccagatt ggtgtccgat accttgattt gccatcagcg aaacaagact tcagcagcga | 4140 |
| gcgtatttgg cgggcgtgct accagggttg catacattgc ccatttctgt ctggaccgct | 4200 |
| ttaccggcgc agagggtgag ttgatggggt tggcaggcat cgaaacgcgc gtgcatggtg | 4260 |
| tgtgtgtctg ttttcggctg cacaatttca atagtcggat gggcgacggt agaattgggt | 4320 |
| gttgcgctcg cgtgcatgcc tcgccccgtc gggtgtcatg accgggactg gaatcccccc | 4380 |

-continued

```
tcgcgaccct cctgctaacg ctcccgactc tcccgcccgc gcgcaggata gactctagtt      4440
caaccaatcg acaaatgaac cacctgcgcg cggagggccc ggcgtccgtg ctggccatcg      4500
gcaccgccaa ccccgagaac atcctgctgc aggacgagtt ccccgactac tacttccgcg      4560
tgaccaagtc cgagcacatg acccagctga aggagaagtt tcgcaagatc tgcgacaagt      4620
ccatgatccg caagcgcaac tgctttctga acgaggagca cctgaagcag aaccccccgcc     4680 tggtcgagca cgagatgcag acgctggacg cccgccagga catgctggtg gtcgaggtcc      4740
cgaagctggg caaggacgcc tgcgccaagg ccatcaagga gtggggccag cccaagtcca      4800
agatcaccca cctgatcttc acctccgcct ccaccacgga catgcccggc gccgactacc      4860
actgcgccaa gctgctgggc ctgtcccect ccgtgaagcg cgtcatgatg taccagctgg      4920
gctgctacgg cggcggcacc gtcctgcgca tcgccaagga catcgcggag aacaacaagg      4980
gcgcgcgcgt gctggcggtc tgctgcgaca tcatggcctg cctgtttcgc ggcccctccg      5040
agtccgacct ggagctgctg gtgggccagg cgatctttgg cgacggcgcc gcggcggtga      5100
tcgtcggcgc cgagcccgac gagtccgtcg gcgagcgccc catcttcgag ctggtgtcca      5160
ccggccagac catcctgccg aactccgagg gcacgatcgg cggccacatc cgcgaggccg      5220
gcctgatctt cgacctgcac aaggacgtgc ccatgctgat ctccaacaac atcgagaagt      5280
gcctgatcga ggccttcacg ccgatcggca tctccgactg gaactccatc ttctggatca      5340
cccacccggg cggcaaggcg atcctggaca aggtggagga gaagctgcac ctgaagtccg      5400
acaagttcgt ggactcccgc cacgtgctgt ccgagcacgg caacatgtcc tcctccaccg      5460
tcctgttcgt gatggacgag ctgcgcaagc gctccctgga ggagggcaag tccaccacgg      5520
gcgacggctt tgagtggggc gtgctgttcg gctttggccc cggcctgacc gtggagcgcg      5580
tcgtcgtccg ctccgtgccg atcaagtact gacggagcga cgagtgtgcg tgcggggctg      5640
gcgggagtgg gacgccctcc tcgctcctct ctgttctgaa cggaacaatc ggccaccccg      5700
cgctacgcgc cacgcatcga gcaacgaaga aaaccccccg atgataggtt gcggtggctg      5760
ccgggatata gatccggccg cacatcaaag ggcccctccg ccagagaaga agctcctttc      5820
ccagcagact ccttctgctg ccaaaacact tctctgtcca cagcaacacc aaaggatgaa      5880
cagatcaact gcgtctccg cgtagcttcc tcggctagcg tgcttgcaac aggtccctgc      5940
actattatct tcctgctttc ctctgaatta tgccggcaggc gagcgctcgc tctggcgagc      6000
gctccttcgc gccgccctcg ctgatcgagt gtacagtcaa tgaatggtcg cttttaccca      6060
tgaagaatat catctataat ggcaactata gtcagcgcca tgccacgccc tttgatggct      6120
tcaagtacga ttacggtgtt ggattgtgtg tttgttgcgt agtgtgcatg gtttagaata      6180
atacacttga tttcttgctc acggcaatct cggcttgtcc gcaggttcaa ccccatttcg      6240
gagtctcagg tcagccgcgc aatgaccagc cgctacttca aggacttgca cgacaacgcc      6300
gaggtgagct atgtttagga cttgattgga aattgtcgtc gacgcatatt cgcgctccgc      6360
gacagcaccc aagcaaaatg tcaagtgcgt tccgatttgc gtccgcaggt cgatgttgtg      6420
atcgtcggcg ccgatccgc cggtctgtcc tgcgcttacg agctgaccaa gcaccctgac      6480
gtccgggtac gcgagctgag attcgattag acataaattg aagattaaac ccgtagaaaa      6540
atttgatggt cgcgaaactg tgctcgattg caagaaattg atcgtcctcc actccgcagg      6600
tcgccatcat cgagcagggc gttgctcccg gcggcggcgc ctggctgggg ggacagctgt      6660
tctcggccat gtgtgtacgt agaaggatga atttcagctg gttttcgttg cacagctgtt      6720
```

```
tgtgcatgat ttgtttcaga ctattgttga atgtttttag atttcttagg atgcatgatt    6780
tgtctgcatg cgact                                                     6795
```

NEUROTRANSMITTERS AND METHODS OF MAKING THE SAME

This application is continuation of U.S. application Ser. No. 15/971,893 filed May 4, 2018, which claims priority to U.S. provisional application Ser. No. 62/501,747 filed May 5, 2017.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "PUR0005_ST25.txt", a creation date of Apr. 28, 2017, and a size of 97 kilobytes. The Sequence Listing filed via EFS-Web is part of the specification and is incorporated in its entirety by reference herein.

BACKGROUND OF THE INVENTION

Neurotransmitters are chemical compounds that act as chemical messengers enabling neurotransmission. Neurotransmitters transmit signals across a chemical synapse from one neuron (nerve cell) to another "target" neuron, muscle cell, or gland cell. Neurotransmitters are released from synaptic vesicles in synapses into the synaptic cleft, where they are received by receptors on the target cells. Many neurotransmitters are synthesized from simple and plentiful precursors such as amino acids, which are readily available from the diet and only require a small number of biosynthetic steps for conversion. The exact number of neurotransmitters is unknown, but more than 100 chemical messengers have been uniquely identified.

One class of neurotransmitters are the cannabinoids which are a diverse class of chemical compounds that act on cannabinoid receptors inducing intracellular cascades that affect neural activity and alter neurotransmitter release from cells in the brain. Humans and other animals naturally make cannabinoids that act on these receptors. Other neurotransmitters that can act on the cannabinoid receptors are phytocannabinoids made in plants and synthetic or artificial cannabinoids.

There are two known types of cannabinoid receptors termed $CB_1$ and $CB_2$. Both CB1 and CB2 signal through the transducing G proteins, $G_i$ and $G_o$ and their activation by cannabinoids or other agonists causes the inhibition of adenylyl cyclase activity, the closing of voltage-gated calcium channels, the opening of inwardly rectifying potassium channels, and the stimulation of mitogen-activated protein kinases such as ERK and focal adhesion kinases (FAKs) (Mackie, K. 2006. Cannabinoid receptors as therapeutic targets. Annual Review of Pharmacology and Toxicology 46:101-122). The cannabinoid receptors are the most plentiful G protein-coupled receptor in the human brain. $CB_1$ receptors are found primarily in the brain, more specifically in the basal ganglia and in the limbic system, including the hippocampus and the striatum. In mammals, high concentrations of CB1 receptors are found in areas that regulate appetite, memory, fear extinction, and motor responses. They are also found in the cerebellum and in both male and female reproductive systems. $CB_1$ is also found in the human anterior eye and retina. CB1 is also found in a number of other non-neural tissues, including gastrointestinal tract, adipocytes, liver, and skeletal muscle. $CB_2$ receptors are predominantly found in the immune system, or immune-derived cells with the greatest density in the spleen. $CB_2$ receptors are also expressed by a subpopulation of microglia, osteoclasts, and osteoblasts in the human cerebellum. $CB_2$ receptors may be responsible for anti-inflammatory and other therapeutic effects of *Cannabis* seen in animal models.

SUMMARY OF THE INVENTION

In an aspect, the disclosure describes methods for making neurotransmitters using microalgae. In some embodiments, the neurotransmitters made by the microalgae are cannabinoids such as, for example, cannabigerolic acid (CBGA), cannabichromenic acid (CBCA), cannabidiolic acid (CBDA), tetrahydrocannabinolic acid (THCA), cannabigerovarinic acid (CBGVA), cannabidivarinic acid (CBDVA), cannabichromevarinic acid (CBCVA), or tetrahydrocannabivarinic acid (THCVA). When hexanoic acid (or other six carbon precursor) is used as precursor the microalgae can make CBGA, CBCA, CBDA and THCA. When butyric acid (or other four carbon precursor) is used as precursor the microalgae can make CBGVA, CBDVA, CBCVA, and THCVA.

In an aspect, the microalgae are engineered to express hexanoyl-CoA synthase, 3,5,7-trioxododecanoyl-CoA synthase, olivetolic acid cyclase (or 3,5,7-trioxododecanoyl-CoA CoA-lyase), and geranyl-diphosphate:olivetolate geranyltransferase. These enzymes make cannabigerolic acid (CBGA) from hexanoic acid (or hexanoate) as follows. Hexanoic acid is reacted with CoA to make hexanoyl-CoA by the enzyme hexanoyl-CoA synthase. Hexanoyl-CoA and three malonyl-CoA react to make 3,5,7-trioxododecanoyl-CoA using the enzyme 3,5,7-trioxododecanoyl-CoA synthase. 3,5,7-trioxododecanoyl-CoA reacts to form olivetolic acid using the enzyme 3,5,7-trioxododecanoyl-CoA CoA-lyase (or olivetolic acid cyclase). Olivetolic acid and geranylpyrophosphate react to form cannabigerolic acid (CBGA) using the enzyme geranyl-diphosphate:olivetolate geranyltransferase. These enzymes can also make cannabigerovarinic acid (CBGVA) from butyric acid (or butyrate) as follows. Butyric acid and CoA react to make butyryl-CoA using the enzyme hexanoyl-CoA synthase. Butyryl-CoA and 3 malonyl-CoA react to make 3,5,7-trioxodecanoyl-CoA using the enzyme 3,5,7-trioxododecanoyl-CoA synthase. 3,5,7-trioxodecanoyl-CoA reacts to form divarinic acid using the enzyme olivetolic acid cyclase. Divarinic acid and geranylpyrophosphate react to form cannabigerovarinic acid (CBGVA) using the enzyme geranyl-diphosphate:olivetolate geranyltransferase.

In an alternative aspect, the microalgae are engineered to express one or more substitute enzymes for hexanoyl-CoA synthase, 3,5,7-trioxododecanoyl-CoA synthase, 3,5,7-trioxododecanoyl-CoA CoA-lyase (or olivetolic acid cyclase), and geranyl-diphosphate:olivetolate geranyltransferase. These microalgae with the one or more substitute enzymes can also be used to make CBGA from hexanoic acid and/or CBGVA from butyric acid.

In one aspect, the microalgae are also engineered to express cannabichromenic acid synthase. In this aspect, the microalgae make cannabichromenic acid (CBCA) from CBGA, and/or cannabichromevarinic acid (CBCVA) from CBGVA using the enzyme cannabichromenic acid synthase.

In one aspect, the microalgae are also engineered to express cannabidiolic-acid synthase. In this aspect, the microalgae make cannabidiolic acid (CBDA) from CBGA, and/or cannabidivarinic acid (CBDVA) from CBGVA using the enzyme cannabidiolic-acid synthase.

In one aspect, the microalgae are also engineered to express Δ1-tetrahydrocannabinolic acid synthase. In this aspect, the microalgae make tetrahydrocannabinolic acid (THCA) from CBGA, and/or tetrahydrocannabivarinic acid (THCVA) from CBGVA using the enzyme Δ1-tetrahydrocannabinolic acid synthase.

In an alternative aspect, the microalgae are engineered to express two or more of cannabichromenic acid synthase, cannabidiolic-acid synthase, and Δ1-tetrahydrocannabinolic acid synthase.

The disclosure also describes nucleic acids encoding the enzymes described above. These nucleic acids include expression constructs for expressing the enzymes in microalgae. The nucleic acids encoding the enzymes can be codon optimized for the microalgae. The nucleic acids can encode a hexanoyl-CoA synthase that is SEQ ID NO: 1, a 3,5,7-trioxododecanoyl-CoA synthase that is SEQ ID NO: 2, a 3,5,7-trioxododecanoyl-CoA CoA-lyase (olivetolic acid cyclase) that is SEQ ID NO: 3, a geranyl-diphosphate: olivetolate geranyltransferase that is SEQ ID NO: 4, a cannabichromenic acid synthase that is SEQ ID NO: 5, a cannabidiolic acid synthase that is SEQ ID NO: 6, and/or a Δ1-tetrahydrocannabinolic acid synthase that is SEQ ID NO: 7. The nucleic acids can encode a polypeptide that has 70%, 80%, 90%, 95% or 99% sequence identity with one of SEQ ID NOs: 1-7. Nucleic acids may also include those that hybridize under stringent hybridization conditions to a nucleic acid encoding one of SEQ ID NOs: 1-7. The nucleic acids can encode one or more of hexanoyl-CoA synthase, 3,5,7-trioxododecanoyl-CoA synthase, olivetolic acid cyclase, geranyl-diphosphate:olivetolate geranyltransferase, cannabichromenic acid synthase, cannabidiolic acid synthase, and Δ1-tetrahydrocannabinolic acid synthase; or the nucleic acids can encode one of SEQ ID NOs: 1-7; hybridize under stringent hybridization conditions with a nucleic acid encoding one of SEQ ID NOs: 1-7; or encode a polypeptide that has 70%, 80%, 90%, 95% or 99% sequence identity with one of SEQ ID NOs: 1-7.

In an aspect, the polypeptide disclosed include one or more of hexanoyl-CoA synthase, 3,5,7-trioxododecanoyl-CoA synthase, olivetolic acid cyclase, geranyl-diphosphate: olivetolate geranyltransferase, cannabichromenic acid synthase, cannabidiolic-acid synthase, and Δ1-tetrahydrocannabinolic acid synthase. Polypeptides can include polypeptides that have 70%, 80%, 90%, 95% or 99% sequence identity with one of SEQ ID NOs: 1-7. Polypeptides can include polypeptides encoded by nucleic acids that hybridize under stringent hybridization conditions with a nucleic acid encoding one of SEQ ID NOs: 1-7. Polypeptides can include hexanoyl-CoA synthase, 3,5,7-trioxododecanoyl-CoA synthase, olivetolic acid cyclase, geranyl-diphosphate:olivetolate geranyltransferase, cannabichromenic acid synthase, cannabidiolic-acid synthase, and Δ1-tetrahydrocannabinolic acid synthase; or one of SEQ ID NOs: 1-7; or polypeptides encoded by nucleic acids that hybridize under stringent hybridization conditions with a nucleic acid encoding one of SEQ ID NOs: 1-7; or polypeptides that have 70%, 80%, 90%, 95% or 99% sequence identity with one of SEQ ID NOs: 1-7. The coding sequence can comprise a plastid targeting sequence from microalgae, and the microalgae can be a species of the genus Prototheca or *Chlorella* as well as other genera from the family Chlorellaceae. The plastid targeting sequence can have at least 20, 25, 35, 45, or 55% amino acid sequence identity to one or more of SEQ ID NOs: 11-14 and can be capable of targeting a protein encoded by an exogenous gene not located in the plastid genome to the plastid.

Host cells can contain the nucleic acids and/or polypeptides described above and herein. The host cell can be an algae species and/or a photosynthetic, or non-photosynthetic, microorganism from *Agmenellum, Amphora, Anabaena, Ankistrodesmus, Asterochloris, Asteromonas, Astephomene, Auxenochlorella, Basichlamys, Botryococcus, Botryokoryne, Boekelovia, Borodinella, Brachiomonas, Catena, Carteria, Chaetoceros, Chaetophora, Characiochloris, Characiosiphon, Chlainomonas, Chlamydomonas, Chlorella, Chlorochytrium, Chlorococcum, Chlorogonium, Chloromonas, Chrysosphaera, Closteriopsis, Cricosphaera, Cryptomonas, Cyclotella, Dictyochloropsis, Dunaliella, Ellipsoidon, Eremosphaera, Eudorina, Euglena, Fragilaria, Floydiella, Friedmania, Haematococcus, Hafniomonas, Heterochlorella, Gleocapsa, Gloeothamnion, Gonium, Halosarcinochlamys, Hymenomonas, Isochrysis, Koliella, Lepocinclis, Lobocharacium, Lobochlamys, Lobomonas, Lobosphaera, Lobosphaeropsis, Marvania, Monoraphidium, Myrmecia, Nannochloris, Nannochloropsis, Navicula, Nephrochloris, Nitschia, Nitzschia, Ochromonas, Oocystis, Oogamochlamys, Oscillatoria, Pabia, Pandorina, Parietochloris, Pascheria, Phacotus, Phagus, Phormidium, Platydorina, Platymonas, Pleodorina, Pleurochrysis, Polulichloris, Polytoma, Polytomella, Prasiola, Prasiolopsis, Prasiococcus, Prototheca, Pseudochlorella, Pseudocarteria, Pseudotrebouxia, Pteromonas, Pyrobotrys, Rosenvingiella, Scenedesmus, Schizotrichium, Spirogyra, Stephanosphaera, Tetrabaena, Tetraedron, Tetraselmis, Thraustochytrium, Trebouxia, Trochisciopsis, Ulkenia, Viridiella, Vitreochlamys, Volvox, Volvulina, Vulcanochloris, Watanabea,* or *Yamagishiella*. The host cell can be *Botryococcus braunii, Prototheca krugani, Prototheca moriformis, Prototheca portoricensis, Prototheca stagnora, Prototheca wickerhamii, Prototheca zopfii,* or *Schizotrichium* sp. The host cell can be a fungi species from *Aciculoconidium, Ambrosiozyma, Arthroascus, Arxiozyma, Ashbya, Aspergillus, Babjevia, Bensingtonia, Botryoascus, Botryozyma, Brettanomyces, Bullera, Bulleromyces, Candida, Chlamydomonas, Chrysosporium, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Fusarium, Galactomyces, Geotrichum, Guilliermondella, Hanseniaspora, Hansenula, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Neotyphodium, Neurospora, Ogataea, Oosporidium, Pachysolen, Penicillium, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichoderma, Trichosporiella, Trichosporon, Trigonopsis, Tsuchiyaea, Udeniomyces, Waltomyces, Wickerhamia, Wickerhamiella, Williopsis, Xanthophyllomyces, Yamadazyma, Yarrowia, Zygoascus, Zygosaccharomyces, Zygowilliopsis,* and *Zygozyma*, among others. The fungi host cell can be *Candida albicans, Chrysosporium lucknowense, Fusarium graminearum, Fusarium venenatum, Hansenula polymorpha, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis,*

*Streptomyces ambofaciens, Streptomyces aureofaciens, Streptomyces aureus, Saccaromyces bayanus, Saccaromyces boulardi, Saccharomyces cerevisiae, Schizosaccharomyces pompe, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Trichoderma reesei* and *Xanthophyllomyces dendrorhous* (formerly *Phaffia rhodozyma*), or a filamentous fungi, e.g. *Trichoderma, Aspergillus* sp., including *Aspergillus nidulans, Aspergillus niger, Aspergillus oryzae, Aspergillus phoenicis, Aspergillus carbonarius*. The host cell can be a strain of the species *Prototheca moriformis, Prototheca krugani, Prototheca stagnora* or *Prototheca zopfii* and in other embodiment the cell has a 16S rRNA sequence with at least 70, 75, 80, 85, 90, 95 or 99% sequence identity (Ewing A, et al (2014) *J. Phycol.* 50: 765-769).

In an aspect, oils obtained from algae host cells and methods of obtaining the oils are disclosed by the specification. For example, a method for producing an oil or oil-derived product involves cultivating the host cell and extracting the oil, optionally wherein the cultivation is heterotrophic growth on sugar. Optionally, a fatty acid, cannabinoid, chemical or other oil-derived product can be produced from the oil. Optionally, the oil is produced in microalgae and can lack C24-alpha sterols.

In additional embodiments the invention include cannabinoid oil compositions as well as cells containing cannabinoid oil compositions comprising a lipid profile of at least 1% cannabinoid and one or more of the following attributes: 0.1-0.4 micrograms/ml total carotenoids, less than 0.4 micrograms/ml total carotenoids, less than 0.001 micrograms/ml lycopene; less than 0.02 micrograms/ml beta carotene, less than 0.02 milligrams of chlorophyll per kilogram of oil; 0.40-0.60 milligrams of gamma tocopherol per 100 grams of oil; 0.2-0.5 milligrams of total tocotrienols per gram of oil, less than 0.4 milligrams of total tocotrienols per gram of oil, 4-8 mg per 100 grams of oil of campesterol, and 40-60 mg per 100 grams of oil of stigmasterol.

BRIEF DESCRIPTION OF THE DRAWINGS

FIG. 2 illustrates biosynthesis of olivetolic acid in *Prototheca moriformis*. HPLC chromatograms (AU 270 nM) of representative wild-type R2 (FIG. 2A) and R2 transformed with pU092 (SEQ ID NO: 15) (FIG. 2B) strains demonstrate biosynthesis of olivetolic acid transgenic R2-pU092 microalgae. Elution of olivetolic acid at ca. 2.8 min is confirmed by MS (FIG. 2C).

DETAILED DESCRIPTION OF THE INVENTION

Figure 1:
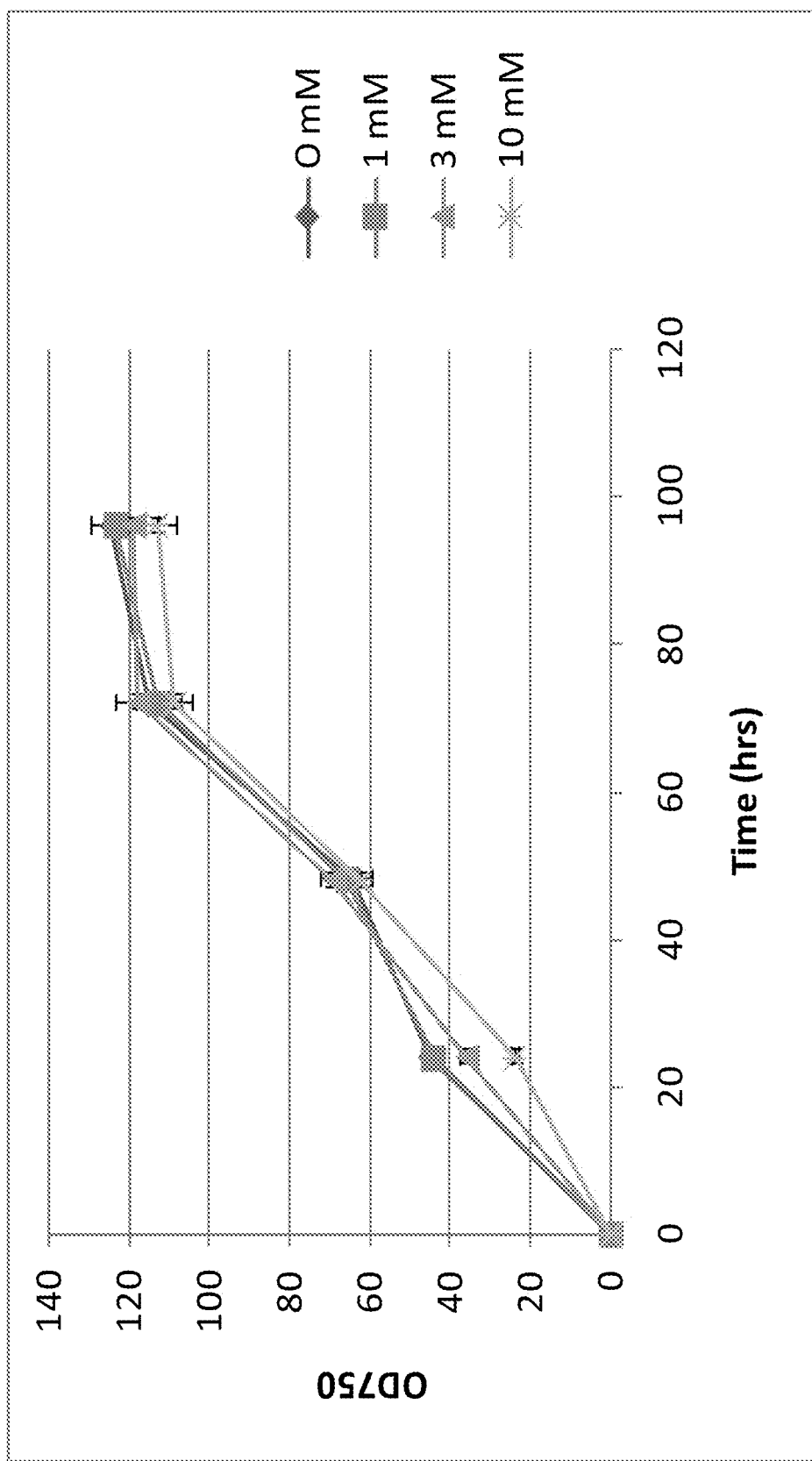
FIG. 1 illustrates the time course for growth of *Prototheca moriformis* strain UTEX1435 grown on sugar supplemented with indicated concentrations of hexanoic acid.

Before the various embodiments are described, it is to be understood that the teachings of this disclosure are not limited to the particular embodiments described, and as such can vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. Numerical limitations given with respect to concentrations or levels of a substance are intended to be approximate, unless the context clearly dictates otherwise. Thus, where a concentration is indicated to be (for example) 10 μg, it is intended that the concentration be understood to be at least approximately or about 10 μg.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

As used herein, "alcanoyl-CoA" is an aliphatic carbonyl compound having a coenzyme A moiety bonded to the carbon atom of the carbonyl group through a sulfide bridge. Preferred alkanoyl CoA compounds comprise from 2 to 6 carbon atoms in the aliphatic carbonyl part of the compound. More preferably, the alkanoyl CoA is CoA-S—C(O)—(CH2)n-CH3, where n is an integer from 0 to 4. Examples of alkanoyl CoA compounds include acetyl CoA, butyryl CoA, and hexanoyl CoA. Use of acetyl CoA provides a methyl side chain to the resulting aromatic polyketide; use of butyryl-CoA provides a propyl side chain; and use of hexanoyl-CoA provides a pentyl side chain.

As used herein, "codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome.

As used herein, "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest among members of related gene sequences. For each position of a gene, the consensus sequence gives the amino acid that is most abundant in that position in a multiple sequence alignment (MSA).

As used herein, "control sequence" refers to components, which are used for the expression of a polynucleotide and/or polypeptide. Each control sequence may be native or foreign to the nucleic acid sequence encoding the polypeptide. Such control sequences may include, but are not limited to, some or all of the following: a promoter, inducible or constitutive, an enhancer, an operator, an attenuator, a ribosome binding site (e.g., shine-dalgarno sequence), a leader, a polyadenylation sequence, a pro-peptide sequence, a signal peptide sequence which directs the protein to which they are attached to a particular location in or outside the cell, and a transcription terminator. At a minimum, the control sequences include a promoter and transcriptional signals, and where appropriate, translational start and stop signals.

As used herein, an "effective amount" refers to an amount of a compound, formulation, material, or composition, as described herein effective to achieve a particular biological result.

As used herein, "expression vector" or "expression construct" or "recombinant DNA construct" refer to a nucleic acid construct, that has been generated recombinantly or synthetically via human intervention, including by recombinant means or direct chemical synthesis, with a series of specified nucleic acid elements that permit transcription and/or translation of a particular nucleic acid in a host cell. The expression vector can be part of a plasmid, virus, or nucleic acid fragment. Typically, the expression vector includes a nucleic acid to be transcribed operably linked to a promoter. The expression vector can exist in a host cell as either an episomal or integrated vector/construct.

As used herein, "exogenous gene" refers to a nucleic acid that codes for the expression of an RNA and/or protein that has been introduced ("transformed") into a cell. A transformed cell may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome or as an episomal molecule.

As used herein, "expeller pressing" is a mechanical method for extracting oil from raw materials such as soybeans and rapeseed. An expeller press is a screw type machine, which presses material through a caged barrel-like cavity. Raw materials enter one side of the press and spent cake exits the other side while oil seeps out between the bars in the cage and is collected. The machine uses friction and continuous pressure from the screw drives to move and compress the raw material. The oil seeps through small openings that do not allow solids to pass through. As the raw material is pressed, friction typically causes it to heat up.

As used herein, "heterologous" polynucleotide or polypeptide refers to any polynucleotide that is introduced into a host cell by laboratory techniques, or a polynucleotide that is foreign to a host cell. As such, the term includes polynucleotides that are removed from a host cell, subjected to laboratory manipulation, and then reintroduced into a host cell. The introduced polynucleotide can express a heterologous polypeptide. Heterologous polypeptides are those polypeptides that are foreign to the host cell being utilized.

As used herein, "isolated polypeptide" refers to a polypeptide which is substantially separated from other components that naturally accompany it, e.g., protein, lipids, and polynucleotides. The term embraces polypeptides which have been removed or purified from their naturally-occurring environment or expression system (e.g., host cell or in vitro synthesis). The polypeptides may be present within a cell, present in the cellular medium, or prepared in various forms, such as lysates or isolated preparations.

As used herein, "lipids" are a class of molecules that are soluble in nonpolar solvents (such as ether and chloroform) and are relatively or completely insoluble in water. Lipid molecules have these properties, because they consist largely of long hydrocarbon tails which are hydrophobic in nature. Examples of lipids include fatty acids (saturated and unsaturated); glycerides or glycerolipids (such as monoglycerides, diglycerides, triglycerides or neutral fats, and phosphoglycerides or glycerophospholipids); nonglycerides (sphingolipids, sterol lipids including cholesterol and steroid hormones, prenol lipids including terpenoids, fatty alcohols, waxes, and polyketides), composite prenol lipids (terpenophenolic cannabinoids); and complex lipid derivatives (sugar-linked lipids, or glycolipids, and protein-linked lipids).

As used herein, the terms "natural oil" or "natural fat" are used interchangeably and are defined to mean a total lipid predominantly composed of hydrocarbon oils of tryglyceride and/or terpenoid nature, where the oil has not undergone blending with another natural or synthetic oil, or fractionation so as to substantially alter the composition or the structure of hydrocarbons.

As used herein, "microalgae" refers to a eukaryotic microbial organism that contains a chloroplast or plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include cells such as *Chlorella, Dunaliella,* and *Prototheca*. Microalgae also include other microbial photosynthetic organisms that exhibit cell-cell adhesion, such as *Agmenellum, Anabaena,* and *Pyrobotrys*. Microalgae also include obligate heterotrophic microorganisms that have lost the ability to perform photosynthesis, such as certain dinoflagellate algae species, thraustochytrids such as *Schizotrichium* and species of the genus *Prototheca*.

As used herein, "microorganism" and "microbe" are used interchangeably and refer to microscopic, unicellular organisms.

As used herein, "naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

As used herein, "neurotransmitter" refers to molecules that interact with receptors found on neurons. Neurotransmitters may be agonists or antagonists of a receptor. Neurotransmitters may inhibit re-uptake of other neurotransmitters by neurons or cause a cell to have less neurotransmitter (make less or reduce the half-life). Neurotransmitters may be naturally occurring, recombinantly made, or otherwise manufactured.

As used herein, "operably linked" and "operable linkage" refer to a configuration in which a control sequence or other nucleic acid is appropriately placed (i.e., in a functional relationship) at a position relative to a polynucleotide of interest such that the control sequence or other nucleic acid can interact with the polynucleotide of interest. In the case of a control sequence, operable linkage means the control sequence directs or regulates the expression of the polynucleotide and/or polypeptide of interest. In the case of polypeptides, operably linked refers to a configuration in which a polypeptide is appropriately placed at a position relative to a polypeptide of interest such that the polypeptide can interact as desired with the polypeptide of interest.

As used herein, "percentage of sequence identity" and "percentage homology" are used interchangeably herein to define to comparisons among polynucleotides or polypeptides, and are determined by comparing two optimally aligned sequences over a comparison window, where the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, *Adv Appl Math.* 2:482, 1981; by the homology alignment algorithm of Needleman and Wunsch, *J Mol Biol.* 48:443, 1970; by the search for similarity method of Pearson and Lipman, *Proc Natl Acad Sci. USA* 85:2444, 1988; by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Greene Publishing Associates, Inc. and John Wiley & Sons, Inc., (1995 Supplement). Examples of algorithms that are suitable for determining percent sequence identity and sequence similarity are the BLAST and BLAST 2.0 algorithms, which are described in Altschul et al., *J. Mol. Biol.* 215:403-410, 1990; and Altschul et al., *Nucleic Acids Res.* 25(17):3389-3402, 1977; respectively. Software for performing BLAST analyses is publicly available through the National Center for Biotechnology Information website. BLAST for nucleotide sequences can use the BLASTN program with default parameters, e.g., a word length (W) of 11, an expectation (E) of 10, M=5, N=−4, and a comparison of both strands. BLAST for amino acid sequences can use the BLASTP program with default parameters, e.g., a word length (W) of 3, an expectation (E) of 10, and the BLOSUM62 scoring matrix (see Henikoff and Henikoff, *Proc Natl Acad Sci. USA* 89:10915, 1989). Exemplary determination of sequence alignment and % sequence identity can also employ the BESTFIT or GAP programs in the GCG Wisconsin Software package (Accelrys, Madison Wis.), using default parameters provided.

As used herein, "recombinant" or "engineered" or "non-naturally occurring" refers to a cell, nucleic acid, protein or vector that has been modified due to the introduction of an exogenous nucleic acid or the alteration of a native nucleic acid. Thus, e.g., recombinant cells express genes that are not found within the native (non-recombinant) form of the cell or express native genes differently than those genes are expressed by a non-recombinant cell. A "recombinant nucleic acid" is a nucleic acid made, in general, by the manipulation of nucleic acid, e.g., using polymerases and endonucleases, or otherwise into a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

As used herein, "recombinant variant" refers to any polypeptide differing from naturally occurring polypeptides by amino acid insertions, deletions, and substitutions, created using recombinant DNA techniques. Guidance in determining which amino acid residues may be replaced, added, or deleted without abolishing activities of interest, such as enzymatic or binding activities, may be found by comparing the sequence of the particular polypeptide with that of homologous peptides and minimizing the number of amino acid sequence changes made in regions of high homology. Amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

As used herein, "reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes to the primary sequence.

As used herein, "reporter" or "reporter molecule" refers to a moiety capable of being detected indirectly or directly. Reporters include, without limitation, a chromophore, a fluorophore, a fluorescent protein, a receptor, a hapten, an enzyme, and a radioisotope.

As used herein, "reporter gene" refers to a polynucleotide that encodes a reporter molecule that can be detected, either directly or indirectly. Exemplary reporter genes encode, among others, enzymes, fluorescent proteins, bioluminescent proteins, receptors, antigenic epitopes, and transporters.

As used herein, "reporter probe" refers to a molecule that contains a detectable label and is used to detect the presence (e.g., expression) of a reporter molecule. The detectable label on the reporter probe can be any detectable moiety, including, without limitation, an isotope (e.g., detectable by PET, SPECT, etc), chromophore, and fluorophore. The reporter probe can be any detectable molecule or composition that binds to or is acted upon by the reporter to permit detection of the reporter molecule.

As used herein, a "ribosome binding site" refers to a sequence of nucleotides upstream of the start codon of an mRNA transcript that is responsible for the recruitment of a ribosome during the initiation of protein translation.

As used herein, a "selection marker" refers to a gene introduced into a host cell that confers upon the host cell a trait suitable for artificial selection.

As used herein, "stringent hybridization conditions" refers to hybridizing in 50% formamide at 5×SSC at a temperature of 42° C. and washing the filters in 0.2×SSC at 60° C. (1×SSC is 0.15M NaCl, 0.015M sodium citrate.) Stringent hybridization conditions also encompasses low ionic strength and high temperature for washing, for example 0.015 M sodium chloride/0.0015 M sodium citrate/0.1% sodium dodecyl sulfate at 50° C.; hybridization with a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

As used herein, "substantial identity" refers to a polynucleotide or polypeptide sequence that has at least 80 percent sequence identity, at least 85 percent identity and 89 to 95 percent sequence identity. Substantial identity also encompasses at least 99 percent sequence identity as compared to a reference sequence over a comparison window of at least 20 residue positions or a window of at least 30-50 residues, wherein the percentage of sequence identity is calculated by comparing the reference sequence to a sequence that includes deletions or additions or substitutions over the window of comparison. In specific embodiments applied to polypeptides, the term "substantial identity" means that two polypeptide sequences, when optimally aligned, such as by the programs GAP or BESTFIT using standard parameters, i.e., default parameters, share at least 80 percent sequence identity, preferably at least 89 percent sequence identity, at least 95 percent sequence identity or more (e.g., 99 percent sequence identity).

Enzymes

Plant-derived cannabinoid neurotransmitters are biosynthesized in plants of *Cannabis sativa* L. (*Cannabis*, hemp, marijuana), *Cannabis ruderalis, Cannabis indica* primarily in glandular trichomes that cover female flowers at high density. Cannabinoids are formed in plants by a four-step process: alcanoyl-CoA formation, polyketide formation, aromatic prenylation and cyclization.

Enzymes capable of carrying out the synthesis steps for making the neurotransmitters described herein include *Cannabis sativa* hexanoyl-CoA synthetase/butyryl-CoA synthetase, 3,5,7-trioxododecanoyl-CoA synthase/3,5,7-trioxodecanoyl-CoA synthase, 3,5,7-trioxododecanoyl-CoA CoA-lyase, geranyl-diphosphate:olivetolate geranyltransferase, cannabichromenic acid synthase, cannabidiolic-acid synthase, and/or Δ1-tetrahydrocannabinolic acid synthase.

When amino acid sequences of the enzymes above are blasted against the NCBI database, multiple homologous genes (and cDNAs) can be identified in *Cannabis sativa* and *Cannabis indica* cultivars reflecting the multiple gene family organization of cannabinoid biosynthetic genes and that gene families gone through several duplication events creating multiple copies of homologues gene family members. Examples of homologous variant genes are described in Van Bakel et al (2011) Genome Biology 2011, 12:R102, in Sawler et al (2015) PLosOne 10(8): e0133292. doi:10.1371/journal.pone.0133292, and in the U.S. Pat. Application No 2014/0057251 A1, which are incorporated by reference in its entirety for all purposes.

Hexanoyl-CoA Synthetase from *Cannabis sativa* has the amino acid sequence of SEQ ID NO: 1. Other enzymes can make hexanoyl-CoA and/or butyryl-CoA including, for example, Acetate-CoA ligase (AMP-forming) (EC 6.2.1.1), Acetate-CoA ligase (ADP-forming) (EC 6.2.1.13), Butyrate-CoA ligase (AMP-forming) (EC 6.2.1.2), long chain acyl-CoA synthetases (EC 6.2.1.3), Succinate-CoA ligase (ADP-forming) (EC 6.2.1.5), Carboxylic acid-CoA ligase (GDP-forming) (EC 6.2.1.10), Biotin-CoA ligase (AMP-forming) (EC 6.2.1.11), 4-Coumarate-CoA ligase (AMP-forming) (EC 6.2.1.12), 6-carboxyhexanoate-CoA ligase (AMP-forming) (EC 6.2.1.14), 6-Arachidonate-CoA ligase (AMP-forming) (EC 6.2.1.15), Acetoacetate-CoA ligase (AMP-forming) (EC 6.2.1.16), Propanoate-CoA ligase (AMP-forming)

(EC 6.2.1.17), Omega-dicarboxylate-CoA ligase (AMP-forming) (EC 6.2.1.23), Phenylacetate:CoA ligase (AMP-forming) (EC 6.2.1.30), Hydroxypropanoate:CoA ligase (AMP-forming) (EC 6.2.1.36), 4-hydroxybutanoate:CoA ligase (AMP-forming) (EC 6.2.1.40), 3-(methylthio)propanoate:CoA ligase (AMP-forming) (EC 6.2.1.44), and/or Medium-chain-fatty-acid:[acyl-carrier protein] ligase (AMP-forming) (EC 6.2.1.47).

3,5,7-trioxododecanoyl-CoA synthase (EC 2.3.1.206) from *Cannabis sativa* has amino acid sequence of SEQ ID NO: 2. Other enzymes can make 3,5,7-trioxododecanoyl-CoA and/or 3,5,7-trioxodecanoyl-CoA including, for example, chalcone synthase (CHS), stilbene synthase (STS), malonyl-CoA:4-coumaroyl-CoA malonyltransferase (cyclizing) (EC:2.3.1.74), bisdemethoxycurcumin synthase (EC: 2.3.1.211), pinosylvin synthase (EC:2.3.1.146), phenylpropanoylacetyl-CoA synthase (EC:2.3.1.218), curcumin synthase (EC:2.3.1.217) curcumin/demethoxycurcumin synthase (EC:2.3.1.219), 3,5-dihydroxybiphenyl/4-hydroxycoumarin synthase (EC:2.3.1.177 2.3.1.208), 5,7-dihydroxy-2-methylchromone synthase (EC:2.3.1.216), 2,4,6-trihydroxybenzophenone synthase (EC:2.3.1.220), fungal type III polyketide synthase, phlD, phloroglucinol synthase (EC:2.3.1.253), 1,3,6,8-tetrahydroxynaphthalene synthase (EC:2.3.1.233), germicidin synthase, alpha-pyrone synthase, alkylresorcinol synthase, alkylpyrone synthase; and alkylresorcinol/alkylpyrone synthases.

3,5,7-trioxododecanoyl-CoA CoA-lyase (2,4-dihydroxy-6-pentylbenzoate-forming) (EC 4.4.1.26), from *Cannabis sativa* has the amino acid sequence of SEQ ID NO: 3. Other enzymes can make olivetolic acid or divarinic acid including, for example, tetracenomycin F2 cyclase (EC 4.2.1.154) from *Streptomyces glaucescens*, ActVA-Orf6 monooxygenase from *Streptomyces coelicolor*, MLMI, 4-methylmuconolactone methylisomerase from *Pseudomonas reinekei* MT1, AtHS1, At5g22580, and At1g51360 (AtDABB1) from *Arabidopsis thaliana*, and SP1 from *Populus tremolo*.

Geranyl-diphosphate:olivetolate geranyltransferase (EC 2.5.1.102) from *Cannabis sativa* has the amino acid sequence of SEQ ID NO: 4. Other enzymes can make CBGA or CBGVA include, for example, CloQ, involved in biosynthesis of clorobiocin from *Streptomyces roseochromogenes*, NovQ involved in biosynthesis of novobiocin from *Streptomyces spheroides*, NphB involved in biosynthesis of naphterpin from *Streptomyces* sp. strain CL 190, SCO7190 from *Streptomyces coelicolor*, Fnq26 and Fnq28 involved in biosynthesis of furanonaphthoquinone I from *Streptomyces cinnamomensis*, a prenyl transferase from *Hypericum calycinum* involved in biosynthesis of hyperxanthone E, PcPT involved in generation of bioactive furanocoumarin molecules from *Petroselinum crispum*, CIPT involved in coumarin biosynthesis from *Citrus limon*, CPT2 involved in biosynthetic route to lycosantalonol from *Solanum lycopersicum*, TkCPT1, TkCPT2, TkCPT3 involved in the biosynthesis of natural rubber from *Taraxacum koksaghyz*.

Cannabichromenic acid synthase from *Cannabis sativa* has the amino acid sequence of SEQ ID NO: 5. Cannabidiolic-acid synthase (EC 1.21.3.8) from *Cannabis sativa* has the amino acid sequence of SEQ ID NO: 6. Δ1-tetrahydrocannabinolic acid synthase (EC 1.21.3.7) from *Cannabis sativa* has the amino acid sequence of SEQ ID NO: 7.

Other enzymes can make CBCA/CBCVA, CBDA/CBDVA, and/or THCA/THCVA include, for example, PCBC, isopenicillin-N synthase (EC 1.21.3.1), columbamine oxidase (EC 1.21.3.2) and BBE1, reticuline oxidase (EC 1.21.3.3) involved in isoquinoline alkaloid, sulochrin oxidase [(+)-bisdechlorogeodin-forming] (EC 1.21.3.4) and sulochrin oxidase [(−)-bisdechlorogeodin-forming] (EC 1.21.3.5) from *Penicillium frequentans* and *Oospora sulphurea-ochracea*, AS1, aureusidin synthase (EC:1.21.3.6) involved in aurone biosynthetic pathway in plants.

Neurotransmitters

In some embodiments, the neurotransmitters are cannabinoids such as, for example, cannabigerolic acid (CBGA), cannabichromenic acid (CBCA), cannabidiolic acid (CBDA), tetrahydrocannabinolic acid (THCA), cannabigerovarinic acid (CBGVA), cannabidivarinic acid (CBDVA), cannabichromevarinic acid (CBCVA), or tetrahydrocannabivarinic acid (THCVA). When hexanoic acid (or other six carbon precursor) is used as precursor the microalgae can make CBGA, CBCA, CBDA and THCA. When butyric acid (or other four carbon precursor) is used as precursor the microalgae can make CBGVA, CBDVA, CBCVA, and THCVA.

To date, more than 104 different phytocannabinoids have been identified in *Cannabis* sp. plants (ElSohly, M. A. and W. Gul. 2014. Handbook of *Cannabis* (Chapter 2). Oxford, UK: Oxford University Press: P.20). Among these, delta-9-tetrahydrocannabinol (THC) has received the most attention because of its psychoactive properties, owing to its ability to act as a partial agonist of CB1 receptors. Phytocannabinoids exist mainly in the plant as their carboxylic precursors (delta-9-THCA) and are decarboxylated by light or heat while in storage or when combusted. THC shares a common precursor, olivetolic acid, with another quantitatively important plant constituent, cannabidiol (CBD), which is synthesized in vivo as a pre-cursor cannabidiolic acid (CBDA), and is converted to CBD by decarboxylation.

Nucleic Acids

Nucleic acids encode one or more of the enzymes described above. These nucleic acids are used to engineer into suitable host cells the biochemical pathways for making neurotransmitters that can interact with cannabinoid receptors in a subject.

In some embodiments, the nucleic acids are expression constructs, such as plasmids, or viral vectors, or linear vectors, or vectors that integrate into chromosomal DNA. Expression constructs can contain a nucleic acid sequence that enables the construct to replicate in one or more selected host cells (e.g., an origin of replication). Such sequences are well known for a variety of cells. E.g., the origin of replication from the plasmid pBR322 is suitable for most Gram-negative bacteria. In eukaryotic host cells, e.g., mammalian cells, the expression construct can be integrated into the host cell chromosome and then the construct replicates with the host chromosome. Similarly, constructs can be integrated into the chromosome of prokaryotic cells.

In general, expression constructs containing replication and control sequences that are derived from species compatible with the host cell are used in connection with a suitable host cell. The expression construct ordinarily carries a replication site, as well as marking sequences that are capable of providing phenotypic selection of the construct in transformed cells. For example, *E. coli* is typically transformed using pBR322, a plasmid derived from an *E. coli* species (see, e.g., Bolivar et al., (1977) Gene, 2: 95). pBR322 contains genes for ampicillin and tetracycline resistance and thus provides easy means for identifying transformed cells.

In some embodiments, the constructs used can be stimulated to increase (or decrease) copy number in a suitable host cell. This copy control can be used to change the window of detection/selection for the biosensors that are cloned in the constructs, e.g., fosmid clones. For example, the CopyControl Cloning System vectors which are sold by Epicentre can be used in the invention to make fosmid clones whose copy number can be inducibly changed (using arabinose). These copy number controllable constructs may be used in conjunction with the EPI300 *E. coli* strain which is also sold by Epicentre. In some embodiments, the CopyControl Cloning System is used to induce a high copy number for fosmid clones in the Metagenomic library.

Expression constructs also generally contain a selection gene, also termed a selectable marker. Selectable markers are well-known in the art for prokaryotic and eukaryotic cells, including host cells of the invention. Generally, the selection gene encodes a protein necessary for the survival or growth of transformed host cells grown in a selective culture medium. Host cells not transformed with the construct containing the selection gene will not survive in the culture medium. Typical selection genes encode proteins that (a) confer resistance to antibiotics or other toxins, e.g., ampicillin, neomycin, methotrexate, spectinomycin, chloramphenicol, kanamycin, or tetracycline, (b) complement auxotrophic deficiencies, e.g., the gene encoding D-alanine racemase for Bacilli unable to make D-alanine because of a mutant D-alanine racemase. In some embodiments, an exemplary selection scheme utilizes a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art.

The expression construct for producing the polypeptides of the invention contain a suitable control region that is recognized by the host organism and is operably linked to the nucleic acid encoding the polypeptide of interest. Promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences can interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, changes in nutrient concentration, or the presence of light.

Expression constructs of the invention typically have promoter elements, e.g., enhancers, to regulate the frequency of transcriptional initiation. Typically, these are located in the region 30-110 base pairs upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 base pairs apart before activity begins to decline. Depending on the promoter, it appears that individual elements can function either cooperatively or independently to activate transcription.

Promoters suitable for use in microalgae include, for example, β-tubulin from *Chlamydomonas reinhardtii*, viral promoters from cauliflower mosaic virus (CMV) and *chlorella* virus, which are active in multiple species of microalgae (see for example Plant Cell Rep. 2005 March; 23(10-11):727-35; J Microbiol. 2005 August; 43(4):361-5; Mar Biotechnol (NY). 2002 January; 4(1):63-73). Another promoter that is suitable for use in Prototheca is the *Chlorella sorokiniana* glutamate dehydrogenase promoter/5'UTR, the promoter for the *Chlorella* HUP1 gene, and the promoter for the *Chlorella ellipsoidea* nitrate reductase. The foregoing promoters and more promoters useful for expressing polypeptides in microalgae are disclosed in U.S. Pat. Nos. 8,222,010, 9,279,136 and 9,290,749, such as amino acid (AAT), ammonium (AMT), sugar (SUT) transporters (SEQ ID NOs: 55-66 of U.S. Pat. No. 9,279,136), and which are incorporated by reference in their entirety for all purposes. *Chlorella* virus promoters can also be used to express genes in Prototheca, such as SEQ ID NOs: 1-7 of U.S. Pat. No. 6,395,965, which is incorporated by reference in its entirety for all purposes. Still other promoters active in Prototheca can be found, for example, in Biochem Biophys Res Commun. 1994 Oct. 14; 204(1):187-94; Plant Mol. Biol. 1994 October; 26(1):85-93; Virology. 2004 Aug. 15; 326(1):150-9; and Virology. 2004 Jan. 5; 318(1):214-23, all of which are incorporated by reference in their entirety for all purposes.

Exemplary mammalian promoters include CMV immediate early, HSV thymidine kinase, early and late SV40, LTRs from retrovirus, and mouse metallothionein I. The nucleotide sequences of these and many other promoters have been published, thereby enabling a skilled worker to operably join them to DNA encoding the polypeptide of interest (Siebenlist et al, (1980) Cell, 20: 269) using linkers, adaptors or "scarless", to supply any required restriction sites. See also, e.g., Sambrook et al., Molecular Cloning: A Laboratory Manual, Cold Spring Harbor Laboratory Press, Cold Spring Harbor, N.Y. (1989); and Current Protocols in Molecular Biology, Ausubel et al., eds, Green Publishers Inc. and Wiley and Sons, N.Y (1994), both of which are incorporated by reference in their entirety for all purposes.

Nucleic acids that encode polypeptides are also described herein. The nucleic acid encoding a polypeptide can be easily prepared from an amino acid sequence of the polypeptide of interest using the genetic code. The nucleic acid encoding a polypeptide can be prepared using a standard molecular biological and/or chemical procedure. For example, based on the base sequence, a nucleic acid can be synthesized, and the nucleic acid of the present invention can be prepared by combining DNA fragments which are obtained from a cell or other nucleic acid using a polymerase chain reaction (PCR).

For recombinant expression of a polypeptide in a host cell, it can be beneficial to employ coding sequences in recombinant nucleic acids that produce mRNA with codons preferentially used by the host cell. Thus, proper expression of transgenes can require that the codon usage of the transgene matches the specific codon bias of the organism in which the transgene is being expressed. Codon optimization for microalgae is described in U.S. Pat. Nos. 8,222,010 and 9,290,749, both of which are incorporated by reference in their entirety for all purposes. Table 1 shows codon usage for mRNAs from Prototheca strains.

TABLE 1

Preferred codon usage in Prototheca strains

| Ala | GCG | 345 (0.36) | Asn | AAT | 8 (0.04) | Val | GTG | 308 (0.5) |
|---|---|---|---|---|---|---|---|---|
|  | GCA | 66 (0.07) |  | AAC | 201 (0.96) |  | GTA | 9 (0.01) |
|  | GCT | 101 (0.11) |  |  |  |  | GTT | 35 (0.06) |
|  | GCC | 442 (0.46) | Pro | CCG | 161 (0.29) |  | GTC | 262 (0.43) |
|  |  |  |  | CCA | 49 (0.09) |  |  |  |
| Cys | TGT | 12 (0.1) |  | CCT | 71 (0.13) | Trp | TGG | 107 (1) |
|  | TGC | 105 (0.9) |  | CCC | 267 (0.49) |  |  |  |
|  |  |  |  |  |  | Tyr | TAT | 10 (0.05) |
| Asp | GAT | 43 (0.12) | Gln | CAG | 226 (0.82) |  | TAC | 180 (0.95) |
|  | GAC | 316 (0.88) |  | CAA | 48 (0.18) |  |  |  |
|  |  |  |  |  |  | Lys | AAG | 284 (0.98) |
| Glu | GAG | 377 (0.96) | Arg | AGG | 33 (0.06) |  | AAA | 7 (0.02) |
|  | GAA | 14 (0.04) |  | AGA | 14 (0.02) |  |  |  |
|  |  |  |  | CGG | 102 (0.18) | Leu | TTG | 26 (0.04) |
| Phe | TTT | 89 (0.29) |  | CGA | 49 (0.08) |  | TTA | 3 (0) |
|  | TTC | 216 (0.71) |  | CGT | 51 (0.09) |  | CTG | 447 (0.61) |
|  |  |  |  | CGC | 331 (0.57) |  | CTA | 20 (0.03) |
| Gly | GGG | 92 (0.12) |  |  |  |  | CTT | 45 (0.06) |
|  | GGA | 56 (0.07) | Ser | AGT | 16 (0.03) |  | CTC | 190 (0.26) |
|  | GGT | 76 (0.1) |  | AGC | 123 (0.22) |  |  |  |
|  | GGC | 559 (0.71) |  | TCG | 152 (0.28) | Met | ATG | 191 (1) |
|  |  |  |  | TCA | 31 (0.06) |  |  |  |
| His | CAT | 42 (0.21) |  | TCT | 55 (0.1) | Stop | TGA |  |
|  | CAC | 154 (0.79) |  | TCC | 173 (0.31) |  | TAG |  |
| Ile | ATA | 4 (0.01) | Thr | ACG | 184 (0.38) |  | TAA |  |
|  | ATT | 30 (0.08) |  | ACA | 24 (0.05) |  |  |  |
|  | ATC | 338 (0.91) |  | ACT | 22 (0.05) |  |  |  |
|  |  |  |  | ACC | 249 (0.52) |  |  |  |

The nucleic acids may also encode fragments and/or variants of a polypeptide having one or more deletions, additions and substitutions to the sequence. The fragments and/or variants can have 1, 2, 3 or more deletions, additions and/or substitutions to the sequence. The additions and deletions can be in the internal sequence, carboxy, and/or amino terminus of the polypeptide sequence, where the variant retains the desired enzymatic activity. The term "conservative variation" denotes the replacement of an amino acid residue by another biologically similar residue, or the replacement of a nucleotide in a nucleic acid sequence such that the encoded amino acid residue does not change or is changed to another structurally, chemically or otherwise functionally similar residue. In this regard, some substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, and tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Polypeptides having substantially the same amino acid sequence as the reference molecule but possessing minor amino acid substitutions that do not substantially affect the activity of the polypeptide are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

Homologs of the enzymes used herein are also disclosed. As used herein, the term "homologs" includes analogs and paralogs. The term "anologs" refers to two polynucleotides or polypeptides that have the same or similar function, but that have evolved separately in unrelated host organisms. The term "paralogs" refers to two polynucleotides or polypeptides that are related by duplication within a genome. Paralogs usually have different functions, but these functions may be related. Analogs and paralogs of an enzyme can differ from the wild-type enzyme by post-translational modifications, by amino acid sequence differences, or by both. In particular, homologs will generally exhibit at least 80-85%, 85-90%, 90-95%, or 95%, 96%, 97%, 98%, or 99% sequence identity, with all or part of the wild-type enzyme sequence, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Any and all such nucleic acid variations and resulting amino acid polymorphisms or variations that are the result of natural allelic variation and that do not alter the functional activity of the gene of interest, are intended to be within the scope of the disclosure.

As used herein, "derivative" or "variant" refers to a enzymes, or a nucleic acid encoding an enzyme, that has one or more conservative amino acid variations or other minor modifications such that the corresponding polypeptide has substantially equivalent function when compared to the wild type polypeptide. These variants or derivatives include polypeptides having minor modifications of the enzyme primary amino acid sequences that may result in peptides which have substantially equivalent activity as compared to the unmodified counterpart enzyme. Such modifications may be deliberate, as by site-directed mutagenesis, or may be spontaneous. The term "variant" further contemplates deletions, additions and substitutions to the sequence, so long as the enzyme functions. The term "variant" also includes the modification of a polypeptide where the native signal peptide is replaced with a heterologous signal peptide to facilitate the expression or secretion of the polypeptide from a host species.

The nucleic acid of the present invention can be linked to another nucleic acid so as to be expressed under control of a suitable promoter. The nucleic acid of the present invention can be also linked to, in order to attain efficient transcription of the nucleic acid, other regulatory elements that cooperate with a promoter or a transcription initiation site, for example, a nucleic acid comprising an enhancer sequence, or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

When the nucleic acid of the present invention is introduced into a host cell, the nucleic acid of the present invention may be combined with a substance that promotes transference of a nucleic acid into a cell, for example, a reagent for introducing a nucleic acid such as a liposome or a cationic lipid, in addition to the aforementioned excipients. Alternatively, a construct carrying the nucleic acid of the present invention is also useful.

Host Cells

In the present invention, various host cells can be used with the polynucleotides and polypeptides of the invention. The host cell may be any of the host cells familiar to those skilled in the art, including prokaryotic cells and eukaryotic cells, such as bacterial cells, fungal cells, yeast cells, mammalian cells, insect cells, or plant cells.

In other embodiments, the host cells are algal and/or photosynthetic, or non-photosynthetic, including but not limited to algae or photosynthetic cells of the genera *Agmenellum, Amphora, Anabaena, Ankistrodesmus, Asterochloris, Asteromonas, Astephomene, Auxenochlorella, Basichlamys, Botryococcus, Botryokoryne, Boekelovia, Borodinella, Brachiomonas, Catena, Carteria, Chaetoceros, Chaetophora, Characiochloris, Characiosiphon, Chlainomonas, Chlamydomonas, Chlorella, Chlorochytrium, Chlorococcum, Chlorogonium, Chloromonas, Chrysosphaera, Closteriopsis, Cricosphaera, Cryptomonas, Cyclotella, Dictyochloropsis, Dunaliella, Ellipsoidon, Eremosphaera, Eudorina, Euglena, Fragilaria, Floydiella, Friedmania, Haematococcus, Hafniomonas, Heterochlorella, Gleocapsa, Gloeothamnion, Gonium, Halosarcinochlamys, Hymenomonas, Isochrysis, Koliella, Lepocinclis, Lobocharacium, Lobochlamys, Lobomonas, Lobosphaera, Lobosphaeropsis, Marvania, Monoraphidium, Myrmecia, Nannochloris, Nannochloropsis, Navicula, Nephrochloris, Nitschia, Nitzschia, Ochromonas, Oocystis, Oogamochlamys, Oscillatoria, Pabia, Pandorina, Parietochloris, Pascheria, Phacotus, Phagus, Phormidium, Platydorina, Platymonas, Pleodorina, Pleurochrysis, Polulichloris, Polytoma, Polytomella, Prasiola, Prasiolopsis, Prasiococcus, Prototheca, Pseudochlorella, Pseudocarteria, Pseudotrebouxia, Pteromonas, Pyrobotrys, Rosenvingiella, Scenedesmus, Schizotrichium, Spirogyra, Stephanosphaera, Tetrabaena, Tetraedron, Tetraselmis, Thraustochytrium, Trebouxia, Trochisciopsis, Ulkenia, Viridiella, Vitreochlamys, Volvox, Volvulina, Vulcanochloris, Watanabea,* or *Yamagishiella.* In some embodiments, the host cell is *Botryococcus braunii, Prototheca krugani, Prototheca moriformis, Prototheca portoricensis, Prototheca stagnora, Prototheca wickerhamii, Prototheca zopfii, Schizotrichium* sp, and the like.

Microalgae are eukaryotic microbial organisms that contain a chloroplast or plastid, and optionally are capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include cells such as *Chlorella, Dunaliella,* and *Prototheca*. Microalgae also include other microbial photosynthetic organisms that exhibit cell-cell adhesion, such as *Agmenellum, Anabaena,* and Pyrobotrys. Microalgae also include obligate heterotrophic microorganisms that have lost the ability to perform photosynthesis, such as certain dinoflagellate algae species, thraustochytrids such as Schizotrichium and species of the genus *Prototheca*. Examples of microalgae are provided in PCT Patent Applications WO2008/151149, WO2010/06032, WO2011/150410, and WO2011/150411, all of which are incorporated by reference in their entirety for all purposes.

In some embodiments, host cells are *Prototheca* strains, particularly recombinant *Prototheca* strains, for the production of lipids. Species of *Prototheca* for use in the invention can be identified by amplification of certain target regions of the genome. Well established methods of phylogenetic analysis, such as amplification and sequencing of ribosomal internal transcribed spacer (ITS1 and ITS2 rDNA), 23S rRNA, 18S rRNA, and other conserved genomic regions can be used by those skilled in the art to identify species of not only *Prototheca*, but other hydrocarbon and lipid producing organisms with similar lipid production capability. For examples of methods of identification and classification of algae also see for example Genetics, 2005 August; 170(4): 1601-10 and RNA, 2005 April; 11(4):361-4. Microalgae for use in the present invention typically have genomic DNA sequences encoding for 16S rRNA that have at least 99%, at least 95%, at least 90%, at least 85%, at least 80%, at least 75%, or at least 70% sequence identity described in Ewing A, et al (2014) J. Phycol. 50: 765-769, which is incorporated by reference in its entirety for all purposes.

In some embodiments, the eukaryotic cells are fungi cells, including, but not limited to, fungi of the genera *Aciculoconidium, Ambrosiozyma, Arthroascus, Arxiozyma, Ashbya, Aspergillus, Babjevia, Bensingtonia, Botryoascus, Botryozyma, Brettanomyces, Bullera, Bulleromyces, Candida, Chlamydomonas, Chrysosporium, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Fusarium, Galactomyces, Geotrichum, Guilliermondella, Hanseniaspora, Hansenula, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Neotyphodium, Neurospora, Ogataea, Oosporidium, Pachysolen, Penicillium, Phachytichospora, Phaffia, Pichia, Rhodosporidium, Rhodotorula, Saccharomyces, Saccharomycodes,*

*Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichoderma, Trichosporiella, Trichosporon, Trigonopsis, Tsuchiyaea, Udeniomyces, Waltomyces, Wickerhamia, Wickerhamiella, Williopsis, Xanthophyllomyces, Yamadazyma, Yarrowia, Zygoascus, Zygosaccharomyces, Zygowilliopsis,* and *Zygozyma,* among others. In some embodiments, the fungi is *Candida albicans, Chrysosporium lucknowense, Fusarium graminearum, Fusarium venenatum, Hansenula polymorpha, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccharomyces cerevisiae, Schizosaccharomyces pompe, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Trichoderma reesei* and *Xanthophyllomyces dendrorhous* (formerly *Phaffia rhodozyma*), or a filamentous fungi, e.g. *Trichoderma, Aspergillus* sp., including *Aspergillus nidulans, Aspergillus niger, Aspergillus oryzae, Aspergillus phoenicis, Aspergillus carbonarius,* and the like.

In some embodiments the host cells are plant cells. In some embodiments the plant cells are cells of monocotyledonous or dicotyledonous plants, including, but not limited to, alfalfa, almonds, asparagus, avocado, banana, barley, bean, blackberry, brassicas, broccoli, cabbage, canola, carrot, cauliflower, celery, cherry, chicory, citrus, coffee, cotton, cucumber, eucalyptus, hemp, lettuce, lentil, maize, mango, melon, oat, papaya, pea, peanut, pineapple, plum, potato (including sweet potatoes), pumpkin, radish, rapeseed, raspberry, rice, rye, sorghum, soybean, spinach, strawberry, sugar beet, sugarcane, sunflower, tobacco, tomato, turnip, wheat, zucchini, and other fruiting vegetables (e.g. tomatoes, pepper, chili, eggplant, cucumber, squash etc.), other bulb vegetables (e.g., garlic, onion, leek etc.), other pome fruit (e.g. apples, pears etc.), other stone fruit (e.g., peach, nectarine, apricot, pears, plums etc.), *Arabidopsis*, woody plants such as coniferous and deciduous trees, an ornamental plant, a perennial grass, a forage crop, flowers, other vegetables, other fruits, other agricultural crops, herbs, grass, or perennial plant parts (e.g., bulbs; tubers; roots; crowns; stems; stolons; tillers; shoots; cuttings, including un-rooted cuttings, rooted cuttings, and callus cuttings or callus-generated plantlets; apical meristems etc.). The term "plants" refers to all physical parts of a plant, including seeds, seedlings, saplings, roots, tubers, stems, stalks, foliage and fruits.

Suitable prokaryote host cells include bacteria, e.g., eubacteria, such as Gram-negative or Gram-positive organisms, for example, any species of *Acidovorax, Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Streptomyces, Synechococcus, Vibrio,* and *Zymomonas,* including, e.g., *Bacillus amyloliquefaciens, Bacillus subtilis, Brevibacterium ammoniagenes, Brevibacterium immariophilum, Clostridium acetobutylicum, Clostridium beigerinckii, Clostridium Beijerinckii, Clostridium saccharoperbutylacetonicum, Clostridium saccharobutylicum, Clostridium aurantibutyricum, Clostridium tetanomorphum, Enterobacter sakazakii, Bacillus cereus, Escherichia coli, Lactococcus lactis, Mesorhizobium loti, Pseudomonas aeruginosa, Pseudomonas fluorescens, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Serratia marcescens, Shigella dysenteriae, Shigella flexneri, Shigella sonnei, Staphylococcus aureus, Vibrio natriegens,* and the like.

One example of an *E. coli* host is *E. coli* 294 (ATCC 31,446). Other strains such as EPI300 *E. coli, E. coli* B, *E. coli* X1776 (ATCC 31,537), and *E. coli* W3110 (ATCC 27,325) are also suitable. These examples are illustrative rather than limiting. Strain W3110 is a typical host because it is a common host strain for recombinant DNA product fermentations. In one aspect of the invention, the host cell should secrete minimal amounts of proteolytic enzymes. For example, strain W3110 may be modified to affect a genetic mutation in the genes encoding proteins, with examples of such hosts including *E. coli* W3110 strains 1A2, 27A7, 27B4, and 27C7 described in U.S. Pat. No. 5,410,026 issued Apr. 25, 1995, which is incorporated by reference in its entirety for all purposes.

Exemplary insect cells include any species of *Spodoptera* or *Drosophila*, including *Drosophila* S2 and *Spodoptera* Sf9. Exemplary animal cells include CHO, COS or Bowes melanoma or any appropriate mouse or human cell line known to person of skill in the art.

Introduction of Polynucleotides to Host Cells

In some embodiments, the nucleic acid(s) of the invention is/are introduced to the eukaryotic cell by transfection (e.g., Gorman, et al. Proc. Natl. Acad. Sci. 79.22 (1982): 6777-6781, which is incorporated by reference in its entirety for all purposes), transduction (e.g., Cepko and Pear (2001) Current Protocols in Molecular Biology unit 9.9; DOI: 10.1002/0471142727.mb0909s36, which is incorporated by reference in its entirety for all purposes), calcium phosphate transformation (e.g., Kingston, Chen and Okayama (2001) Current Protocols in Molecular Biology Appendix 1C; DOI: 10.1002/0471142301.nsa01cs01, which is incorporated by reference in its entirety for all purposes), calcium chloride and polyethylene glycol (PEG) to introduce recombinant DNA into microalgal cells (see Kim et al., (2002) Mar. Biotechnol. 4:63-73, which reports the use of this method to transform *Chlorella ellipsoidea* protoplasts, and which is incorporated by reference in its entirety for all purposes), cell-penetrating peptides (e.g., Copolovici, Langel, Eriste, and Langel (2014) ACS Nano 2014 8 (3), 1972-1994; DOI: 10.1021/nn4057269, which is incorporated by reference in its entirety for all purposes), electroporation (e.g Potter (2001) Current Protocols in Molecular Biology unit 10.15; DOI: 10.1002/0471142735.im1015s03 and Kim et al (2014) Genome 1012-19. doi:10.1101/gr.171322.113, Kim et al. 2014 describe the Amaza Nucleofector, an optimized electroporation system, both of these references are incorporated by reference in their entirety for all purposes), microinjection(e.g., McNeil (2001) Current Protocols in Cell Biology unit 20.1; DOI: 10.1002/0471143030.cb2001sl8, which is incorporated by reference in its entirety for all purposes), liposome or cell fusion (e.g., Hawley-Nelson and Ciccarone (2001) Current Protocols in Neuroscience Appendix 1F; DOI: 10.1002/0471142301.nsa01fs10, which is incorporated by reference in its entirety for all purposes), mechanical manipulation (e.g. Sharon et al. (2013) PNAS 2013 110(6); DOI: 10.1073/pnas.1218705110, which is incorporated by reference in its entirety for all purposes), biolistic methods (see, for example, Sanford, Trends in Biotech. (1988) 6: 299 302, U.S. Pat. No. 4,945,050, which is incorporated by reference in its entirety for all purposes), Lithium Acetate/PEG transformation (Gietz and Woods (2006) Methods Mol. Biol. 313, 107-120) and its modifications, which is incorporated by reference in its entirety for all purposes, or other well-known techniques for delivery of nucleic acids to host cells. Once introduced, the nucleic acids of the invention can be expressed episomally, or can be integrated into the genome of the host cell using well known techniques such as recombination (e.g., Lisby and Rothstein (2015) Cold Spring Harb Perspect Biol. Mar 2; 7(3). pii: a016535. doi: 10.1101/cshperspect.a016535, which is incorporated by reference in its entirety for all purposes), non-homologous integration (e.g., Deyle and Russell (2009) Curr Opin Mol Ther. 2009 August; 11(4):442-7, which is incorporated by reference in its entirety for all purposes) or transposition (as described above for mobile genetic elements). The efficiency of homologous and non-homologous recombination can be facilitated by genome editing technologies that introduce targeted single or double-stranded breaks (DSB). Examples of DSB-generating technologies are CRISPR/Cas9, TALEN, Zinc-Finger Nuclease, or equivalent systems (e.g., Cong et al. Science 339.6121 (2013): 819-823, Li et al. *Nucl. Acids Res* (2011): gkr188, Gaj et al. Trends in Biotechnology 31.7 (2013): 397-405, all of which are incorporated by reference in their entirety for all purposes), transposons such as Sleeping Beauty (e.g., Singh et al (2014) Immunol Rev. 2014 January; 257(1):181-90. doi: 10.1111/imr.12137, which is incorporated by reference in its entirety for all purposes), targeted recombination using, for example, FLP recombinase (e.g., O'Gorman, Fox and Wahl Science (1991) 15:251(4999):1351-1355, which is incorporated by reference in its entirety for all purposes), CRE-LOX (e.g., Sauer and Henderson PNAS (1988): 85; 5166-5170), or equivalent systems, or other techniques known in the art for integrating the nucleic acids of the invention into the eukaryotic cell genome.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

Techniques for transforming a wide variety of higher plant species are well known and described in the technical and scientific literature. See, e.g., Weising (1988) Ann. Rev. Genet. 22:421-477; U.S. Pat. No. 5,750,870, which are both incorporated by reference in their entirety for all purposes.

Methods of Making Neurotransmitters

Microalgae can be engineered with the above described enzymes so as to create biosynthetic pathways in the microalgae that can produce neurotransmitters. Micro algae can be engineered with nucleic acids encoding polypeptides of SEQ ID NO: 1, SEQ ID NO: 2, SEQ ID NO: 3, SEQ ID NO: 4, SEQ ID NO: 5, SEQ ID NO: 6, SEQ ID NO: 7, and/or nucleic acids encoding enzymes related to any of hexanoyl-CoA synthetase/butyryl-CoA synthetase, 3,5,7-trioxododecanoyl-CoA synthase/3,5,7-trioxodecanoyl-CoA synthase, 3,5,7-trioxododecanoyl-CoA CoA-lyase, geranyl-diphosphate:olivetolate geranyltransferase, cannabichromenic acid synthase, cannabidiolic-acid synthase, and/or Δ1-tetrahydrocannabinolic acid synthase as described above. Nucleic acids encoding the foregoing enzyme(s) are engineered into appropriate constructs, and these constructs are placed into microalgae using appropriate methods described above.

In some embodiments, microalgae engineered as described above are grown under suitable conditions and in the presence of hexanoic acid to make CBGA and from CBGA to make CBCA, CBDA and/or THCA. In an alternative embodiment, the microalgae utilize butanoic acid to make CBGVA and from CBGVA to make CBCVA, CBDVA, and THCVA.

In some embodiments, *Prototheca* is engineered with nucleic acids that have *Prototheca* control regions (promoters) described above operably linked to nucleic acids that are codon optimized for *Prototheca* and encode SEQ ID NO: 1-7, 1-5, 1-4 and 6, or 1-4 and 7. These engineered *Prototheca* are grown under suitable nutrient conditions and fed hexanoic acid to make CBGA and from CBGA to make CBCA, CBDA and/or THCA. In an alternative embodiment, the engineered *Prototheca* are fed butanoic acid to make CBGVA and from CBGVA to make CBCVA, CBDVA, and THCVA.

In an aspect, cannabinoids are extracted, and/or purified. Acidic cannabinoids can be extracted and/or purified. Neutral cannabinoids also can be extracted and/or purified. Another aspect includes heating and/or storing acidic cannabinoids to produce neutral cannabinoids.

Growth of Microalgae

The microalgae can be grown at any scale suitable for a particular purpose. For example, for large scale production of neurotransmitters, cultures can be grown on a large scale (e.g., 10,000 L, 40,000 L, 100,000 L or larger bioreactors) in a bioreactor. Microalgae (e.g., *Prototheca*) and other host cells (e.g., fungi, mammalian cells, or prokaryotic cells) are typically cultured in liquid media. The bioreactor or fermenter is used to culture microalgae cells through the various phases of their physiological cycle. Microalgae can be fermented in large quantities in liquid, such as in suspension cultures as an example. Bioreactors such as steel fermenters can accommodate very large culture volumes (40,000 liter and greater capacity bioreactors can be used). Bioreactors also typically allow for the control of culture conditions such as temperature, pH, oxygen tension, and carbon dioxide levels. For example, bioreactors are typically configurable, for example, using ports attached to tubing, to allow gaseous components, like oxygen or nitrogen, to be bubbled through a liquid culture. Other culture parameters, such as the pH of the culture media, the identity and concentration of trace elements, and other media constituents can also be more readily manipulated using a bioreactor.

Bioreactors can be configured to flow culture media though the bioreactor throughout the time period during which the microalgae grow and increase in number. In some embodiments, for example, media can be infused into the bioreactor after inoculation but before the cells reach a desired density. In other instances, a bioreactor is filled with culture media at the beginning of a culture, and no more culture media is infused after the culture is inoculated. In other words, the microalgae biomass is cultured in an aqueous medium for a period of time during which the microalgae reproduce and increase in number; however, quantities of aqueous culture medium are not flowed through the bioreactor throughout the time period. Thus in some embodiments, aqueous culture medium is not flowed through the bioreactor after inoculation.

Bioreactors equipped with devices such as spinning blades and impellers, rocking mechanisms, stir bars, means for pressurized gas infusion can be used to subject microalgae cultures to mixing. Mixing may be continuous or intermittent. For example, in some embodiments, a turbulent flow regime of gas entry and media entry is not maintained for reproduction of microalgae until a desired increase in number of said microalgae has been achieved.

Microalgae culture media typically contains components such as a fixed nitrogen source, a fixed carbon source, trace elements, optionally a buffer for pH maintenance, and phosphate (typically provided as a phosphate salt). Other components can include salts such as sodium chloride, particularly for seawater microalgae. Nitrogen sources include organic and inorganic nitrogen sources, including, for example, without limitation, molecular nitrogen, nitrate, nitrate salts, ammonia (pure or in salt form, such as, $(NH_4)2SO_4$ and $NH_4OH$), protein, soybean meal, cornsteep liquor, and yeast extract. Examples of trace elements include zinc, boron, cobalt, copper, manganese, and molybdenum in, for example, the respective forms of $ZnCl_2$, $H_3BO_3$, $CoCl_6H_2O$, $CuCl_2.2H_2O$, $MnCl_2.4H_2O$ and $(NH4)6Mo_7O_{24}.4H_2O$.

Oils and Related Products, Lipid Production and Extraction

The host cells described herein include one or more exogenous genes encoding cannabinoid biosynthesis enzymes. Some host cells, e.g., microalgae, produce natural oils containing the cannabinoids that are not obtainable from a non-plant oil, or not obtainable at all.

The microalgae host cells can produce a storage oil, which can include hydrocarbons such as triacylglyceride that may be stored in storage bodies of the host cell as well as related products that can include, without limitation, phospholipids, tocopherols, tocotrienols, carotenoids (e.g., alpha-carotene, beta-carotene, lycopene, etc.), xanthophylls (e.g., lutein, zeaxanthin, alpha-cryptoxanthin and beta-crytoxanthin), cannabinoids, isoprenoids and various organic or inorganic compounds. A raw oil may be obtained from the cells by disrupting the cells and isolating the oil. See WO2008/151149, WO2010/06032, WO2011/150410, and WO2011/1504 which disclose heterotrophic cultivation and oil isolation techniques, and all of which are incorporated by reference in their entirety for all purposes. For example, oil may be obtained by cultivating, drying and pressing the cells. The oils produced may also be refined, bleached and deodorized (RBD) to remove phospholipids, free fatty acids and odors as known in the art or as described in WO2010/120939, which is incorporated by reference in its entirety for all purposes. The raw or RBD oils may be used in a variety of food, chemical, pharmaceutical, nutraceutical and industrial products or processes. After recovery of the oil, a valuable residual biomass remains. Uses for the residual biomass can include the production of paper, plastics, absorbents, adsorbents, as animal feed, for human nutrition, or for fertilizer.

The stable carbon isotope value δ13C is an expression of the ratio of 13C/12C relative to a standard (e.g. PDB, carbonite of fossil skeleton of Belemnite americana from Peedee formation of South Carolina). The stable carbon isotope value δ13C (0/00) of the oils can be related to the δ13C value of the feedstock used. The oils can be derived from oleaginous organisms heterotrophically grown on sugar derived from a C4 plant such as corn or sugarcane. The δ13C (0/00) of the oil can be from −10 to −17 0/00 or from −13 to −16 0/00.

The oils disclosed herein can be made by methods using a microalgal host cell. As described above, the microalga can be, without limitation, Chlorophyta, Trebouxiophyceae, Chlorellales, Chlorellaceae, or Chlorophyceae. It has been found that oils from microalgae of Trebouxiophyceae can be distinguished from vegetable oils based on their sterol profiles. Oil produced by *Chlorella protothecoides* can include sterols such as brassicasterol, ergosterol, campesterol, stigmasterol, and β-sitosterol. Sterols produced by *Chlorella* can have C24β stereochemistry. Microalgae oils can also include, for example, campesterol, stigmasterol, β-sitosterol, 22,23-dihydrobrassicasterol, proferasterol and clionasterol. Oils produced by the microalgae may be distinguished from plant oils by the presence of sterols with C24β stereochemistry and the absence of C24αstereochemistry in the sterols present. For example, the oils produced may contain 22,23-dihydrobrassicasterol while lacking campesterol; contain clionasterol, while lacking in β-sitosterol, and/or contain poriferasterol while lacking stigmasterol. Alternately, or in addition, the oils may contain significant amounts of Δ7-poriferasterol.

Oleaginous host cells expressing genes SEQ ID NO:1-7 can produce an oil with at least 1% of cannabinoid. The oleaginous host cell (e.g., microalgae) can produce an oil, cannabinoid, triglyceride, isoprenoid or derivative of any of these. These host cells can be made by transforming a cell with any of the nucleic acids discussed herein. The transformed cell can be cultivated to produce an oil and, optionally, the oil can be extracted. Oil extracted can be used to produce food, oleochemicals, nutraceuticals, pharmaceuticals or other products.

The oils discussed above alone or in combination can be useful in the production of foods, pharmaceuticals, nutraceuticals, and chemicals. The oils, cannabinoids, isoprenoids, triglycerides can be subjected to decarboxilation, oxidation, light exposure, hydroamino methylation, methoxy-carbonation, ozonolysis, enzymatic transformations, epoxidation, methylation, dimerization, thiolation, metathesis, hydro-alkylation, lactonization, or other chemical processes. After extracting the oil, a residual biomass may be left, which may have use as a fuel, as an animal feed, or as an ingredient in paper, plastic, or other product.

The various cannabinoid oils can be tailored in for a mixture of specific cannabioids or their derivatives in order to adjust parameters such as biological and therapeutical efficacy, therapeutic index, potency, safety, bioavailability, permeability, as well as polarity and solvency of the oils or chemicals made from the oils. For the production of cannabinoids total lipids produced by cells can be harvested, or otherwise collected, by any convenient means. Lipids can be isolated by whole cell extraction. The cells can be first disrupted, and then intracellular and cell membrane/cell wall-associated lipids as well as extracellular hydrocarbons can be separated from the cell mass, such as by use of centrifugation. Intracellular lipids produced in microorganisms can be extracted after lysing the cells of the microorganism. Extracellular lipids can be isolated by separation from cell biomass, drying or directly extracted. Once extracted, lipids can be refined to produce oils, pharmaceuticals, nutraceuticals, or oleochemicals.

After completion of culturing, the host cells can be separated from the fermentation broth. Optionally, the separation is effected by centrifugation to generate a concentrated paste. The biomass can then optionally be washed with a washing solution (e.g., deionized water) to get rid of the fermentation broth and debris. Optionally, the washed microbial biomass may also be dried (oven dried, lyophilized, etc.) prior to cell disruption. Alternatively, cells can be lysed without separation from some or all of the fermentation broth when the fermentation is complete. For example, the cells can be at a ratio of less than 1:1 v:v cells to extracellular liquid when the cells are lysed.

Host cells containing a lipid can be lysed to produce a lysate. The step of lysing a host cell (also referred to as cell lysis) can be achieved by any convenient means, including heat-induced lysis, adding a base, adding an acid, using enzymes such as proteases and polysaccharide degradation enzymes such as amylases, using ultrasound, mechanical lysis, using osmotic shock, infection with a lytic virus, and/or expression of one or more lytic genes. Lysis is performed to release intracellular molecules which have been produced by the host cell. Each of these methods for lysing a host cell can be used as a single method or in combination simultaneously or sequentially. The extent of host cell disruption can be observed by microscopic analysis. Typically more than 70% cell breakage is observed. Cell breakage can be more than 80%, more than 90%, or about 100%.

The host cells can be lysed after growth, for example to increase the exposure of cellular lipid and/or cannabionid for extraction or further processing. The timing of lipase expression (e.g., via an inducible promoter) or cell lysis can be adjusted to optimize the yield of lipids and/or cannabinoids. Below are described a number of lysis techniques. These techniques can be used individually or in combination.

The step of lysing a host cell can comprises heating of a cellular suspension containing the host cell. The fermentation broth containing the host cell (or a suspension of host cells isolated from the fermentation broth) is heated until the host cells, i.e., the cell walls and membranes of host cells degrade or breakdown. Typically, temperatures applied are at least 50° C. Other temperatures, such as, at least 30° C. at least 60° C., at least 70° C., at least 80° C., at least 90° C., at least 100° C., at least 110° C., at least 120° C., at least 130° C. or higher can be used for more efficient cell lysis. Lysing cells by heat treatment can be performed by boiling the host cell. Alternatively, heat treatment (without boiling) can be performed in an autoclave. The heat treated lysate may be cooled for further treatment. Cell disruption can also be performed by steam treatment, i.e., through addition of pressurized steam. Steam treatment of microalgae for cell disruption is described, for example, in U.S. Pat. No. 6,750, 048, which is incorporated by reference in its entirety for all purposes. Steam treatment may be achieved by sparging steam into the fermentor and maintaining the broth at a desired temperature for less than about 90 minutes, less than about 60 minutes, or less than about 30 minutes.

The step of lysing a host cell can also be done by adding a base to a cellular suspension containing the host cell. The base should be strong enough to hydrolyze at least a portion of the proteinaceous compounds of the host cell. Bases which are useful for solubilizing proteins are known in the art of chemistry. Exemplary bases include, but are not limited to, hydroxides, carbonates and bicarbonates of lithium, sodium, potassium, calcium, and mixtures thereof. One base that can be used is KOH. Base treatment of microalgae for cell disruption is described, for example, in U.S. Pat. No. 6,750,048, which is incorporated by reference for all purposes.

The step of lysing a host cell can include adding an acid to a cellular suspension containing the host cell. Acid lysis can be effected using an acid at a concentration of 10-500 mN or preferably 40-160 nM. Acid lysis can be performed at above room temperature (e.g., at 40-160°, and preferably a temperature of 30-180°. For moderate temperatures (e.g., room temperature to 100° C. and particularly room temperature to 65°, acid treatment can usefully be combined with sonication or other cell disruption methods.

The step of lysing a host cell can also involve lysing the host cell by using an enzyme. Enzymes for lysing a microorganism can be proteases and polysaccharide-degrading enzymes such as hemicellulase (e.g., hemicellulase from *Aspergillus niger*; Sigma Aldrich, St. Louis, Mo.; #H2125), pectinase (e.g., pectinase from *Rhizopus* sp.; Sigma Aldrich, St. Louis, Mo.; #P2401), Mannaway 4.0 L (Novozymes), cellulase (e.g., cellulose from *Trichoderma viride*; Sigma Aldrich, St. Louis, Mo.; #C9422), and driselase (e.g., driselase from Basidiomycetes sp.; Sigma Aldrich, St. Louis, Mo.; #D9515).

Lysis can also be accomplished using an enzyme such as, for example, a cellulase such as a polysaccharide-degrading enzyme, optionally from *Chlorella* or a *Chlorella* virus, or a protease, such as *Streptomyces griseus* protease, chymotrypsin, proteinase K, proteases listed in Degradation of Polylactide by Commercial Proteases, Oda Y et al., Journal of Polymers and the Environment, Volume 8, Number 1, January 2000, pp. 29-32(4), Alcalase 2.4 FG (Novozymes), and Flavourzyme 100 L (Novozymes). Any combination of a protease and a polysaccharide-degrading enzyme can also be used, including any combination of the preceding proteases and polysaccharide-degrading enzymes.

The step of lysing a host can be performed using ultrasound, i.e., sonication. Thus, host cells can also by lysed with high frequency sound. The sound can be produced electronically and transported through a metallic tip to an appropriately concentrated cellular suspension. This sonication (or ultrasonication) disrupts cellular integrity based on the creation of cavities in cell suspension.

Lysis can be performed using an expeller press. In this process, biomass is forced through a screw-type device at high pressure, lysing the cells and causing the intracellular lipid to be released and separated from the protein and fiber (and other components) in the cell.

The step of lysing a host cell can be performed by mechanical lysis. Cells can be lysed mechanically and optionally homogenized to facilitate hydrocarbon (e.g., lipid) collection. For example, a pressure disrupter can be used to pump a cell containing slurry through a restricted orifice valve. High pressure (up to 1500 bar) can be applied, followed by an instant expansion through an exiting nozzle. Cell disruption can be accomplished by three different mechanisms: impingement on the valve, high liquid shear in the orifice, and sudden pressure drop upon discharge, causing an explosion of the cell. The method releases intracellular molecules. Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. Cells can also be disrupted by shear forces, such as with the use of blending (such as with a high speed or Waring blender as examples), the french press, or even centrifugation in case of weak cell walls, to disrupt cells.

The step of lysing a host cell can also be performed by applying an osmotic shock.

The step of lysing a host cell can be accomplished with an infection of the host cell with a lytic virus. A wide variety of viruses are known to lyse host cells, and the selection and use of a particular lytic virus for a particular host cell is known. For example, paramecium bursaria *Chlorella* virus (PBCV-1) is the prototype of a group (family Phycodnaviridae, genus *Chlorovirus*) of large, icosahedral, plaque-forming, double-stranded DNA viruses that replicate in, and lyse, certain unicellular, eukaryotic *Chlorella*-like green algae. Accordingly, any susceptible microalgae can be lysed by infecting the culture with a suitable *Chlorella* virus. Methods of infecting species of *Chlorella* with a *Chlorella* virus are known. See for example Adv. Virus Res. 2006; 66:293-336; Virology, 1999 Apr. 25; 257(1):15-23; Virology, 2004 Jan. 5; 318(1):214-23; Nucleic Acids Symp. Ser. 2000; (44):161-2; J. Virol. 2006 March; 80(5):2437-44; and Annu. Rev. Microbiol. 1999; 53:447-94, all of which are incorporated by reference in their entirety for all purposes.

The step of lysing a host cell can use autolysis. Host cells can be genetically engineered to produce a lytic protein at a desired time so that the host cell lyses after expression of the lytic protein. The lytic gene can be expressed using an inducible promoter so that the cells can first be grown to a desirable density in a fermentor, followed by induction of the promoter to express the lytic gene to lyse the cells. The lytic gene can encode a polysaccharide-degrading enzyme, or a lytic gene from a lytic virus. For example, a lytic gene from a *Chlorella* virus can be expressed in an algal cell; see Virology 260, 308-315 (1999); FEMS Microbiology Letters 180 (1999) 45-53; Virology 263, 376-387 (1999); and Virology 230, 361-368 (1997), all of which are incorporated by reference in their entirety for all purposes. Expression of lytic genes can be done using an inducible promoter, such as a promoter active in microalgae that is induced by a stimulus such as the presence of a small molecule, light, heat, and other stimuli.

Various methods are available for separating lipids from cellular lysates produced by the above methods. For example, lipids and lipid derivatives such as cannabinoids, cannabinoid acids, aldehydes, alcohols, and hydrocarbons such as isoprenoids can be extracted with a hydrophobic solvent such as hexane (see Frenz et al. 1989, Enzyme Microb. Technol., 11:717, which is incorporated by reference in its entirety for all purposes), heptane or butane. Lipids and lipid derivatives can also be extracted using liquefaction (see for example Sawayama et al. 1999, Biomass and Bioenergy 17:33-39 and Inoue et al. 1993, Biomass Bioenergy 6(4):269-274, which are each incorporated by reference in their entirety for all purposes); oil liquefaction (see for example Minowa et al. 1995, Fuel 74(12):1735-1738, which is incorporated by reference in its entirety for all purposes); and supercritical CO2 extraction (see for example Mendes et al. 2003, Inorganica Chimica Acta 356:328-334, which is incorporated by reference in its entirety for all purposes). Miao and Wu describe a protocol of the recovery of microalgal lipid from a culture of *Chlorella prototheocoides* in which the cells were harvested by centrifugation, washed with distilled water and dried by freeze drying. The resulting cell powder was pulverized in a mortar and then extracted with n-hexane (Miao and Wu, Biosource Technology (2006) 97:841-846, which is incorporated by reference in its entirety for all purposes).

Lipids, lipid derivatives and hydrocarbons generated by the host cells can be recovered by extraction with an organic solvent. The organic solvent can be hexane or heptane. The organic solvent can be added directly to the lysate without prior separation of the lysate components or to the whole cell broth. The lysate generated by one or more of the methods described above can be contacted with an organic solvent for a period of time sufficient to allow the lipid and/or hydrocarbon components to form a solution with the organic solvent. The solution can then be further refined to recover specific desired lipid or hydrocarbon components. Hexane or heptane extraction methods can be used.

Lipids and lipid derivatives, cannabinoid acids, alcohols, and hydrocarbons such as isoprenoids can be produced by host cells after modification of the host cells by the use of one or more enzymes, including a cannabinoid synthase. When cannabioids are in the extracellular environment of the cells, the one or more enzymes can be added to that environment under conditions in which the enzyme modifies the cannabinoid or completes its synthesis from a cannabinoid precursor. Alternatively, cannabinoids can be partially, or completely, isolated from the cellular material before addition of one or more catalysts such as enzymes. Such catalysts are exogenously added, and their activity occurs outside the cell or in vitro.

Cannabinoids, hydrocarbons and other lipid produced by cells in vivo, or enzymatically modified in vitro, as described herein can be optionally further processed by conventional means. The processing can include "cracking" to reduce the size of the molecules through decarboxylation, and thus increase the hydrogen:carbon ratio, of hydrocarbon molecules. Catalytic and thermal cracking methods are routinely used in cannabinoid, hydrocarbon and triglyceride oil processing. Catalytic methods may involve the use of a catalyst, such as a solid acid catalyst, cofactor, solvent, oxygen or light, which could lead to the heterolytic, or asymmetric, breakage of a carbon-carbon bond and/or result in oxidation. Hydrocarbons can also be processed to reduce, optionally to zero, the number of carbon-carbon double, or triple, bonds therein. Hydrocarbons can also be processed to remove or eliminate or add a ring or cyclic structure therein. Hydrocarbons can also be processed to increase the hydrogen:carbon ratio. This can include the addition of hydrogen ("hydrogenation") and/or the "cracking" of hydrocarbons into smaller hydrocarbons.

Thermal methods involve the use of elevated temperature and pressure to reduce hydrocarbon size via decarboxylation. An elevated temperature of about 15-180° C. and pressure of about 4,000-70,000 kPa can be used. Thermal methods are standard in cannabinoid processing and oil refining. Cannabinoid hydrocarbons produced by host cells can be collected and processed or refined via conventional means. Decarboxylation converts THCA into a number of cannabinoid compounds, most notably Δ9-THC, cannabinolic acid CBNA and cannabinol CBN; decarboxylation of CBDA most notably results in cannabidiol CBD, and of CBGA in cannabigerol CBG. The methods of decarboxylating cannabinoids are known, see US patent application US20150152018A1 and US20120046352A1, which are incorporated by reference for all purposes in their entirety. The fraction can be treated with another catalyst, such as an organic compound, heat, and/or an inorganic compound resulting in additional cannabinoids and their derivatives.

Uses of Neurotransmitters

The neurotransmitters made above can be used to treat inflammation (anti-inflammatory and anto-oxidant), nausea (anti-emetic), and/or pain (analgesia, antinociceptive). The neurotransmitters can also be used as a sedative. Cannabinoids and their derivatives can be used, for example, to treat chronic pain, nausea and vomiting due to chemotherapy, spasticity due to multiple sclerosis or paraplegia, depression, anxiety disorder, addiction, sleep disorder, psychosis, glaucoma, stimulate appetite in HIV/AIDS, obesity, diabetes, inflammation, body temperature, certain cancers, epilepsy and seizures, movement disorders (e.g. Huntington's disease and amyotrophic lateral sclerosis), Alzheimer's, and/or Tourette syndrome.

Cannabinoids can act at the 5-HT1A (hydroxytryptamine) serotonin receptor, implicated in a range of biological and neurological processes, including but not limited to anxiety, addiction, appetite, sleep, pain reception, nausea and vomiting; the vanilloid receptors such as TRPV1, which also functions as ion channel, and is known to mediate pain perception, inflammation, and body temperature; the orphan receptors, such as G protein-coupled receptors GPR55, which plays a role in cancer, GPR119, implicated in obesity and diabetes, and GPR18, implicated in anti-inflammatory effects; the peroxisome proliferator activated receptors (PPARs), involved in various metabolic functions with PPAR-gamma implicated in anti-cancer effects and degradation of amyold-beta plaque, which is linked to the development of Alzheimer's disease.

Cannabinoids can compete with endogenous cannabinoids for fatty acid binding proteins (FABP), which escort various lipid molecules intracellularly and across cell membranes, resulting in inhibition of reuptake and breakdown of endogenous cannabinoids in synapses, or adenosine, which in turn results in increased activity of A1A and A2A adenosine receptors.

Cannabinoids can also function as allosteric receptor modulators, either enhancing or inhibiting signal transmission by changing the shape of the receptor. Examples include positive allosteric modulation of the GABA-A receptor, and negative allosteric modulation of the cannabinoid CB1 receptor.

The neurotransmitters, cannabinoids or a pharmaceutically acceptable salt thereof, may be formulated for administration in a variety of ways. In some embodiments, the neurotransmitters, cannabinoids or a pharmaceutically acceptable salt thereof can be formulated with a biologically acceptable medium, such as water, buffered saline, polyol (for example, glycerol, propylene glycol, liquid polyethylene glycol and the like), triglyceride oil or suitable mixtures thereof. The neurotransmitters, cannabinoids or a pharmaceutically acceptable salt thereof, may be formulated as solid pharmaceutical preparations in a usual dosage form, typically, in the dosage form of powders, granules, surface-coated granules, capsules, tablets or surface-coated tablets. In some embodiments, a granulation step is used in which a humectant can be added as a stabilizer and optionally, an auxiliary agent for manufacturing a pharmaceutical preparation are added to bulk powders and the resulting mixture is granulated by means of a granulator, the encapsulation step in which the resulting granular powders are encapsulated under compression by means of a capsule filler or the tableting step in which the resulting granular powders are compressed by means of a tablet machine and, if desired, the coating step in which the granular powders, tablets or granules obtained in the preceding steps are surface-coated.

As used herein, "biologically acceptable medium" includes any and all solvents, dispersion media, and the like which may be appropriate for the desired route of administration of the pharmaceutical preparation. Suitable vehicles and their formulation are described, for example, in the book Remington's Pharmaceutical Sciences (Remington's Pharmaceutical Sciences. Mack Publishing Company, Easton, Pa., USA 1985), which is incorporated by reference in its entirety for all purposes.

The inventions disclosed herein will be better understood from the experimental details which follow. However, one skilled in the art will readily appreciate that the specific methods and results discussed are merely illustrative of the inventions as described more fully in the claims which follow thereafter. Unless otherwise indicated, the disclosure is not limited to specific procedures, materials, or the like, as such may vary. It is also to be understood that the terminology used herein is for the purpose of describing particular embodiments only and is not intended to be limiting.

EXAMPLES

Example 1. Biosynthesis of Olivetolic and Divarinic Acids

The three *Cannabis sativa* genes (SEQ ID NO: 1-3) of Example 1 were synthesized in a codon-optimized form to reflect *Prototheca moriformis* codon usage. A transforming construct and the sequences of the genes are provided in SEQ ID NO: 8 [pUR17001]. Transgenic strains were generated via transformation of the base strain P006 (*Prototheca moriformis* UTEX 1435) with a construct encoding all three genes. Construct pUR17001 can be written as DAO1_5'::CrBTUBp-NPTII-PmPGH:PmACP1p-CsHCS1-PmHSP90:PmSAD2p-CsOAS-CvNR:PmAMT3p-CsTKS-PmPGH::DAO1_3'. The 5' and 3' ends of the construct represent genomic DNA from *Prototheca moriformis* that target integration of the construct to the D-aspartate oxidase (DAO1) locus via homologous recombination. Proceeding in the 5' to 3' direction, the selection cassette has the *Chlamydomonas reinhardtii* β-tubulin promoter driving expression of the *Escherichia coli* neomycin phosphotransferse gene NPTII (conferring the resistance to antibiotic G418) and the *Prototheca moriformis* 2-phospho-D-glycerate hydroylase (PGH) gene 3' UTR. The second expression cassette containing the codon optimized hexanoyl-CoA synthetase/butyryl-CoA synthetase gene from *Cannabis sativa* (CsHCS, SEQ ID NO: 1) is driven by the *Prototheca moriformis* acyl carrier protein (ACP1) promoter and has the *Prototheca moriformis* heat shock protein (HSP90) gene 3' UTR. The third expression cassette containing the codon optimized 3,5,7-trioxododecanoyl-CoA CoA-lyase (olivetolic acid synthase) gene from *Cannabis sativa* (CsOAS, SEQ ID NO: 3) is driven by the *P. moriformis* stearoyl-ACP desaturase (SAD2) promoter and has the *Chlorella vulgaris* nitrate reductase (NR) gene 3' UTR. The final expression cassette containing the codon optimized 3,5,7-trioxododecanoyl-CoA synthase/3,5,7-trioxodecanoyl-CoA synthase (tetraketide synthase) gene from *Cannabis sativa* (CsTKS, SEQ ID NO: 2) is driven by the *P. moriformis* ammonium transporter (AMT3) promoter and has the *Prototheca moriformis* 2-phospho-D-glycerate hydroylase (PGH) gene 3' UTR. The pUR0001 construct encoding all three heterologous *Cannabis sativa* genes was transformed into a *Prototheca* strain and transformed cells were selected for the ability to grow in the presence of antibiotic G418. Transformations, cell culture, and gene expression analysis were all carried out as in WO2013/158938. Multiple transformations were performed. Positive transformation clones are identified at each step using Southern blot assays and/or RT-PCR to identify clones that are expressing mRNA encoding SEQ ID NO: 1-3.

Positive clones obtained after the expression constructs for SEQ ID NO: 1-3 are incorporated into *Prototheca moriformis* and are grown under nitrogen-replete conditions in the presence of hexanoic (hexanoate) and/or butyric (butanoate) acids and analyzed for olivetolic or divarinic acid production, respectively. The biomass is extracted via solvent extraction or using an expeller press and is analyzed for lipid profile. Olivetolic and/or divarinic acid production are determined using standard GC/FID analysis.

Example 2. Method for Making CBGA, CBCA, CBDA, THCA, CBGVA, CBCVA, CBDVA, and THCVA Cannabinoids The four cannabinoid genes of Example 2 were synthesized in a codon-optimized form to reflect *Prototheca moriformis* codon usage. A representative construct to synthesize CBGA and the sequence of the *Cannabis sativa* geranyldiphosphate:olivetolate geranyltransferase (prenyl transferase, "CsPT1", SEQ ID NO: 4) is provided in SEQ ID NO: 9 [pUR17002]. The CBGA-synthesizing prenyl transferases were synthesized with either native (SEQ ID NO: 4), "CsPT1tp", or with modified transit peptides from *Chlorella protothecoides* (Cp) (SEQ ID NO: 11) or *Prototheca moriformis* (SEQ ID NO: 12, 13, and 14) in place of the native transit peptide. The modified transit peptides derived from the CpSAD1 gene, "CpSAD1tp", from PmSAD1 gene, "PmSAD1tp", from PmHDR gene, "PmHDRtp", from PmFAD2 gene, "PmFAD2tp", were synthesized as an in-frame, N-terminal fusions to the CBGA prenyl transferase in place of the native transit peptide. Transgenic strains were generated via transformation of the pUR17001-transformed *Prototheca moriformis* strain producing olivetolic and/or divarinic acid (Example 1) with a construct encoding CBGA prenyl transferase gene, such as pUR17002. Construct pUR17002 can be written as PDR1_5'::PmLDH1p-AtThiC-PmHSP90:PmSAD2p-CsPT1tp-CsPT1-PmHSP90:: PDR1_3'. The 5' and 3' ends of the construct represent genomic DNA from *Prototheca moriformis* that target integration of the construct to the PDR1 locus via homologous recombination. Proceeding in the 5' to 3' direction, the selection cassette has the *Prototheca moriformis* lactate dehydrogenase (LDH1) gene promoter driving expression of the *Arabidopsis thaliana* phosphomethylpyrimidine synthase (ThiC) gene (complementing thiamine auxotrophy) and the *Prototheca moriformis* heat shock protein (HSP90) gene 3' UTR. The second expression cassette containing the codon optimized prenyl transferase gene from *Cannabis sativa* (CsPT1, SEQ ID NO: 4) fused to the native *Cannabis sativa* CsPT1 plastid-targeting transit peptide, CsPT1tp, is driven by the *Prototheca moriformis* acyl carrier protein (ACP1) promoter and has the *Prototheca moriformis* heat shock protein (HSP90) gene 3' UTR.

To synthesize CBDA, THCA and CBCA, cannabinoids derived from CBGA, or CBDVA, THCVA, and CBCVA, cannabinoids derived from CBGVA, the correspondent cannabinoid synthase genes were coexpressed with CsPT1 prenyl transferase. A representative transforming construct and the sequence of the corresponding cannabinoid synthase is provided in SEQ ID NO: 10 [pUR17003], using CBDA synthase as an example. Identical methods were used to generate each of the remaining constructs encoding the different corresponding cannabinoid synthases, THCA and CBCA synthases. The CBDA, THCA and CBCA synthases were synthesized without native N-terminal secretion targeting signal peptides. Transgenic strains were generated via transformation of the pUR17001-transformed *Prototheca moriformis* strain producing olivetolic and/or divarinic acid (Example 1) with constructs encoding CBDA, THCA, CBCA synthase genes, such as in pUR17003. Construct pUR17003 can be written as PDR1-5'::PmLDH1p-AtThiC-PmHSP90:PmSAD2p-CsPT1tp-CsPT1-CvNR:PmAMT3p-CsCBDAS-PmHSP90::PDR1_3'. The 5' and 3' ends of the construct represent genomic DNA from *Prototheca moriformis* that target integration of the construct to the PDR1 locus via homologous recombination. Proceeding in the 5' to 3' direction, the selection cassette has the *Prototheca moriformis* lactate dehydrogenase (LDH1) gene promoter driving expression of the *Arabidopsis thaliana* phosphomethylpyrimidine synthase (ThiC) gene (complementing thiamine auxotrophy) and the *Prototheca moriformis* heat shock protein (HSP90) gene 3' UTR. The second expression cassette containing the codon optimized prenyl transferase gene from *Cannabis sativa* (CsPT1, SEQ ID NO: 4) fused to the native *Cannabis sativa* CsPT1 plastid-targeting transit peptide, CsPT1tp, is driven by the *Prototheca moriformis* acyl carrier protein (ACP1) promoter and has the *Chlorella vulgaris* nitrate reductase (NR) gene 3' UTR. The third expression cassette containing the codon optimized CBDA synthase gene from *Cannabis sativa* (CsCBDAS, SEQ ID NO: 6) without the native N-terminal secretion pathway targeting peptide, is driven by the *Prototheca moriformis* ammonium transporter (AMY3) promoter and has the *Prototheca moriformis* heat shock protein or in (HSP90) gene 3' UTR.

The pUR17002 and pUR17003 constructs encoding representative prenyl transferase and cannabinoid synthase genes were transformed into a native *Prototheca* strain or pUR17001-transformed *Prototheca moriformis* strain that synthesizes olivetolic and/or divarinic acid (Example 1) and transformed cells were selected for the ability to grow in the absence of thiamine. Transformations, cell culture, and gene expression analysis were all carried out as in WO2013/158938. Multiple transformations were performed.

Positive clones obtained after the expression constructs for SEQ ID NO: 1-7 are incorporated into *Prototheca moriformis* are grown under nitrogen-replete conditions in the presence of hexanoic (hexanoate) and/or butyric (butanoate) acids and analyzed for CBGA, CBDA, THCA and CBCA, and/or CBGVA, CBDVA, THCVA, and CBCVA production, respectively. The biomass was extracted via solvent extraction or using an expeller press and was analyzed for lipid profile. Cannabinoid production and composition is determined by standard GC/FID analysis.

Example 3. Fermentation of Microalgae in the Presence of Carboxylic Acid

This example describes culturing of *Prototheca moriformis* (UTEX 1435) strain R2 in the presence of hexanoic (hexanoate) acid to test the impact of carboxylic acid on cell growth. Cryopreserved R2 cells were thawed at room temperature and 50 ul of cells were added to 5 ml of medium A2 (4.2 g/L K2HPO4, 3.1 g/L NaH2PO4, 0.24 g/L MgSO4.7H2O, 0.25 g/L Citric Acid monohydrate, 0.025 g/L CaCl2 2H2O, 2 g/L yeast extract), 100 mM PIPES pH7.0, supplemented with 2% glucose, trace minerals described in U.S. Pat. No. 5,900,370, and 1× Vitamin Cocktail (1000× solution): 9 g tricine, 0.67 g thiamine HCL, 0.01 g biotin, 0.008 g cyannocobalamin (vitamin B12), 0.02 g calcium pantothenate, 0.04 g p-aminobenzoic acid, and grown heterotrophically for 24 hrs at 28° C. with agitation (200 rpm) in a 15 ml tube. The 500 ul R2 aliquots were transferred into 10 ml fresh media and grown in the presence of 0, 1, 3 and 10 uM sodium hexanoate for 4 days in 50 ml fermentation bioreactor tubes. Samples from the cultures were pulled at 24, 48, 72 and 96 hours and growth was measured using A750 readings on a spectrophotometer. Growth was observed for each of the concentrations tested as shown in FIG. 1 establishing the feasibility of supplementing the fermentation growth media with carboxylic acids.

Example 4. Cannabinoid Isolation by Solvent Extraction and Characterization by Analytical Analysis This example describes isolation of cannabinoids and total lipids from dried biomass using solvent extraction suitable for analytical analysis and downstream processing. Biomass from fermentation cultures was dried using lyophilization for 24 hours prior to cell disruption. Lipid samples were prepared from 10-40 mg of dried biomass by re-suspension in 100-200 ul of 100 mM Sodium citrate, pH 5.0 and extensive sonication. The mixture was then extracted with 450 ul of Acetone-heptane mix (1:9) and vigorous agitation. Samples were phase-separated by centrifugation at 20,000 g for 4 minutes and the portion of upper layer was transferred to a vial or another tube for subsequent use. For analytical analysis of cannabinoids, samples were processed by standard UHPLC-PDA/MS chromatography using Perkin Elmer Altus A-30 UPLC system with Brownlee SPP 2.7 mm C18 2.1×100 mm column. The reverse phase C18 column was developed with gradients 65-80% or 10-90% water-acetonitrile and 0.1% formic acid solvent system for detection and quantification of the biosynthetic intermediates and cannabinoids, respectively. Elution was monitored by photodiode array detection (PDA) over the range of 210-400 nm; MS scan was conducted in ES$^+$ mode for masses between 150 to 850 Da. Analytical standards were used to establish calibration curve used in quantification of cannabinoids.

Example 5. Engineering Biosynthesis and Fermentation of Olivetolic Acid in Microalgae The three *Cannabis sativa* genes, hexanoyl-CoA synthetase, 3,5,7-trioxododecnoyl-CoA synthase and 3,5,7-trioxododecanoyl-CoA CoA-lyse (SEQ ID NO: 1-3, respectively) were synthesized in a codon-optimized form to reflect *Prototheca moriformis* codon usage and used to make a construct pU092 (SEQ ID NO: 15). Construct pU092 can be written as DAO1_5'::PmLDH1p-CpSADtp_ThiC-PmPGH:PmAMT3p-CsOAS-PmHSP90:PmSAD2p-CsTKS-PmSAD2:PmACPp-CsHCS-PmPGH::DAO1_3'. The 5' and 3' ends of the construct represent genomic DNA from *Prototheca moriformis* that target integration of the construct to the D-aspartate oxidase (DAO1) locus via homologous recombination. Proceeding in the 5' to 3' direction, the selection cassette has the *Prototheca moriformis* lactate dehydrogenase (LDH) promoter driving expression of the *Arabidopsis thaliana* phosphomethylpyrimidine synthase (ThiC) gene (complementing thiamine auxotrophy) and the *Prototheca moriformis* 2-phospho-D-glycerate hydroylase (PGH) gene 3' UTR. The second expression cassette containing the codon optimized 3,5,7-trioxododecanoyl-CoA CoA-lyase (olivetolic acid synthase) gene from *Cannabis sativa* (CsOAS, SEQ ID NO: 3) is driven by the *P. moriformis* ammonium transporter (AMT3) promoter and has the *Prototheca moriformis* heat shock protein (HSP90) gene 3' UTR. The third expression cassette containing the codon optimized 3,5,7-trioxododecanoyl-CoA synthase/3,5,7-trioxododecanoyl-CoA synthase (tetraketide synthase) gene from *Cannabis sativa* (CsTKS, SEQ ID NO: 2) is driven by the *P. moriformis* stearoyl-ACP desaturase (SAD2) promoter and has the *Prototheca moriformis* stearoyl-ACP desaturase (SAD2) gene 3' UTR. The final expression cassette containing the codon optimized hexanoyl-CoA synthetase/butyryl-CoA synthetase gene from *Cannabis sativa* (CsHCS, SEQ ID NO: 1) is driven by the *Prototheca moriformis* acyl carrier protein (ACP1) promoter and has the *Prototheca moriformis* 2-phospho-D-glycerate hydroylase (PGH) gene 3' UTR.

Transgenic strains were generated via Lithium acetate/PEG transformation of the base strain R2 (*Prototheca moriformis* UTEX 1435) with a construct encoding all three genes. The pU092 construct encoding all three heterologous *Cannabis sativa* genes was transformed into a Prototheca R2 strain and primary transformants were selected on agar plates lacking thiamine. Transformations, cell culture, and gene expression analysis were all carried out as in WO2013/158938. Multiple transformations were performed. Positive transformation clones were verified by genomic PCR and/or RT-PCR to identify clones that are expressing mRNA encoding SEQ ID NO: 1-3.

Positive clones obtained after the expression construct pU092 for SEQ ID NO: 1-3 were incorporated into *Prototheca moriformis* R2 and were grown in A2 media as described in Example 3 for 48 hours. 120 ul of these cultures were transferred into 1.5 ml fresh A2 media modified to include 1.89 mM Ammonium sulfate, 4% glucose, 100 mM Pipes, pH 7.0, 1×Vitamin Cocktail lacking thiamine hydrochloride, and supplemented with 3 uM of sodium hexanoate. Fermentations were carried out for 5 days at 28° C. with agitation (200 rpm) in a 15 ml bioreactor tubes. Cells were fed with 3% glucose and 3 uM hexanoic acid after 72 hours. Total lipid samples were prepared from dried biomass from each transformant as described in Example 4 and products were analyzed using UHPLC-PDA/MS chromatography as described above.

As shown in FIG. 2, introduction of polynucleotide pU092 (SEQ ID NO: 15) into wild-type strain (FIG. 2A) results in production of olivetolic acid (m/z 225.16 Da) (FIG. 2B and FIG. 2C). The biosynthesis of olivetolic acid was confirmed by direct comparison of the new product with analytical standard based on identical HPLC elution time, UV spectra (λmax 220, 299, and 261), and the occurrence of the major ionized fragments (m/z 207.15 and 225.16 Da).

Example 6. Method for Making Acidic Cannabinoids: Engineering Biosynthesis and Fermentation in Microalgae This example describes engineering and biosynthesis of major *Cannabis sativa* phytocannabinoid molecules in *Prototheca moriformis* UTEX1435: the cannabidiolic acid (CBDA), and Δ9-tetrahydrocannabinolic acid (THCA), both derived from a shared precursor, cannabigerolic acid (CBGA), through distinct biosynthetic reactions. Initially, we constructed a microalgae strain S1 expressing Geranyldiphosphate:olivetolate geranyltransferase and Cannabidiolic acid synthase genes from *Cannabis sativa* (SEQ ID NO: 4 and 6, respectively) that encode enzymes converting olivetolic/divarinic acids stepwise into cannabigerolic/cannabigerovarinic (CBGA/CBGVA) and cannabidiolic/cannabidivarinic (CBDA/CBDVA) acids. A transforming construct and the sequences of the genes are provided in SEQ ID NO: 16 [pU061]. The cannabinoid genes were synthesized in a codon-optimized form to reflect *Prototheca moriformis* codon usage.

Construct pU061 can be written as Thi4_5'::PmHXT1-NeoR-CvNR:PmACP1p-CvCBDAS-PmHSP90:PmSAD2p-PmIPDStp-CsPT-SAD2::Thi4_3'. The 5' and 3' ends of the construct represent genomic DNA from *Prototh-* eca moriformis that target integration of the construct to the Thi4 (thiamine biosynthesis) locus via homologous recombination. Proceeding in the 5' to 3' direction, the selection cassette has the *Prototheca moriformis* hexose transporter (HXT1) promoter driving expression of the *Escherichia coli* neomycin phosphotransferse gene NPTII (conferring the resistance to antibiotic G418) and the *Prototheca moriformis* heat-shock protein (HSP90) gene 3' UTR. The second expression cassette containing the codon optimized CBDA synthase gene from *Cannabis sativa* (CsCBDAS, SEQ ID NO: 6) without the native N-terminal secretion pathway targeting peptide, is driven by the *Prototheca moriformis* acyl carrier protein (ACP1) promoter and has the *Prototheca moriformis* heat shock protein or in (HSP90) gene 3' UTR. The third expression cassette containing the codon optimized prenyl transferase gene from *Cannabis sativa* (CsPT1, SEQ ID NO: 4) fused to the *Prototheca moriformis* isopentenyl diphosphate synthase (IPDS) plastid-targeting transit peptide (SEQ ID NO: 13), is driven by the *Prototheca moriformis* Stearoyl ACP desaturase (SAD2) promoter and has the *Prototheca moriformis* Stearoyl ACP desaturase (SAD2) gene 3' UTR.

Alternative versions of polynucleotide pU061 included additional forms of geranyl-diphosphate:olivetolate geranyl-transferase (CsPT1) gene, synthesized with either native (SEQ ID NO: 4), CsPT1tp, or with modified plastid transit peptides from *Chlorella* protothecoides (Cp) (SEQ ID NO: 11) or *Prototheca moriformis* (SEQ ID NO: 12, and 14) in place of the native transit peptide. The modified transit peptides derived from the CpSAD1 gene, "CpSAD1tp", from PmSAD1 gene, "PmSAD1tp", from PmIPDS gene, "PmIPDStp", from PmFAD2 gene, "PmFAD2tp", were synthesized as an in-frame, N-terminal fusions to the CBGA/CBGVA prenyl transferase in place of the native transit peptide.

Transgenic strains were generated via transformation of *Prototheca moriformis* (UTEX1435) R2 strain with polynucleotide pU061 (SEQ ID NO: 16) using lithium acetate/PEG method and positive transformants were selected on solid agar plates in the presence of 100 μg/mL of antibiotic G418. Transformations, cell culture, and gene expression analysis were all carried out as in WO2013/158938 and as described above. Positive transformation clones were verified by genomic PCR and/or RT-PCR to identify clones that are expressing mRNA encoding SEQ ID NO: 4 and 6, and cryopreserved.

To generate microalgae strains capable of synthesizing CBDA, cryopreserved R2-pU061 strain S1 expressing high levels of CsPT1 and CsCBDAS genes (SEQ ID NO:16) was transformed with polynucleotide pU092 (SEQ ID NO: 15). Positive clones were identified as colonies growing on agar plates lacking thiamine in the presence of antibiotic G418. The organization and expression of five *Cannabis* genes was subsequently verified by genomic PCR and/or RT-PCR, and selected representative strains were cryopreserved.

Positive S1-pU092 clones obtained after the expression construct pU092 for SEQ ID NO: 1-3 is incorporated into *Prototheca moriformis* R2-pU61 strain S1 were grown in A2 media as described in Examples 3 and 5 for 48 hours. The 120 ul of these cultures were transferred into 1.5 ml fresh A2 media modified to include 1.89 mM Ammonium sulfate, 4% glucose, 100 mM Pipes, pH 7.0, 1×Vitamin Cocktail lacking thiamine hydrochloride, and supplemented with 3 uM of sodium hexanoate. Fermentations were carried out for 5 days at 28° C. with agitation (200 rpm) in a 15 ml bioreactor tubes. Cells were fed with 3% glucose and 3 uM hexanoic acid after 48 and 72 hours. Total lipid samples were prepared from dried biomass from each transformant as described in Example 4 and products were analyzed using UHPLC-PDA/MS chromatography as described above in Example 4.

Figure 3:
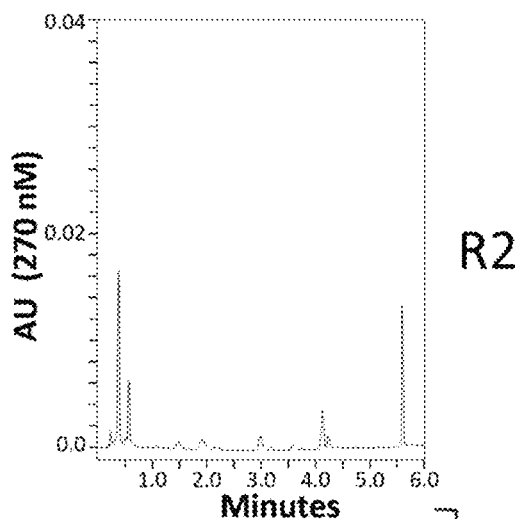
FIG. 3 illustrates biosynthesis of CBGA and CBDA in *Prototheca moriformis*. HPLC chromatograms (AU 270 nM) of representative wild-type (R2) (FIG. 3A) and a representative R2 transformed with pU061 (strain S1, SEQ ID NO: 16) and pU092 (SEQ ID NO: 15) (FIG. 3B) strains demonstrate accumulation of CBGA and CBDA in microalgae (R2-061-092). Elution of cannabigerolic and cannabidiolic acids at ca. 1.9 and 1.6 min, respectively, is confirmed by MS (FIG. 3C and FIG. 3D, respectively).
Figure 3:
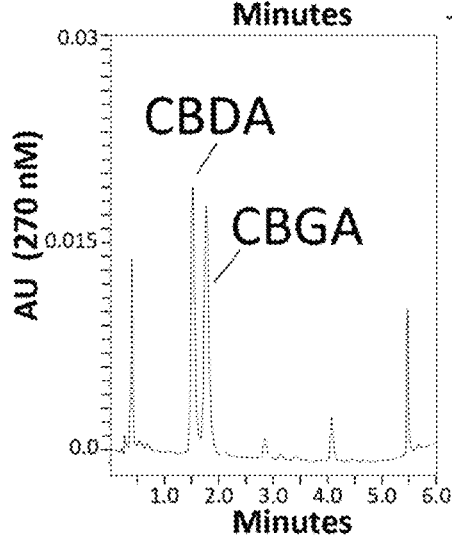
Figure 3:
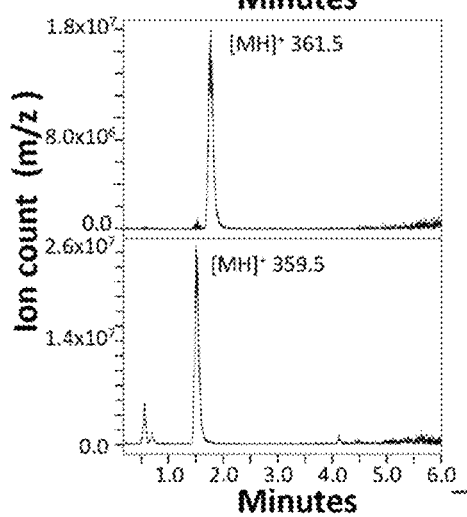

As shown in FIG. 3, introduction of polynucleotide pU092 (SEQ ID NO: 15) into a strain co-expressing a polynucleotide pU061 (SEQ ID NO: 16) (FIG. 3A and FIG. 3B) results in accumulation of CBGA (m/z 361.5 Da) and CBDA (m/z 359.5) cannabinoids (FIG. 3C and FIG. 3D, respectively). Both compounds were confirmed by direct comparison with respective analytical standards based on identical HPLC elution time, UV spectra (CBDA: λmax 229, 268, and 305; CBDA: λmax 227, 268 and 306), and the occurrence of the major ionized fragments (CBGA: m/z 343.4 and 361.5 Da; CBDA: m/z 341.4 and 359.5).

These data demonstrate the utility of and effectiveness of recombinant polynucleotides permitting expression of *Cannabis sativa* genes CvHCS, CvOAS, CvTKC, CvPT1, and CvCBDAS to yield cannabinoids in engineered microorganisms, and in particular in regulating the production of CBGA and CBDA in microbial cells.

Identical methods were used to generate transformants expressing THCA and CBCA synthases. For example, a construct encoding THCA synthase pU064 is disclosed as SEQ ID NO: 17 and described below.

For THCA biosynthesis, we initially constructed a microalgae strain S2 expressing Geranyl-diphosphate:olivetolate geranyltransferase and Δ1-tetrahydrocannabinolic acid synthase genes from *Cannabis sativa* (SEQ ID NO: 4 and 7, respectively) that encode enzymes converting olive-tolic/divarinic acids stepwise into cannabigerolic/cannab-igerovarinic (CBGA/CBGVA) and Δ9-tetrahydrocannabino-lic/Δ9-tetrahydrocannabivarinic (THCA/THCVA) acids. A transforming construct and the sequences of the genes are provided in SEQ ID NO: 17 [pU064]. The two cannabinoid genes were synthesized in a codon-optimized form to reflect *Prototheca moriformis* codon usage. Construct pU064 can be written as Thi4_5'::PmHXT1-NeoR-CvNR:PmACP1p-CsTHCAS-PmHSP90:PmSAD2p-PmIPDStp-CsPT-SAD2::Thi4_3'. The 5' and 3' ends of the construct represent genomic DNA from *Prototheca moriformis* that target integration of the construct to the Thi4 (thiamine biosynthesis) locus via homologous recombination. Proceeding in the 5' to 3' direction, the selection cassette has the *Prototheca moriformis* hexose transporter (HXT1) promoter driving expression of the *Escherichia coli* neomycin phosphotransferse gene NPTII (conferring the resistance to antibiotic G418) and the *Prototheca moriformis* heat-shock protein (HSP90) gene 3' UTR. The second expression cassette containing the codon optimized THCA synthase gene from *Cannabis sativa* (CsTHCAS, SEQ ID NO: 7) without the native N-terminal secretion pathway targeting peptide, is driven by the *Prototheca moriformis* acyl carrier protein (ACP1) promoter and has the *Prototheca moriformis* heat shock protein or in (HSP90) gene 3' UTR. The third expression cassette containing the codon optimized prenyl transferase gene from *Cannabis sativa* (CsPT1, SEQ ID NO: 4) fused to the *Prototheca moriformis* isopentenyl diphosphate synthase (IPDS) plastid-targeting transit peptide (SEQ ID NO: 13), is driven by the *Prototheca moriformis* Stearoyl ACP desaturase (SAD2) promoter and has the *Prototheca moriformis* Stearoyl ACP desaturase (SAD2) gene 3' UTR.

Alternative versions of polynucleotide pU064 included additional forms of geranyl-diphosphate:olivetolate geranyl-transferase (CsPT1) gene, synthesized with either native (SEQ ID NO: 4), "CsPT1tp", or with modified plastid transit peptides from *Chlorella* protothecoides (Cp) (SEQ ID NO: 11) or *Prototheca moriformis* (SEQ ID NO: 12, and 14) in place of the native transit peptide. The modified transit peptides derived from the CpSAD1 gene, "CpSAD1tp", from PmSAD1 gene, "PmSAD1tp", from PmIPDS gene, "PmIPDStp", from PmFAD2 gene, "PmFAD2tp", were synthesized as an in-frame, N-terminal fusions to the CBGA/CBGVA prenyl transferase in place of the native transit peptide.

Transgenic strains were generated via transformation of Prototheca moriformis (UTEX1435) R2 strain with polynucleotide pU064 (SEQ ID NO: 17) using lithium acetate/PEG method and positive transformants were selected on solid agar plates in the presence of 100 µg/mL of antibiotic G418. Transformations, cell culture, and gene expression analysis were all carried out as in WO2013/158938 and as described above. Positive transformation clones were verified by genomic PCR and/or RT-PCR to identify clones that are expressing mRNA encoding SEQ ID NO: 4-7, and cryopreserved.

To generate microalgae strains capable of synthesizing THCA, cryopreserved R2-pU064 strain S2 expressing high levels of CsPT1 and CsTHCAS genes (SEQ ID NO: 17) was transformed with polynucleotide pU092 (SEQ ID NO: 15). Positive clones were identified as colonies growing on agar plates lacking thiamine in the presence of antibiotic G418. The organization and expression of five Cannabis genes was subsequently verified by genomic PCR and/or RT-PCR, and selected representative strains were cryopreserved.

Positive S2-pU092 clones obtained after the expression construct pU092 for SEQ ID NO: 1-3 is incorporated into Prototheca moriformis R2-pU64 strain S2 were grown in A2 media as described in Examples 1 and 3 for 48 hours. The 120 ul of these cultures were transferred into 1.5 ml fresh A2 media modified to include 1.89 mM Ammonium sulfate, 4% glucose, 100 mM Pipes, pH 7.0, 1×Vitamin Cocktail lacking thiamine hydrochloride, and supplemented with 3 uM of sodium hexanoate. Fermentations were carried out for 5 days at 28° C. with agitation (200 rpm) in a 15 ml bioreactor tubes. Cells were fed with 3% glucose and 3 uM hexanoic acid after 48 and 72 hours. Total lipid samples were prepared from dried biomass from each transformant as described in Example 2 and products were analyzed using UHPLC-PDA/MS chromatography as described above in Example 2.

Figure 4:
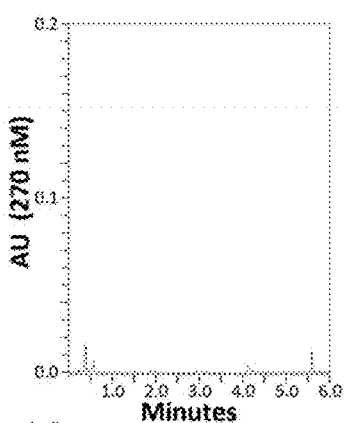
FIG. 4 illustrates biosynthesis of CBGA and THCA in *Prototheca moriformis*. HPLC chromatograms (AU 270 nM) of representative wild-type (R2) (FIG. 4A) and two representative R2 transformed with pU064 (strain S2, SEQ ID NO: 17) and pU092 (SEQ ID NO: 15) (FIG. 4B and FIG. 4C, respectively) strains demonstrate accumulation of CBGA and THCA in microalgae (R2-064-092-1 and R2-064-092-2). Elution of Δ9-tetrahydrocannabinolic and cannabigerolic acids at ca. 4.2 and 1.9 min, respectively, is confirmed by MS (FIG. 4D and FIG. 4E, respectively).
Figure 4:
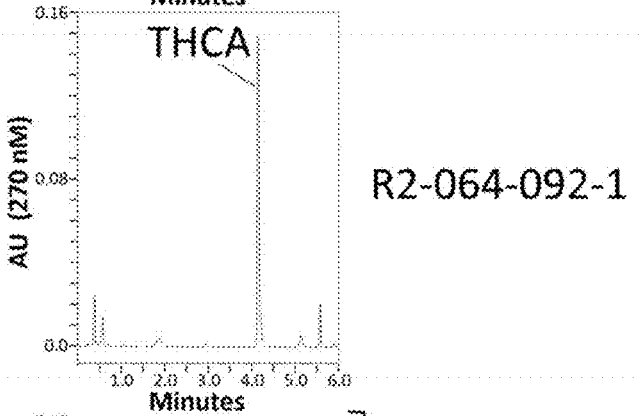
Figure 4:
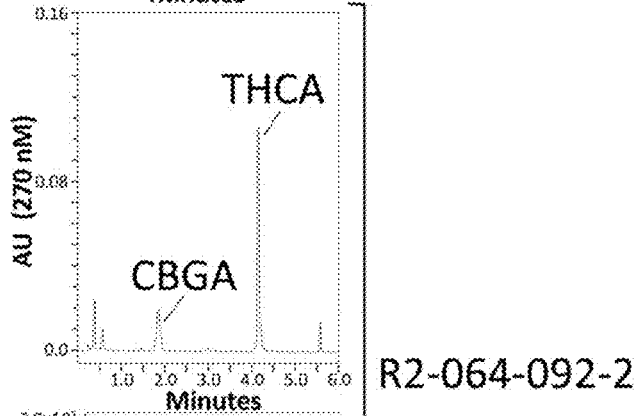
Figure 4:
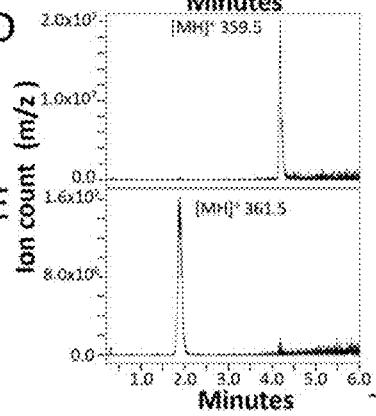

As shown in FIG. 4, introduction of polynucleotide pU092 (SEQ ID NO: 15) into a strain co-expressing a polynucleotide pU064 (SEQ ID NO: 17) (FIG. 4A, FIG. 4B, and FIG. 4C) results in accumulation of THCA (m/z 359.5) and CBGA (m/z 361.5 Da) cannabinoids (FIG. 4D and FIG. 4E, respectively). Both compounds were confirmed by direct comparison with respective analytical standards based on identical HPLC elution time, UV spectra (CBDA: λmax 229, 268, and 305; THCA: λmax 227, 271 and 305), and the occurrence of the major ionized fragments (CBGA: m/z 343.4 and 361.5 Da; THCA: m/z 341.4 and 359.5). The cannabinoid profiles (expressed as % of total CBGA and THCA calculated using standards curves) of P. moriformis UTEX 1435 untransformed strain R2 and five positive transformants (strains R2-064-092-1 through 5) are presented in Table 2.

TABLE 2

Produciton of cannabinoids in Prototheca moriformis UTEX 1435 expressing Cannabis sativa cannabinoid biosynthetic genes

| Strain | % CBGA | % THCA | Productivity, total cannabinoids, mg/L |
|---|---|---|---|
| R2 | 0 | 0 | — |
| R2-064-092-1 | 3 | 97 | 5.4 |
| R2-064-092-2 | 15 | 85 | 4.5 |
| R2-064-092-3 | 7.7 | 92.3 | 3.1 |
| R2-064-092-4 | 33 | 67 | 7.5 |
| R2-064-092-5 | 30 | 70 | 8.8 |

As shown in Table 2, the impact of expression of Cannabis sativa cannabinoid biosynthetic genes is a clear accumulation of CBGA and THCA compounds in the transformed microorganisms. Most strains predominantly synthesised THCA, from 67% in the lowest to 97% in the highest producer, which is consistent with CvTHCAS gene acting as a final genetic step. While we observed variation in the CBGA/THCA composition, most strains (except R2-064-092-3) demonstrated comparable productivities with strain R2-064-092-5 yielding as high as 8.8 mg/L total cannabinoid titer.

These data demonstrate the utility of and effectiveness of recombinant polynucleotides permitting expression of Cannabis sativa genes CvHCS, CvOAS, CvTKC, CvPT1, and CvTHCAS to yield cannabinoids in engineered microorganisms, and in particular in regulating the production of CBGA and THCA in microbial cells.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. Citation of references herein is not an admission that such references are prior art to an embodiment of the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

We claim:

1. A *Prototheca* host cell comprising a first nucleic acid encoding a hexanoyl-CoA synthase, a second nucleic acid encoding a 3,5,7-trioxododecanoyl-CoA synthase, a third nucleic acid encoding an olivetolic acid cyclase (or 3,5,7-trioxododecanoyl-CoA CoA-lyase), and a fourth nucleic acid encoding a geranyl-diphosphate:olivetolate geranyl-transferase, wherein the first, second, third and fourth nucleic acids are derived from *Cannabis sativa*, and wherein the first nucleic acid is operably linked to a control region, wherein the second nucleic acid is operably linked to a control region, wherein the third nucleic acid is operably linked to a control region, and wherein the fourth nucleic acid is operably linked to a control region.

2. The *Prototheca* host cell of claim 1, wherein the microalgae host cell is a *Prototheca* microalgae host cell.

3. The *Prototheca* host cell of claim 2, further comprising a fifth nucleic acid encoding a cannabichromenic acid synthase, and wherein the fifth nucleic acid is operably linked to a control region.

4. The *Prototheca* host cell of claim 2, further comprising a fifth nucleic acid encoding a cannabidiolic-acid synthase, and wherein the fifth nucleic acid is operably linked to a control region.

5. The *Prototheca* host cell of claim 2, further comprising a fifth nucleic acid encoding a Δ1-tetrahydrocannabinolic acid synthase, and wherein the fifth nucleic acid is operably linked to a control region.

6. The *Prototheca* host cell of claim 3, further comprising a sixth nucleic acid encoding a cannabidiolic-acid synthase, and wherein the sixth nucleic acid is operably linked to a control region.

7. The *Prototheca* host cell of claim 6, further comprising a seventh nucleic acid encoding a Δ1-tetrahydrocannabinolic acid synthase, and wherein the seventh nucleic acid is operably linked to a control region.

8. The *Prototheca* host cell of claim 2, further comprising a hexanoic acid.

9. The *Prototheca* host cell of claim 8, further comprising a cannabigerolic acid.

10. The *Prototheca* host cell of claim 2, further comprising a butyric acid.

11. The *Prototheca* host cell of claim 10, further comprising a cannabigerovarinic acid.

12. The *Prototheca* host cell of claim 3, further comprising a hexanoic acid.

13. The *Prototheca* host cell of claim 12, further comprising a cannabichromenic acid.

14. The *Prototheca* host cell of claim 3, further comprising a butyric acid.

15. The *Prototheca* host cell of claim 14, further comprising a cannabichromevarinic acid.

16. The *Prototheca* host cell of claim 4, further comprising a hexanoic acid.

17. The *Prototheca* host cell of claim 16, further comprising a cannabidiolic acid.

18. The *Prototheca* host cell of claim 4, further comprising a butyric acid.

19. The *Prototheca* host cell of claim 18, further comprising a cannabidivarinic acid.

20. The *Prototheca* host cell of claim 5, further comprising a hexanoic acid.

\* \* \* \* \*